United States Patent
Hansen et al.

(10) Patent No.: US 7,501,498 B2
(45) Date of Patent: Mar. 10, 2009

(54) ALPHA-FETOPROTEIN IMMU31 ANTIBODIES AND FUSION PROTEINS

(75) Inventors: Hans J. Hansen, Picayune, MS (US); Zhengxing Qu, Warren, NJ (US); David M. Goldenberg, Mendham, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 0 days.

(21) Appl. No.: 11/870,627

(22) Filed: Oct. 11, 2007

(65) Prior Publication Data
US 2008/0146784 A1    Jun. 19, 2008

Related U.S. Application Data

(62) Division of application No. 10/631,722, filed on Aug. 1, 2003, now Pat. No. 7,300,655.

(60) Provisional application No. 60/399,707, filed on Aug. 1, 2002.

(51) Int. Cl.
*C07K 16/00* (2006.01)
*C12P 21/08* (2006.01)
*C12P 21/04* (2006.01)
*A61K 39/395* (2006.01)
*C07H 21/04* (2006.01)

(52) U.S. Cl. .............. 530/387.3; 424/130.1; 424/133.1; 424/141.1; 424/178.1; 435/69.6; 530/388.1; 530/388.85; 530/391.3; 530/391.7

(58) Field of Classification Search ........................ None
See application file for complete search history.

(56) References Cited

U.S. PATENT DOCUMENTS

| | | | |
|---|---|---|---|
| 4,036,945 | A | 7/1977 | Haber |
| 4,331,647 | A | 5/1982 | Goldenberg |
| 4,704,692 | A | 11/1987 | Ladner |
| 4,824,659 | A | 4/1989 | Hawthorne |
| 4,946,778 | A | 8/1990 | Ladner et al. |
| 5,057,313 | A | 10/1991 | Shih et al. |
| 5,229,275 | A | 7/1993 | Goroff |
| 5,443,953 | A | 8/1995 | Hansen et al. |
| 5,567,610 | A | 10/1996 | Borrebaeck et al. |
| 5,633,425 | A | 5/1997 | Lonberg et al. |
| 5,716,595 | A | 2/1998 | Goldenberg |
| 5,753,206 | A | 5/1998 | McBride et al. |
| 5,827,690 | A | 10/1998 | Meade et al. |
| 6,077,499 | A | 6/2000 | Griffiths et al. |
| 6,096,289 | A | 8/2000 | Goldenberg |
| 6,254,868 | B1 | 7/2001 | Leung et al. |
| 6,331,175 | B1 | 12/2001 | Goldenberg |
| 6,761,876 | B2 | 7/2004 | Serbedzija et al. |
| 2002/0032315 | A1 | 3/2002 | Baca et al. |

FOREIGN PATENT DOCUMENTS

| | | |
|---|---|---|
| WO | 98/44001 | 10/1998 |
| WO | 00/29584 A1 | 5/2000 |
| WO | 00/63403 A2 | 10/2000 |
| WO | 01/00245 | 1/2001 |

OTHER PUBLICATIONS

Tsukada et al. (Cancer Research 47, 4293-4295, Aug. 15, 1987).
Amato et al. (J Cancer Res Clin Oncol, 2000, 126:161-167).
Laderoute and Pilarski. 1994. Anticancer Research 14:2429-2438.
Bergmann et al. 1987. Eur J Nuc Med 13:385-390.
Asano et al. 1998. Hybridoma vol. 17(2):185-190.
Takahashi et al. 1987. NCL Monogr 3:101-105.
Ishii et al. 1983. Annals New York Academy of Sciences pp. 270-276.
Tsukada et al. 1982. Proc. Natl. Acad. Sci. USA 79:7896-7899.
Goldenberg et al. 1987. J Clin Oncol 5(11):1827-1835.
Grimm et al. 2000. Gastroenterology 119:1104-1112.
Malamitsi et al. 1999. Anticancer Res 19:2201-2204.
William E Paul, M.D., ed., Fundamental Immunology 242. 3d ed. 1993.
Ansel et al., Pharmaceutical Dosage Forms and Drug Delivery Systems, 5th Ed., Lea & Feibiger (1990).
Ausubel et al., Current Protocols in Molecular Biology, John Wiley & Sons, New York (1987).
Baines et al., "Purification of Immunoglobulin G (IgG)", Methods in Molecular Biology, vol. 10, pp. 79-104, The Humana Press, Inc. (1992).
Barbas et al., Methods: A Companion to Methods in Enzymology, 2:119 (1991).
Barnes et al., Cytotechnology, 32:109-123 (2000).
Bei et al., J. Immunol. Methods, 186:245 (1995).
Bird et al., "Single Chain Antibody Variable Regions", TIBTECH, vol. 9:132-137 (1991).
Caron et al., J. Ex. Med., 176:1191-1195 (1991).
Carter et al., Proc. Natl. Acad. Sci USA, 89:4285 (1992).
Co et al., J. Immunol., 148:1149 (1992).
Coligan et al. (eds.), Current Protocols in Immunology, vol. 1, pp. 2.5.1-2.6.7; pp. 2.7.1-2.7.12; 2.8.1-2.8.10; 2.9.1-2.9.3, and 2.10-2.10.4, John Wiley & Sons (1991).
Colman, Biochem. Soc. Symp., 63:141-147 (1998).
Coloma et al., Nature Biotech, 15:159-163 (1997).
Courtenay-Luck, "Genetic Manipulation of Monoclonal Antibodies", Monoclonal Antibodies: Production, Engineering, and Clinical Application, Cambridge University Press (1995), Ritter et al., eds., pp. 166-179.
Cragg et al., Curr. Opin. Immunol., 11:541-547 (1999).
Edelman et al., Methods in Enzymology, vol. 1, p. 422, Academic Press (1955).
Edelman et al., Proc. Natl. Acad. Sci. USA, 63:78-85 (1969).

(Continued)

*Primary Examiner*—David J. Blanchard
(74) *Attorney, Agent, or Firm*—Richard A. Nakashima

(57) ABSTRACT

The present invention provides humanized, chimeric and human anti-alpha-fetoprotein antibodies, fusion proteins, and fragments thereof. The antibodies, fusion proteins, and fragments thereof, as well as combinations with other suitable antibodies, are useful for the treatment and diagnosis of hepatocellular carcinoma, hepatoblastoma, germ cell tumors carcinoma and other AFP-producing tumors.

26 Claims, 12 Drawing Sheets

OTHER PUBLICATIONS

Fiedler et al., Biotech., 13:1090-1093 (1995).
Fiedler et al., Immunotechnology, 3:205-216 (1997).
Fitzgerald et al., Protein Eng., 10(10):1221-1225 (1997).
Gennaro, Remington's Pharmaceutical Sciences, 18th Ed., Mack Publishing Co. (1990).
Gennaro, Remington's Pharmaceutical Sciences, 19th Ed., vol. I and II, Mack Publishing Co. (1995).
Gillies et al., J. Immunol. Methods, 125:191 (1989).
Goldenberg, Ad. Exp. Med. Biol., 303:107-117 (1991).
Goldenberg et al. Int. J. Oncol, 35-11 (1993).
Goldenberg et al., Immunol. Today, 14:5-7 (1993).
Goldenberg, Am. J. Med., 94:297-312 (1993).
Goldenberg, CA-A Cancer J. for Clinicians, 44:43 (1994).
Goldenberg et al., Immunol. Today, 16:261-264 (1995).
Goodman and Gilman's The Pharmacological Basis of Therapeutics, 7th Ed., MacMillan Publishing Co. (1985).
Green et al., Nature Genet, 7:13 (1994).
Greene et al., Protective Groups in Organic Synthesis, John Wiley & Sons, New York (1999).
Hasan et al., Prog. Clin. Biol. Res., 288:471 (1989).
Huse, Antibody Engineering: A Practical Guide, Boerrebaeck, ed., W.H. Freeman & Co., pp. 103-120 (1992).
Huse et al., Science, 246:1274-1281 (1989).
Jackson et al., Br. J. Cancer, 78:181-188 (1998).
Jaffers et al., Transplantation, 41:572-578 (1986).
Johnson et al., Current Opin. Struct. Biol., 3:5564-5571 (1993).
Porter, Biochem. J., 73:119 (1959).
Jones et al., Nature, 321:522 (1986).
Jori et al., Photodynamic Therapy of Tumors and Other Diseases, Libreria Progetto (1985).
Kabat database, "Sequences of Proteins & Immunological Interest", Bethesda, MD, U.S. Department of Health and Human Services, Public Health Service, NIH (1991).
Karacay et al., Bioconjugate Chem., 11:842-854 (2000).
Kohler et al., Nature, 256:495 (1975).
Larrick et al., Methods: A Companion to Methods in Enzymology, 2:106 (1991).
Leung et al., Hybridoma, 13:469-476 (1994).
Leung et al., J. Immunol., 154:5919 (1995).
Leung et al., Mol. Immunol., 32:1413-1427 (1995).
Lonberg et al., Nature, 368:856 (1994).
Losman et al., Cancer, 80:2660 (1997).
Losman et al., Clin. Cancer Res., 5:3101 (1999).
Mack et al., Proc. Natl. Acad. Sci. USA, 92:7021-7025 (1995).
Mahiouz et al., J Immunol. Methods, 212:149-160 (1998).
McCafferty et al., Nature, 348:552-553 (1990).
Mendez et al., Nature Genetics, 15:146-156 (1997).
Mew et al., J. Immunol., 130:1473 (1983).
Mew et al., Cancer Res., 45:4380 (1985).
Miller, Ann. Rev. Microbiol., 42:177 (1988).
Nisonoff et al., Arch. Biochem. Biophys., 89:230 (1960).
Orlandi et al., Proc. Natl. Acad. Sci. USA, 86:3833 (1989).
Osbourn et al., Immunotechnology, 2:181-196 (1996).
Oseroff et al., Proc. Natl. Acad. Sci USA, 83:8744 (1986).
Oseroff et al., Photochem. Photobiol., 46:83 (1987).
Pastan et al., Cell, 47:641 (1986).
Pelegrin et al., Cancer, 67:2529 (1991).
Price, "Production and Characterization of Synthetic Peptide-Derived Antibodies", Monoclonal Antibodies: Production, Engineering, and Clinical Application, Ritter et al., eds., pp. 60-84, Cambridge University Press (1995).
Raag et al., "Single Chain Fvs", FASEB, vol. 9:73-80 (1995).
Reynolds et al., Int. J. Rad. Appl. Instrum. B, 16:121-125 (1989).
Ridder et al., Biotechnology, 13:255-260 (1995).
Riechmann et al., Nature, 332:323 (1988).
Saltzman et al., Biophys. J., 55:163 (1989).
Sambrook et al., Molecular Cloning: A Laboratory Manual, Cold Spring Harbor Laboratory, Second Ed., New York (1989).
Sandhu, Crit. Rev. Biotech., 12:437 (1992).
Sanger et al., Proc. Natl. Acad. Sci. USA, 74:5463-5467 (1977).
Sears et al., J. Biol. Response Med., 3:138-150 (1984).
Shawler et al., J. Immunol., 135:1530-1535 (1985).
Sherwood et al., Bio/Technology, 10:1446 (1992).
Shih et al., Int. J. Cancer, 41:832 (1988).
Shih et al., Int. J. Cancer, 46:1101 (1990).
Shopes, B.J. Immunol., 148:2918-2022 (1992).
Singer et al., J. Immun., 150:2844 (1993).
Tatsuta et al., Lasers Surg. Med., 9:422 (1989).
Taylor et al., Int. Immun., 6:579 (1994).
Tempest et al., Biotechnology, 9:266 (1991).
Tomizuka et al., Nature Genetics, 16:133 (1997).
Uhlmann, Gene, 71:29 (1988).
Upeslacis et al., "Modification of Antibodies by Chemical Methods", Monoclonal Antibodies: Principles and Applications, Birch et al., pp. 187-230, Wiley-Liss (1995).
Van den Bergh, Chem. Britain, 22:430 (1986).
Vaughan et al., Nat. Biotechnol., 14:309-314 (1996).
Verhoeyen et al., Science, 239:1534 (1988).
Ward et al., "Genetic Manipulation and Expression of Antibodies", Monoclonal Antibodies: Principles and Applications, Wiley-Liss, Inc., Birch et al. (eds.), pp. 137-185 (1995).
Werner et al., Arzneim.-Forsch./Drug Res., 48(II), NR. 8, 870-880 (1998).
Winter et al., Ann. Rev. Immunol., 12:433 (1994).
Wong, Chemistry of Protein Conjugation and Cross-Linking, CRC Press (1991).
Wosnick et al., Gene, 60:115 (1988).
Yang et al., Appl. Environ. Microbiol., 64:2869-2874 (1998).
Yu et al., Int. J. Cancer, 56:244 (1994).
Zhu et al., Biotechnology, 14:192-196 (1996).
Database WPI Week 9121, Derwent Publications Ltd., London, GB.
Dresel, S., et al., "Detection of Hepatocellular Carcinoma with a New Alpha-Fetoprotein Antibody Imaging Kit", Journal of Clinical Oncology, vol. 15, No. 7, pp. 2683-2690, Jul. 1997.
Goldenberg, D., "Targeted Therapy of Cancer with Radiolabeled Antibodies", The Journal of Nuclear Medicine, vol. 43, No. 5, pp. 693-713, May 2002.
Z. Qu et al., Humanization of Immu31, an alpha-fetoprotein-specific antibody, Clinical Cancer Research, vol. 5, No. 10 suppl., Oct. 1999, pp. 3095S-3100s, (1999).

```
GTGAAGCTGCAGGAGTCAGGACCTGAACTGGTAAAGCCTGGGGCTTCAGTGAAGATGTCCTGCAAGGCTTCTGGATACGCTTTCACTAGC      90
 V  K  L  Q  E  S  G  P  E  L  V  K  P  G  A  S  V  K  M  S  C  K  A  S  G  Y  A  F  T  S
 2                      10                      20                      30
TATGTTATACACTGGGTGAGGCAGAGGCCAGGGCAGGGCCTTTATTGGATTGGATATATTCATCCTTACAATGGTGTTACCAAGTACAAT      180
 Y  V  I  H  W  V  R  Q  K  P  G  Q  G  L  Y  W  I  G  Y  I  H  P  Y  N  G  G  T  K  Y  N
         CDR1           40                      50    52 A              60
                                                              CDR2
GAGAAGTTCAAAGGCAAGGCCACACTGACTTCAGACAAATCGTCCAGCACAACCTACATGGAGCTCAGCAGCCTGACCTCTGAGGACTCT      270
 E  K  F  K  G  K  A  T  L  T  S  D  K  S  S  S  T  T  Y  M  E  L  S  S  L  T  S  E  D  S
                        70                      80    82 A  B  C
GCGGTCTATTACTGTGCAAGATCTGGGGGGGAGACCCTTTGCTTACTGGGGCCAAGGGACTCTGGTCACTGTCTCTGCA      351
 A  V  Y  Y  C  A  R  S  G  G  G  D  P  F  A  Y  W  G  Q  G  T  L  V  T  V  S  A
         90                      100 A              110       113
                   CDR3
```

Figure 1A.

```
GACATTCAGCTGACCCAGTCTCCATCCTCACTGTCTGCATCTCTGGGAGGCAAAGTCACCATCACTTGCAAGGCAAGCCAAGACATTAAC
 1                          10                        20                        30
 D  I  Q  L  T  Q  S  P  S  S  L  S  A  S  L  G  G  K  V  T  I  T  C  K  A  S  Q  D  I  N
                                                                     CDR1

AAGTATATAGGTTGGTACCAACACAAGCCTGAAAAGGTCCTAGGCTACTCATGCATTACACATCTGCATTACTGCCAGGCATCCCATCA
                      40                        50                        60
 K  Y  I  G  W  Y  Q  H  K  P  G  K  G  P  R  L  L  M  H  Y  T  S  A  L  L  P  G  I  P  S
 CDR1                                                        CDR2

AGGTTCAGTGGAAGTGGGTCTGGGAGAGATTATTCCTTCAGCATCAGCAACCTGAGCCTGAAGATATTGCAACTTATTATTGTCTACAG
                      70                        80                        90
 R  F  S  G  S  G  S  G  R  D  Y  S  F  S  I  S  N  L  E  P  E  D  I  A  T  Y  Y  C  L  Q

TATGATGATCTGTGGACGTTCGGTGAGGCACCAAGCTGGAAATGAAACGG
 94 96               100               108
 Y  D  D  L  W  T  F  G  G  G  T  K  L  E  M  K  R
 CDR3
```

Figure 1B.

```
        PstI
CAGGTCCAG TGCAG GAGTCAGGACCTGAACTGGTAAAGCCTGGGGCTTCAGTGAAGATGTCCTGCAAGGCTTCACT    90
1                         10                  20                  30
 Q  V  Q  L  Q  E  S  G  P  E  L  V  K  P  G  A  S  V  K  M  S  C  K  A  S  G  Y  A  F  T

AGCTATGTTATACACTGGGTGAGGCAGAAGCCTGGGCAGGGCCTTGATTGGATATATTCATCCTTACAATGGTGGTACCAAGTAC   180
                40                  50       52  A              60
 S  Y  V  I  H  W  V  R  Q  K  P  G  Q  G  L  Y  W  I  G  Y  I  H  P  Y  N  G  G  T  K  Y
         CDR1                                       CDR2

AATGAGAAGTTCAAAGGCAAGGCCACACTGACTTCAGACAAATCGTCCAGCACTACATGGAGCTCAGCAGCCTGACCTCTGAGGAC   240
     60                  70                  80  82 A B C
 N  E  K  F  K  G  K  A  T  L  T  S  D  K  S  S  S  T  T  Y  M  E  L  S  S  L  T  S  E  D

BstEII
TCTGCGGTCTATTACTGTGCAAGATCTGGGGGGGGAGACCCTTTGCTTACTGGGGCCAAGGGACCAC GGTCACC GTCTCCTCA   333
                90                 100 A                           110       113
 S  A  V  Y  Y  C  A  R  S  G  G  G  D  P  F  A  Y  W  G  Q  G  T  T  V  T  V  S  S
                            CDR3
```

Figure 2A.

```
        PvuII
GACATCCAGCTGACCCAGTCTCCATCCTCACTGTCTGCATCTCTGGGAGGCAAAGTCACCATCACTTGCAAGGCAAGACAGACATTAAC    90
  1                 10                  20                  30
  D  I  Q  L  T  Q  S  P  S  S  L  S  A  S  L  G  G  K  V  T  I  T  C  K  A  S  Q  D  I  N

AAGTATATAGGTTGGTACCAACAGAAGCCTGGAAAAGGTCCTAGGCTACTCATGCATTACACATCTGCATTACTCCCAGGCATCCCATCA   180
                    40                  50                  60
  K  Y  I  G  W  Y  Q  H  K  P  G  K  G  P  R  L  L  M  H  Y  T  S  A  L  L  P  G  I  P  S
  CDR1                                                         CDR2

AGGTTCAGTGGAAGTGGGTCTGGGAGAGATTATTCCTTCAGCATCAGCAACCTGAGCCTGAAGATATTGCAACTTATTATTGTCTACAG
                    70                  80                  90
  R  F  S  G  S  G  S  G  R  D  Y  S  F  S  I  S  N  L  E  P  E  D  I  A  T  Y  Y  C  L  Q

BglII/BclI
TATGATGATCTGTGGACGTTCGGTGGAGGGACCAAGCTGGAGATCAAAACGA                                         336
          94 96          100                 108
  Y  D  D  L  W  T  F  G  G  G  T  K  L  E  I  K  R
  CDR3
```

Figure 2B.

```
                1                   10                  20                          30               40
EUVH        PVQLVQSGAEVKKPGSSVKVSCKASGGTFS              RSAIIWVRQA
Immu31VH    - · K · QE · · P · LV · · · A · · · M · · · · · · YA · TSYV · H · · · · · K
hImmu31VH   Q · · · · · · · · · Q · · · · · · · · · · · · · · YA · TSYV · H · · · · · ·

50  52 A                    60                      70
EUVH        PGQGLEWMG                GIVPMFGPPNYAQKFQG           RVTITADESTNTAY
Immu31VH    · · · · · · · · · Y · I · · Y · H · YN · GTK · NE · · K · KA · L · S · K · SS · T ·
hImmu31VH   · · · · · · · · · Y · I · · Y · H · YN · GTK · NE · · K · KA · · · · · · · · · · · ·

80  82 A B C             90                      100 A                 110     113
EUVH        MELSSLRSEDTAFYFCAG        GYGIYS-PEEYNGGLVTVSS
Immu31VH    · · · · · · · · · · · · · · · · · T · · · S · V · Y · ·     RSG · GDPFAY
hImmu31VH   · · · · · · · · · · · · · · · · · · · · · · · · · · · ·     RSG · GDPFAY 103                     110   113
NEWMVH      WGQGSLVTVSS
Immu31VH    · · · · T · · · · · A
hImmu31VH   · · · · · · · · · · ·
```

Figure 4A.

```
              1                    10                  20                  30              40
REI           DIQMTQSPSSLSASVGDRVTITCQASQDIIKYLNWYQQTP
Immu31Vκ      ...L..........L.GK.....K...N..IG....HK.
hImmu31Vκ     ...L...................K...N..IG.....K.

50                  60                  70              80
REI           GKAPKLLIYEASNLQAGVPSRFSGSGSGTDYTFTISSLQP
Immu31Vκ      ..G.R...MHYT.A.LP.I.............R..S.S..N.E.
hImmu31Vκ     ........MHYT.A.LP.I.............R...........

90                  100                 108
REI           EDIATYYQQYQSLPYTFGQGTKLQITR
Immu31Vκ      ........L.DD-W..G.....EMK.
hImmu31Vκ     ........L.DD-W..G........K.
```

Figure 4B.

```
                  1                   10                  20                  30        40
hImmu31Vk      DIQLTQSPSSLSASVGDRVTITC KASQDINKYIG WYQQKP
hImmu31VkT69   ......................  ..........  ......
hImmu31VkT39   ......................  ..........  ....T.

GKAPKLLMH YTSALLP GIPSRFSGSGSGRDYTFTISSLQP
                        50                  60                  70        80
hImmu31Vk      GKAPKLLMH YTSALLP GIPSRFSGSGSGRDYTFTISSLQP
hImmu31VkT69   .........  ......  ........................
hImmu31VkT39   .........  ......  ...................T....

EDIATYYC LQYDDLWT FGGGTKLQIKR
                       90      96       100      108
hImmu31Vk      EDIATYYC LQYDDLWT FGGGTKLQIKR
hImmu31VkT69   ........  ........  ...........
hImmu31VkT39   ........  ........  ...........
```

Figure 4C.

```
CAGGTCCAGCTGCAGCAATCAGGGGCTGAAGTCAAGAAACCTGGGTCATCAGTGAAGGTCTCCTGCAAGGCTTCTGGCTACGCTTTTACT      90
 1                                  10                  20                  30
 Q  V  Q  L  Q  Q  S  G  A  E  V  K  K  P  G  S  S  V  K  V  S  C  K  A  S  G  Y  A  F  T

AGCTATGTTATACACTGGGTCAGGCAGGCACCTGGACAGGGTCTGTATTGGATTGGATATATTCATCCTTACAATGTGTACCAAGTAC     180
                    40                            50     52 A
 S  Y  V  I  H  W  V  R  Q  A  P  G  Q  G  L  Y  W  I  G  Y  I  H  P  Y  N  G  G  T  K  Y
    CDR1                                              CDR2

AATGAGAAGTTCAAAGGCAAGGCCACAATAACAGCTGACGAATCCACCAATACAGCCTACATGGAGCTGAGCAGCCTGAGGTCTGAGGAC     270
60                        70                          80   82 A B C
 N  E  K  F  K  G  K  A  T  I  T  A  D  E  S  T  N  T  A  Y  M  E  L  S  S  L  R  S  E  D

ACGGCATTTTATTTTTGTGCAAGATCTGGGGGGGGAGACCCTTTTGCTTACTGGGGCCAAGGCTCCCTGGTCACCGTCTCCTCA          354
               90                    100 A                            110        113
 T  A  F  Y  F  C  A  R  S  G  G  G  D  P  F  A  Y  W  G  Q  G  S  L  V  T  V  S  S
                         CDR3
```

Figure 5A.

```
GACATCCAGCTGACCCAGTCTCCATCATCTCTGAGCGCATCTGTTGGAGATAGGGTCACTATCACTTGTAAGGCAAGCCAAGACATTAAC      90
1                       10                      20                      30
D   I   Q   L   T   Q   S   P   S   S   L   S   A   S   V   G   D   R   V   T   I   T   C   K   A   S   Q   D   I   N

AAGTATATAGGTTGGTACCAGCAGAAACCAGGGAAAGCACCTAAACTGCTCATTACACATCTGCTATTACTGCCAGGTATCCCTTCG         180
                        40                      50                                      60
K   Y   I   G   W   Y   Q   Q   K   P   G   K   A   P   K   L   L   M   H   Y   T   S   A   L   L   P   G   I   P   S
    CDR1                                                                CDR2

CGATTCTCTGGCAGCGGATCTGGGACAGAGATTATACTTTCACCATCAGCTCTCTTCAACCAGAAGACATTGCAACATATTATTGTCTACAG    270
                        70                      80                                      90
R   F   S   G   S   G   S   G   T   D   Y   T   F   T   I   S   S   L   Q   P   E   D   I   A   T   Y   Y   C   L   Q

TATGATGATCTGTGGACGTTCGGTGGAGGGACCAAGCTGCAGATCAAACGA                                              321
        94 96          100              108
Y   D   D   L   W   T   F   G   G   G   T   K   L   Q   I   K   R
        CDR3
```

ALPHA-FETOPROTEIN IMMU31 ANTIBODIES AND FUSION PROTEINS

CROSS REFERENCE TO RELATED APPLICATIONS

This application is a divisional of U.S. patent application Ser. No. 10/631,722, filed Aug. 1, 2003, now U.S. Pat. 7,300,655, which claims priority to U.S. Provisional Application No. 60/399,707, filed Aug. 1, 2002, both of which are incorporated herein by reference in its their entirety.

BACKGROUND OF THE INVENTION

1. Field of the Invention

The present invention relates to humanized, chimeric and human alpha-fetoprotein (AFP) antibodies, particularly therapeutic and diagnostic conjugates of humanized, chimeric and human forms. In particular, the invention includes Immu31 antibodies and methods of treating hepatocellular carcinoma, germ cell tumors, and other AFP-producing tumors using humanized, chimeric and human antibody forms. The present invention also relates to antibody fusion proteins or fragments thereof comprising at least two Immu31 MAbs or fragments thereof or at least one Immu31 MAb or fragment thereof and at least one second MAb or fragment thereof, other than the Immu31 MAb or fragment thereof. The humanized, chimeric and human Immu31 MAbs, fragments thereof and antibody fusion proteins thereof, or fragments thereof, may be administered alone, conjugated to diagnostic and/or therapeutic agents, in combination with a therapeutic or diagnostic immunoconjugate, in combination with other naked antibodies, or with at least one therapeutic agent and/or diagnostic agent. The present invention further contemplates DNA sequences encoding humanized, chimeric and human Immu31 antibodies and fragments thereof, antibody fusion proteins and fragments thereof, vectors and host cells containing the DNA sequences, and methods of making the humanized, chimeric and human Immu31 antibodies.

2. Background

Monoclonal antibodies (MAbs) have wide diagnostic and therapeutic potentials in clinical practices against cancer. Early clinical trials revealed encouraging results using radiolabled MAbs for the diagnosis/detection (radioimmunodetection: RAID) and treatment (radioimmunotherapy: RAIT) of malignancies in cancer patients (Goldenberg et al., (1993) (Intl. J. Oncol. 3:5-11; Goldenberg et al., (1995) Immunol. Today 16:261-264; Goldenberg (1993) Am. J. Med. 94:297-312; Goldenberg (1991) Adv. Exp. Med. Biol., 303:107-117). Monoclonal antibodies play a central role in cancer immunotherapy, either in naked forms, or as conjugates to cytotoxic agents, such as radioisotopes, drugs, toxins, or prodrug-converting enzymes (Goldenberg et al., (1993) Immunol. Today, 14:5-7). These approaches are under active evaluation, with different levels of developmental and clinical successes. Naked MAbs potentially may achieve clinical responses by inducing a cytotoxic effect upon binding to cell surface proteins that are over-expressed on cancer cells. Studies have shown that these therapeutic effects were accomplished by controlling tumor growth via programmed cell death (apoptosis), or by the induction of anti-tumor immune responses (Cragg et al., (1999) Curr Opin. Immunol., 11:541-547).

The majority of clinically interesting antibodies were raised in mice. The problem of immunogenicity of murine MAbs in humans has been the major obstacle preventing their clinical application, especially in cancer therapy where large doses and repeated administrations are required to achieve maximum efficacy. It has been demonstrated that significant human-anti-mouse antibody (HAMA) responses were detected in approximately 50% of patients after a single injection of murine MAb; greater than 90% of patients developed HAMA following two or three repeated injections (Sears et al., (1984) J. Biol. Response Med. 3:138-150; Reynolds et al., (1989) Int. J. Rad. Appl. Instrum. B, 16:121-125; Shawler et al. (1985) J. Immunol., 135:1530-1535; Jaffers et al., (1986) Transplantation, 41:572-578). In addition, the therapeutic effects of these murine MAbs in humans, if any, are further mitigated with their short serum half-lives and inabilities to recruit human effector cells, such as complement-fixing cytotoxic T cells. With the advent of molecular engineering, we can now genetically modify the structure of an antibody without affecting its antigen specificity to minimize or eliminate the HAMA responses and simultaneously enhance its immune effector functions. The processes are called chimerization and humanization. These modified MAbs have been shown to possess attributes essential for enhanced clinical utility, i.e., decreased immunogenicities, longer serum half-lives in human, and the ability to recruit effector functions.

Alpha-fetoprotein (AFP) is a serum protein normally found at significant levels only in fetal blood. In adult blood, increased alpha-fetoprotein levels are associated with liver regeneration and certain carcinomas, such as hepatocellular carcinoma, hepatoblastoma, and germ cell tumors. Hepatocellular carcinoma (HCC or malignant hepatoma) is one of the most common cancers in the world, especially in Asia, certain parts of Africa, and is increasing in incidence in the West, probably related to the increased frequency of heptatis infections. Accordingly, there remains a need to develop new methods and approaches to treating HCC and other such cancers.

The present invention relates to murine, chimeric, humanized and fully human anti-alpha-fetoprotein antibodies and fragments thereof, particularly monoclonal antibodies (MAbs), therapeutic and detection/diagnostic immunoconjugates, and fusion proteins comprising at least one anti-AFP antibody or fragment thereof. Also contemplated herein are methods of diagnosing/detecting or treating a cancer using humanized, chimeric and fully human anti-AFP antibodies. The humanized, chimeric and fully human anti-AFP antibodies and fragments thereof, and antibody fusion proteins and fragments thereof, may be administered alone, as a therapeutic and/or diagnostic/detection conjugate or in combination with a therapeutic immunoconjugate, with other naked antibodies, or with other therapeutic agents or as a diagnositic/detection conjugate.

SUMMARY OF THE INVENTION

The present invention provides a monoclonal antibody (MAb) or fragment thereof that binds an alpha-fetoprotein (AFP) antigen. Preferably, the anti-AFP antibody or fragment thereof is an Immu31 antibody or fragment thereof, as defined below. Also preferred, the anti-AFP antibody or fragment thereof is a chimeric, fully human, mouse or humanized antibody or fragment thereof. Most preferably, the AFP antibody or fragment thereof is a humanized antibody or fragment thereof.

In a preferred embodiment, the humanized anti-AFP or Immu31 antibody or fragment thereof comprises the complementarity-determining regions (CDRs) of a light and heavy chain variable regions of a murine anti-AFP MAb and the framework (FR) regions of a light and heavy chain variable regions of a human antibody, and the light and heavy chain constant regions of a human antibody, wherein the CDRs of the light chain variable region of the humanized anti-AFP MAb comprises CDR1 comprising an amino acid sequence of KASQDINKYIG (SEQ ID NO: 1); CDR2 comprising an amino acid sequence of YTSALLP (SEQ ID NO: 2) and CDR3 comprising an amino acid sequence of LQYDDLWT (SEQ ID NO: 3); and the CDRs of the heavy chain variable region of the humanized anti-AFP MAb comprises CDR1 comprising an amino acid sequence of SYVIH (SEQ ID NO: 4); CDR2 comprising an amino acid sequence of YIH-PYNGGTKYNEKFKG (SEQ ID NO: 5) and CDR3 comprising an amino acid sequence of SGGGDPFAY (SEQ ID NO: 6).

In another embodiment, the humanized anti-AFP or Immu31 antibody or fragment thereof comprises at least one amino acid substituted from the corresponding position of the FR of the murine anti-AFP antibody or fragment thereof. Preferably, the murine amino acid from the murine anti-AFP MAb or fragment thereof is at least one amino acid selected from the group consisting of amino acid residue 5, 27, 28, 30, 46, 48, 66, 67 and 94 of the murine heavy chain variable region of FIG. 4A. Also preferred, the murine amino acid from the murine anti-AFP MAb or fragment thereof is at least one amino acid selected from the group consisting of amino acid residue 4, 39, 48, 49, 58, 69, 100 and 107 of the murine light chain variable region FIG. 4B. Most preferably, the anti-AFP antibody or fragment thereof comprises the Immu31 $V_K$ nucleotide sequence of FIG. 1B. Also preferred, the anti-AFP antibody or fragment thereof comprises the Immu31 $V_H$ nucleotide sequence of FIG. 1A.

In another embodiment, the humanized Immu31 antibody or fragment thereof comprises the hImmu31 $V_K$ nucleotide sequence of FIG. 5B. Still more preferably, the Immu31 antibody or fragment thereof comprises a hImmu31 $V_H$ nucleotide sequence of FIG. 5A.

Another embodiment is a CDR-grafted humanized heavy chain comprising the complementarity determining regions (CDRs) of a murine Immu31 MAb and the framework region of the heavy chain variable region of a human antibody and the heavy chain constant region of a human antibody, wherein the CDRs of the heavy chain variable region of the humanized anti-AFP MAb comprises CDR1 comprising an amino acid sequence of SYVIH (SEQ ID NO: 4); CDR2 comprising an amino acid sequence of YIHPYNGGTKYNEKFKG (SEQ ID NO: 5) and CDR3 comprising an amino acid sequence of SGGGDPFAY (SEQ ID NO: 6).

Similarly, a CDR-grafted humanized light chain comprising the complementarity determining regions (CDRs) of a murine Immu31 MAb and the framework region of the light chain variable region of a human antibody and the light chain constant region of a human antibody, wherein the CDRs of the light chain variable region of the humanized anti-AFP MAb comprises CDR1 comprising an amino acid sequence of KASQDINKYIG (SEQ ID NO: 1); CDR2 comprising an amino acid sequence of YTSALLP (SEQ ID NO: 2) and CDR3 comprising an amino acid sequence of LQYDDLWT (SEQ ID NO: 3), is also described herein as an additional embodiment.

In a preferred embodiment, the anti-AFP or Immu31 fragments of the present invention are selected from the group consisting of Fv, F(ab')$_2$, Fab' and Fab.

Also contemplated herein is a diagnostic/detection or therapeutic immunoconjugate comprising an antibody component that comprises any one of the anti-AFP or Immu31 MAbs or fragments thereof of the present invention, or an antibody fusion protein or fragment thereof that comprises any of the anti-AFP or Immu31 antibodies or fragments thereof of the present invention, wherein the antibody component is bound to at least one diagnostic/detection agent or at least one therapeutic agent. Preferably, the diagnostic/detection or therapeutic agent of the immunoconjugate according to the present invention is bound to said MAb or fragment thereof by means of a carbohydrate moiety.

In one embodiment, the diagnostic/detection immunoconjugate comprises at least one photoactive diagnostic/detection agent, such as a chromagen or dye at least one radionuclide with an energy between 20 and 10,000 keV, such as a gamma-, beta- or a positron-emitting isotope, a contrast agent, such as a radiopaque compound, a paramagnetic ion, including chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), or an ultrasound-enhancing agent, including a liposome that is conjugated to a humanized Immu31 or fragment thereof. The radiopaque compound may be selected from the group consisting of iodine compounds, barium compounds, gallium compounds and thallium compounds. In another embodiment, the diagnostic/detection described herein is used in intraoperative, endoscopic, or intravascular tumor detection/diagnosis.

Also contemplated herein is a therapeutic immunoconjugate comprising a therapeutic agent that is selected from the group consisting of a radionuclide, boron, gadolinium or uranium atoms, an immunomodulator, such as cytokine, a stem cell growth factor, a lymphotoxin, such as tumor necrosis factor (TNF), said hematopoietic factor is an interleukin (IL), said colony stimulating factor is granulocyte-colony stimulating factor (G-CSF) or granulocyte macrophage-colony stimulating factor (GM-CSF)), said interferon is interferons-α, -β or -γ, and said stem cell growth factor is designated "S1 factor," a hematopoietic factor, a colony stimulating factor (CSF), an interferon (IFN), a stem cell growth factor, erythropoietin, thrombopoietin, an antibody and a combination thereof, a cytokine, a hormone, a hormone antagonist, an enzyme, an enzyme inhibitor, a photoactive therapeutic agent, a cytotoxic drug, such as antimitotic, alkylating, antimetabolite, angiogenesis-inhibiting, apoptotic, alkaloid, COX-2-inhibiting and antibiotic agents and combinations thereof, or cytotoxic toxin, such as plant, microbial, and animal toxins, and a synthetic variation thereof, an angiogenesis inhibitor, a different antibody and a combination thereof. In a preferred embodiment, the cytokine is selected from the group consisting of IL-1, IL-2, IL-3, IL-6, IL-10, IL-12, IL-18, interferon-γ, TNF-α and a combination thereof, the radionuclide is selected from the group consisting of an Auger emitter, a beta-emitter and an alpha-emitter, such as P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213, Co-58, Ga-67, Br-80m, Tc-99m, Rh-103m, Pt-109, In-111, Sb-119, I-125, Ho-161, Os-189m, Ir-192, Dy-152, At-211, Bi-212, Ra-223, Rn-219, Po-215, Bi-211, Ac-225, Fr-221, At-217, Bi-213, Fm-255, B-10, Gd-157, U-235, and combinations thereof. Preferably, the radionuclide has an energy between 20 and 10,000 keV.

In another embodiment, the therapeutic agent conjugated to the anti-AFP or Immu31 antibody or fragment thereof is a photoactive therapeutic agent, such as a chromagen or dye.

Considered in the present invention also is a multivalent, multispecific antibody or fragment thereof comprising one or more antigen binding sites having affinity toward an AFP target antigen and one or more hapten binding sites having affinity towards hapten. Preferably, the anti-AFP or Immu31 antibody or fragment thereof is humanized. Also preferred, the antibody or fragment thereof is fully human or chimerized. In one embodiment, the multivalent, multispecific antibody or fragment thereof comprises a diagnostic/detection or therapeutic agent.

Also considered in the present invention is an antibody fusion protein or fragment thereof comprising at least two anti-AFP MAbs or fragments thereof, wherein the MAbs or fragments thereof are selected from any of the anti-AFP or Immu31 monoclonal antibodies or fragments thereof of the present invention. In a similar vein, an antibody fusion protein or fragment thereof comprising at least one first anti-AFP MAb or fragment thereof of any one the anti-AFP antibodies or fragments thereof of the present invention, and at least one second MAb or fragment thereof, other than any one of the anti-AFP MAbs or fragments thereof of the present invention, is also contemplated. In a preferred embodiment, the second MAb is a carcinoma associated antibody. In another preferred embodiment, the antibody fusion protein or fragment thereof further comprises a diagnostic/detection or therapeutic agent conjugated to the fusion protein or fragment thereof.

Considered herein is a method of treating a malignancy in a subject, comprising the step of administering to said subject a therapeutically effective amount of a naked and/or conjugated anti-AFP antibody, fusion protein, or fragment thereof of the present invention, formulated in a pharmaceutically acceptable vehicle, either alone or in combination with other therapeutic and/or diagnostic agents. Preferably, the method a method of treating a malignancy in a subject, comprising the step of administering to said subject a therapeutically effective amount of a immunoconjugate or fragment thereof the present invention, formulated in a pharmaceutically acceptable vehicle.

Similarly, a method of diagnosing/detecting a malignancy in a subject, comprising the step of administering to said subject a diagnostically effective amount of a naked or conjugated anti-AFP antibody, fusion protein, or fragment thereof of the present invention, formulated in a pharmaceutically acceptable vehicle.

Another embodiment is a method of treating or diagnosing/detecting a malignancy in a subject, comprising (i) administering to a subject in need thereof the anti-AFP antibody or fragments thereof of the present invention; (ii) waiting a sufficient amount of time for a desired amount of the non-binding protein to clear the subject's bloodstream; and (iii) administering to said subject a carrier molecule comprising a diagnostic agent, a therapeutic agent, or a combination thereof, that binds to a binding site of said antibody.

Another embodiment of the present invention is a DNA sequence and a vector comprising a DNA sequence, and a host cell comprising a DNA sequence, that comprises a nucleic acid encoding an anti-AFP MAb or fragment thereof selected from the group consisting (a) an anti-AFP MAb or fragment thereof of the present invention; (b) an antibody fusion protein or fragment thereof comprising at least two of said MAbs or fragments thereof; (c) an antibody fusion protein or fragment thereof comprising at least one first AFP MAb or fragment thereof comprising said MAb or fragment thereof of any one of the antibodies of the present invention and at least one second MAb or fragment thereof, other than the anti-AFP MAb or fragment thereof described in the present invention; and (d) an antibody fusion protein or fragment thereof comprising at least one first MAb or fragment thereof comprising said MAb or fragment thereof of any one of the antibodies of the present invention and at least one second MAb or fragment thereof, other than the anti-AFP MAb or fragment thereof of any one of the antibodies of the present invention, wherein said second MAb is selected from the group consisting of CEA, EGP-1, EGP-2 (e.g., 17-1A), MUC-1, MUC-2, MUC-3, MUC-4, PAM-4, KC4, TAG-72, EGFR, BER2/neu, BrE3, Le-Y, A3, Ep-CAM, Tn, and Thomson-Friedenreich antigens, tumor necrosis antigens, ferritin, acidic isoferritin, Ga 733, or a combination thereof. Other suitable second antibodies include those that bind tenascin, an oncogene, an oncogene product, IL-6, IGF-1, IGFR-1, tumor angiogenesis antigens, such as vascular endothelium growth factor (VEGF), placental growth factor (PlGF), ED-B fibronectin, and against other vascular growth factors.

A method of delivering a diagnostic/detection or therapeutic agent, or a combination thereof, to a target comprising (i) providing a composition comprising an immunoconjugate that comprises the antibody, fusion protein, or fragment thereof of any one of the antibodies, fusion proteins, or fragments thereof of the present invention and (ii) administering to a subject in need thereof said composition, is also described. Preferably, the diagnostic/detection agent comprises at least one photoactive diagnostic agent, such as a chromagen or dye, a contrast agent, such as a paramagnetic ion, an ultrasound-enhancing agent or a radiopaque compound used in X-rays or computed tomography, such as an iodine compound, barium compound, gallium compound or thallium compound. In one embodiment, the ultrasound enhancing agent is a liposome that comprises a humanized Immu31 or fragment thereof, and optionally, the liposome is gas-filled. In another embodiment, the diagnostic/detection agent preferably is a radionuclide with an energy between 20 and 2,000 keV, such as a gamma-, beta- or a positron-emitting isotope. Still preferred, the radionuclide is selected from the group consisting of F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, I-124, Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Also preferred, the radiopaque compound is selected from the group consisting of barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Similarly, in the method of delivering a diagnostic/detection or therapeutic agent, or a combination thereof, to a target, the therapeutic agent is preferably selected from the group consisting of a radionuclide, an immunomodulator, a hormone, a hormone antagonist, an enzyme, an enzyme inhibitor, a photoactive therapeutic agent, a cytotoxic agent, such as a drug or toxin (including a plant, microbial and animal toxin, and a synthetic variation thereof), and a combination thereof. Preferably, the drug is selected from the group consisting of antimitotic, alkylating, antimetabolite, antiangiogenic, apoptotic, anthracyclines, alkaloid, COX-2-inhibitor and antibiotic agents, and combinations thereof, nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antibiotics, enzymes, enzyme inhibitors, epipodophyllotoxins, platinum coordination complexes, vinca alkaloids, substituted ureas, methyl hydrazine derivatives, adrenocortical suppressants, hormones, hormone antagonists, endostatin, taxols, camptothecins, doxorubicins and their analogs, and a combination thereof. Also preferred, the toxin is selected from the group consisting of ricin, abrin, alpha toxin, saporin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin.

Also considered herein is a method of delivering a diagnostic/detection agent, a therapeutic agent, or a combination thereof to a target, comprising: (i) administering to a subject a multivalent, multispecific antibody or fragment thereof of the present invention; (ii) waiting a sufficient amount of time for an amount of the non-binding protein to clear the subject's blood stream; and (iii) administering to said subject a carrier molecule comprising a diagnostic/detection agent, a therapeutic agent, or a combination thereof, that binds to a binding site of said antibody. Preferably, the multivalent, multispecific antibody or fragment thereof comprises one or more antigen binding sites having affinity toward an AFP target antigen and one or more hapten binding sites having an affinity towards hapten molecules. Preferably, the carrier molecule binds to more than one binding site of the antibody. Also preferred, the diagnostic/detection agent or said therapeutic agent is selected from the group comprising isotopes, dyes, chromagens, contrast agents, drugs, toxins, cytokines, enzymes, enzyme inhibitors, hormones, hormone antagonists, growth factors, radionuclides, and metals.

Contemplated herein is a method of treating a malignancy in a subject comprising administering to said subject a therapeutically effective amount of (i) an antibody or fragment thereof or (ii) an antibody fusion protein or fragment thereof, wherein the antibody or fragment thereof comprises at least two MAbs or fragments thereof, at least one of which is any of the anti-AFP MAb or fragment thereof of the present invention, and the fusion protein or fragment thereof comprises at least one AFP binding site, formulated in a pharmaceutically suitable excipient. In a preferred embodiment, at least one of the Mabs or fragments thereof is a naked Mab or fragment thereof. In another embodiment, the fusion protein comprises a second binding site that is reactive with a tumor marker substance other than AFP. Also contemplated is that the anti-AFP antibody or fragment thereof, or anti-AFP fusion protein or fragment thereof, is administered before, concurrently, or after at least one therapeutic or diagnostic/detection agent.

Another embodiment is a method of treating a malignancy in a subject comprising administering to said subject a therapeutically effective amount of an antibody or fragment thereof comprising at least two MAbs or fragments thereof, wherein the MAbs are selected from any one of the anti-AFP antibodies described herein, and formulated in a pharmaceutically suitable excipient. In a preferred embodiment, at least one of the Mabs or fragments thereof is a naked Mab or fragment thereof. Also contemplated is that the anti-AFP antibody or fragment thereof, or anti-AFP fusion protein or fragment thereof, is administered before, concurrently, or after at least one therapeutic and/or diagnostic/detection agent.

In the method of treatment described herein, the anti-AFP antibody is selected from the group consisting of a subhuman primate anti-AFP antibody, murine monoclonal anti-AFP antibody, chimeric anti-AFP antibody, human anti-AFP antibody, and humanized anti-AFP antibody. Preferably, the chimeric, human and humanized anti-AFP antibody constant and hinge regions comprise constant and hinge regions of a human IgG1. Also in the methods described herein, the anti-AFP antibody or fragment thereof or fusion protein or fragment thereof is administered before, in conjunction with, or after a second conjugated antibody reactive with a second tumor marker expressed by said malignancy is administered to said subject.

The present invention also describes a method of diagnosing or detecting a malignancy in a subject comprising administering to said subject a diagnostically effective amount of a diagnostic/detecting conjugate comprising a anti-AFP MAb or fragment thereof or a fusion protein or fragment thereof of as described in the present invention, wherein the anti-AFP MAb or fragment thereof, or fusion protein or fragment thereof, is bound to at least one diagnostic/detection agent, formulated in a pharmaceutically suitable excipient.

Another embodiment of the present invention is a method of treating a cancer cell in a subject comprising (i) administering to said subject a therapeutically effective amount of a composition comprising a naked or conjugated anti-AFP MAb or fragment thereof or a naked or conjugated antibody fusion protein or fragment thereof, as described in the present invention, (ii) formulating said anti-AFP MAb or fragment thereof or antibody fusion protein or fragment thereof in a pharmaceutically suitable excipient. Preferably, the anti-AFP antibody, fusion protein, or fragment thereof is an Immu31 antibody, fusion protein, or fragment thereof. Optionally, the composition may further comprise a second naked or conjugated antibody or fragment thereof, or naked or conjugated antibody fusion protein or fragment thereof, that may or be an anti-AFP antibody, fusion protein or fragment thereof, or may bind a second tumor marker expressed by the malignancy. Also considered is that the anti-AFP antibody, antibody fusion protein, or fragment thereof, is administered before, in conjunction with, or after a second antibody, fusion protein, or fragment thereof is administered to said subject. The anti-AFP antibody may also be administered before, concurrently or after a therapeutic or diagnostic/detection agent.

The present invention also describes a method of diagnosing or detecting a malignancy in a subject comprising (i) performing an in vitro diagnosis assay on a specimen from the subject with a composition comprising an anti-AFP MAb or fragment thereof or an antibody fusion protein or fragment thereof described herein. Preferably the malignancy is a carcinoma expressing AFP, such as a hepatocellular carcinoma, a hepatoblastoma or a germ cell tumor. Also preferred, the in vitro diagnosis assay is selected from the group consisting of immunoassays, RT-PCR and immunohistochemistry. If the diagnostic assay is RT-PCR or immunoassays, the specimen is preferably body fluid or a tissue or cell population. If the diagnostic assay is immunohistochemistry or immunocytochemistry, the specimen is preferably a cell aliquot or a tissue.

In any of the methods of the present invention, the subject is preferably a mammal, such as a human or domestic pet.

Another embodiment of the present invention is a method of treating or identifying diseased tissues in a subject, comprising: (A) administering to said subject a bi-specific antibody or antibody fragment having at least one arm that specifically binds a diseased tissue-associated marker and at least one other arm that specifically binds a targetable conjugate, wherein said diseased tissue-associated marker is AFP; (B) optionally, administering to said subject a clearing composition, and allowing said composition to clear non-localized antibodies or antibody fragments from circulation; (C) administering to said subject a first targetable conjugate which comprises a carrier portion which comprises or bears at least one epitope recognizable by said at least one other arm of said bi-specific antibody or antibody fragment, and one or more conjugated therapeutic or diagnostic agents; and (D) when said therapeutic agent is an enzyme, further administering to said subject (i) a prodrug, when said enzyme is capable of converting said prodrug to a drug at the target site; or (ii) a drug which is capable of being detoxified in said subject to form an intermediate of lower toxicity, when said enzyme is capable of reconverting said detoxified intermediate to a toxic form, and, therefore, of increasing the toxicity of said drug at the target site, or (iii) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or (iv) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site. Preferably, at least one arm that specifically binds a targeted tissue is a human, chimeric or humanized Immu31 antibody or a fragment of a human, chimeric or humanized Immu31 antibody. Also preferred, the targetable conjugate comprises at least two HSG haptens. Preferably, the targeted tissue is a tumor and more preferably, the tumor produces or is associated with alpha-fetoprotein (AFP). Also preferred, the Immu31 antibody or fragment thereof comprises the Fv of MAb Immu31.

This method may further comprise, when said first targetable conjugate comprises a prodrug, administering a second targetable conjugate which comprises a carrier portion which comprises or bears at least one epitope recognizable by said at least one other arm of said bi-specific antibody or antibody fragment, and an enzyme capable of converting said prodrug to a drug or of reconverting a detoxified intermediate of said drug to a toxic form Preferably, the prodrug is selected from the group consisting of epirubicin glucuronide, CPT-11, etoposide glucuronide, daunomicin glucuronide and doxorubicin glucuronide. Also preferred, the targetable conjugate comprises one or more radioactive isotopes useful for killing diseased tissue. The targetable conjugate may comprise one or more agents for photodynamic therapy, such as a photosensitizer. In a preferred embodiment, the photosensitizer is selected from the group consisting of benzoporphyrin monoacid ring A (BPD-MA), tin etiopurpurin (SnET2), sulfonated aluminum phthalocyanine (AlSPc) and lutetium texaphyrin (Lutex).

Considered herein is a method for detecting or treating tumors expressing AFP in a mammal, comprising: (A) administering an effective amount of a bispecific antibody or antibody fragment comprising at least one arm that specifically binds a targeted tissue and at least one other arm that specifically binds a targetable conjugate, wherein said one arm that specifically binds a targeted tissue is an Immu31 antibody or fragment thereof, and (B) administering a targetable conjugate selected from the group consisting of (i) DOTA-Phe-Lys(HSG)-D-Tyr-Lys(HSG)-NH$_2$; (ii) DOTA-Phe-Lys(HSG)-Tyr-Lys(HSG)-NH$_2$ (SEQ ID NO: 7); (iii) Ac-Lys(HSG)D-Tyr-Lys(HSG)-Lys(Tscg-Cys)-NH$_2$;

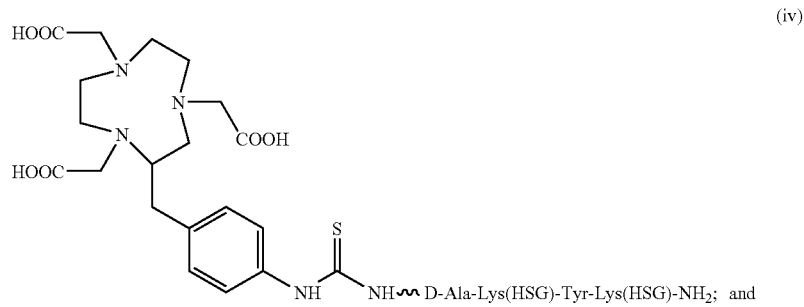

(iv)

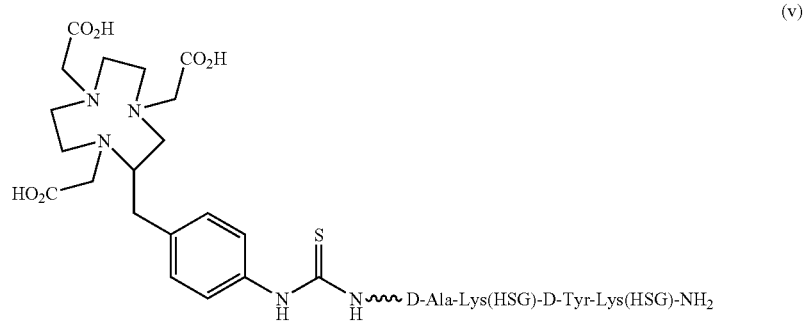

(v)

Preferably, the method further comprises administering to the subject a clearing composition, and allowing said composition to increase clearance of non-localized antibodies or antibody fragments from circulation.

Also contemplated herein is a kit useful for treating or identifying diseased tissues in a subject comprising: (A) a bi-specific antibody or antibody fragment having at least one arm that specifically binds a targeted tissue and at least one other arm that specifically binds a targetable conjugate, wherein said one arm that specifically binds a targeted tissue is an Immu31 antibody or fragment thereof; (B) a first targetable conjugate which comprises a carrier portion which comprises or bears at least one epitope recognizable by said at least one other arm of said bi-specific antibody or antibody fragment, and one or more conjugated therapeutic or diagnostic agents; and (C) optionally, a clearing composition useful for clearing non-localized antibodies and antibody fragments; and (D) optionally, when said therapeutic agent conjugated to said first targetable conjugate is an enzyme, (i) a prodrug, when said enzyme is capable of converting said prodrug to a drug at the target site; or (ii) a drug which is capable of being detoxified in said subject to form an intermediate of lower toxicity, when said enzyme is capable of reconverting said detoxified intermediate to a toxic form, and, therefore, of increasing the toxicity of said drug at the target site, or (iii) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or (iv) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site. Preferably, the targetable conjugate is selected from the group consisting of:

(i) DOTA-Phe-Lys(HSG)-D-Tyr-Lys(HSG)-$NH_2$;
(ii) DOTA-Phe-Lys(HSG)-Tyr-Lys(HSG)-$NH_2$ (SEQ ID NO: 7);
(iii) Ac-Lys(HSG)D-Tyr-Lys(HSG)-Lys(Tscg-Cys)-$NH_2$;

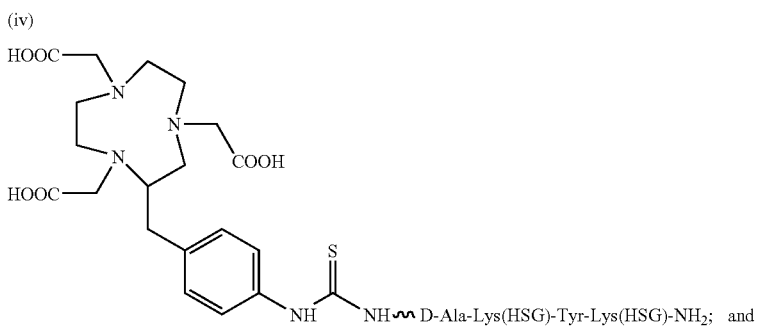

(iv)

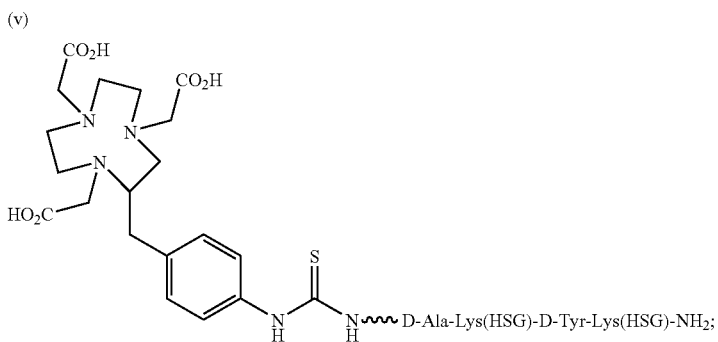

(v)

Also described in the present invention is a method of screening for a targetable conjugate comprising: (A) contacting said targetable construct with a bi-specific antibody or antibody fragment having at least one arm that specifically binds a marker associated with a targeted tissue, wherein said marker is AFP, and at least one other arm that specifically binds said targetable conjugate to give a mixture; and (B) optionally incubating the mixture; and (C) analyzing the mixture.

Another embodiment is a method for imaging malignant tissue or cells in a mammal expressing AFP, comprising: (A) administering an effective amount of a bispecific antibody or antibody fragment comprising at least one arm that specifically binds a marker associated with a targeted tissue and at least one other arm that specifically binds a targetable conjugate, wherein said marker is AFP; and (B) administering a targetable conjugate selected from the group consisting of (i) DOTA-Phe-Lys(HSG)-D-Tyr-Lys(HSG)-$NH_2$;
(ii) DOTA-Phe-Lys(HSG)-Tyr-Lys(HSG)-$NH_2$ (SEQ ID NO: 7);
(iii) Ac-Lys(HSG)D-Tyr-Lys(HSG)-Lys(Tscg-Cys)-$NH_2$;

(iv)

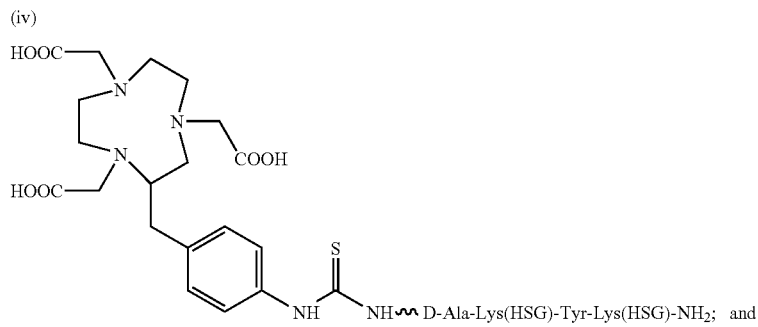

(v)

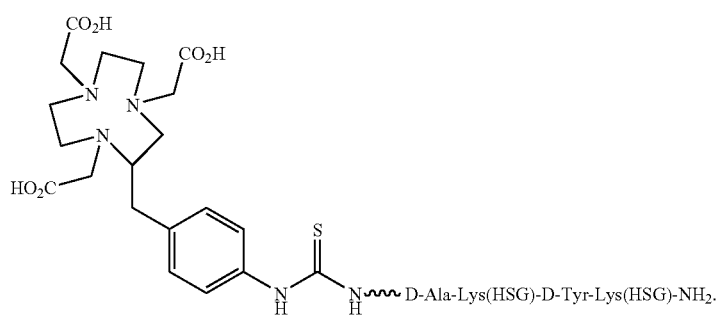

The invention also contemplates a method of intraoperatively identifying/disclosing diseased tissues expressing AFP, in a subject, comprising: (A) administering an effective amount of a bispecific antibody or antibody fragment comprising at least one arm that specifically binds AFP and at least one other arm that specifically binds a targetable conjugate, wherein said one arm that specifically binds a targeted tissue is an Immu31 antibody or fragment thereof; and (B) administering a targetable conjugate selected from the group consisting of (i) DOTA-Phe-Lys(HSG)-D-Tyr-Lys(HSG)-NH$_2$;
(ii) DOTA-Phe-Lys(HSG)-Tyr-Lys(HSG)-NH$_2$ (SEQ ID NO: 7);
(iii) Ac-Lys(HSG)D-Tyr-Lys(HSG)-Lys(Tscg-Cys)-NH$_2$;

(iv)

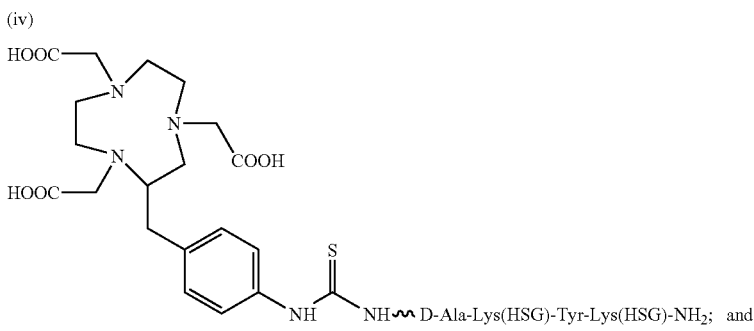

(v)

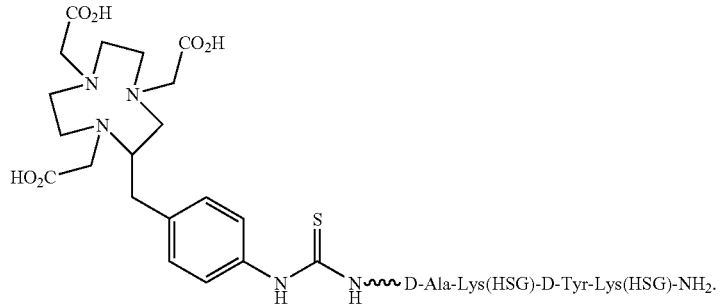

Also described herein is a method for the endoscopic identification of diseased tissues expressing AFP, in a subject, comprising: (A) administering an effective amount of a bispecific antibody or antibody fragment comprising at least one arm that specifically binds AFP and at least one other arm that specifically binds a targetable conjugate wherein said one arm that specifically binds a targeted tissue is a Immu31 antibody or fragment thereof; and (B) administering a targetable conjugate selected from the group consisting of
(i) DOTA-Phe-Lys(HSG)-D-Tyr-Lys(HSG)-NH$_2$;
(ii) DOTA-Phe-Lys(HSG)-Tyr-Lys(HSG)-NH$_2$ (SEQ ID NO: 7);
(iii) Ac-Lys(HSG)D-Tyr-Lys(HSG)-Lys(Tscg-Cys)-NH$_2$;

(iv)
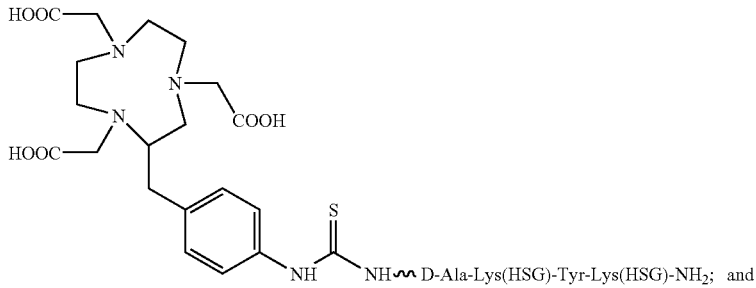

(v)
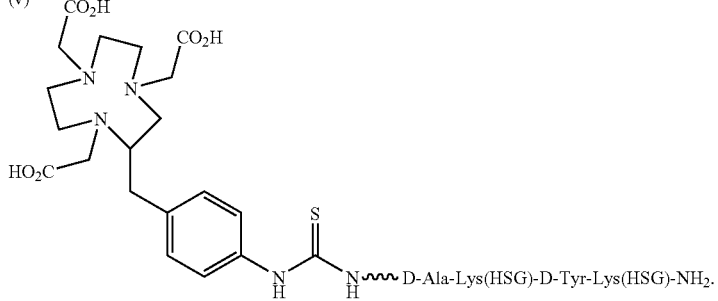

Another embodiment is a method for the intravascular identification of diseased tissues expressing AFP, in a subject, comprising: (A) administering an effective amount of a bispecific antibody or antibody fragment comprising at least one arm that specifically binds AFP and at least one other arm that specifically binds a targetable conjugate wherein said one arm that specifically binds a targeted tissue is a Immu31 antibody or fragment thereof; and (B) administering a targetable conjugate selected from the group consisting of
(i) DOTA-Phe-Lys(HSG)-D-Tyr-Lys(HSG)-NH$_2$;
(ii) DOTA-Phe-Lys(HSG)-Tyr-Lys(HSG)-NH$_2$ (SEQ ID NO: 7);
(iii) Ac-Lys(HSG)D-Tyr-Lys(HSG)-Lys(Tscg-Cys)-NH$_2$;

(iv)
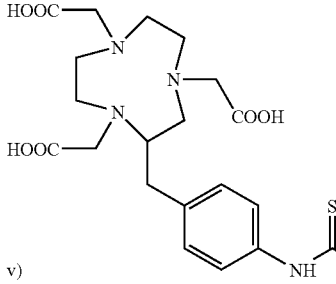

(v)
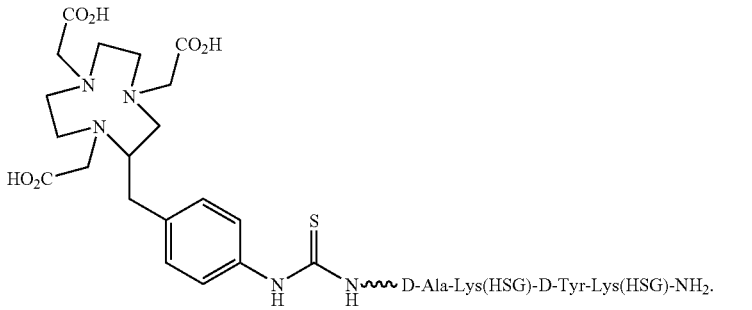

Another embodiment is a method of detecting lesions, preferably during an endoscopic, laparoscopic, intravascular catheter, or surgical procedure, wherein the method comprises: (A) injecting a subject who is to undergo such a procedure with a bispecific antibody F(ab)$_2$ or F(ab')$_2$ fragment, wherein the bispecific antibody or fragment has a first antibody binding site which specifically binds to a AFP antigen, and has a second antibody binding site which specifically binds to a hapten, and permitting the antibody fragment to accrete at target sites; (B) optionally clearing non-targeted antibody fragments using a galactosylated anti-idiotype clearing agent if the bispecific fragment is not largely cleared from circulation within about 24 hours of injection, and injecting a bivalent labeled hapten, which quickly localizes at the target site and clears through the kidneys; (C) detecting the presence of the hapten by close-range detection of elevated levels of accreted label at the target sites with detection means, within 48 hours of the first injection, and conducting said procedure, wherein said detection is performed without the use of a contrast agent or subtraction agent. In a preferred embodiment, the hapten is labeled with a diagnostic/detection radioisotope, a MRI image-enhancing agent or a fluorescent label.

Also considered is a method for close-range lesion detection, preferably during an operative, intravascular, laparoscopic, or endoscopic procedure, wherein the method comprises: (A) injecting a subject to such a procedure parenterally with an effective amount of an Immu31 immunoconjugate or fragment thereof, (B) conducting the procedure within 48 hours of the injection; (C) scanning the accessed interior of the subject at close range with a detection means for detecting the presence of said labeled antibody or fragment thereof; and (D) locating the sites of accretion of said labeled antibody or fragment thereof by detecting elevated levels of said labeled antibody or fragment thereof at such sites with the detection means. Preferably, the Immu31 immunoconjugate or fragment thereof comprises a radioisotope that emits at an energy of 20-1,000 keV Also preferred, the radioisotope is selected from the group consisting of technetium-99m, iodine-125, iodine-131, iodine-123, indium-111, fluorine-18, gallium 68 and gallium-67. In another embodiment, Immu31 immunoconjugate or fragment thereof comprises a non-isotopic agent, such as a photoactive agent.

BRIEF DESCRIPTION OF THE FIGURES

FIG. 1 shows the cloned V$_H$ and Vκ gene sequences of the murine Immu31 by RT-PCR and the deduced amino acid sequences. Underlined at 5'-ends are the PCR primer sequences used in cloning. Only the sequences of variable regions are shown, therefore, the 3'-end PCR primer sequences are not shown. FIG. 1A shows the DNA (SEQ ID NO: 30) and amino acid (SEQ ID NO: 31) sequences of the Immu31V$_H$. FIG. 1B shows the DNA (SEQ ID NO: 32) and amino acid (SEQ ID NO: 33) sequences of the Immu31Vκ. Amino acid sequences encoded by the corresponding DNA sequences are given as one letter codes below the nucleotide sequence. Numbering of the nucleotide sequence is on the right side. The amino acid residues in the CDR regions are shown in bold and underlined. Kabat's Ig molecule numbering is used for amino acid residues as shown by the numbering above the amino acid residues. The residues numbered by a letter following digits indicate the insertion residues defined by Kabat numbering scheme. The insertion residues numbered with a letter only have the same preceeding digits as the previous one. For example, residues 82, 82A, 82B and 82C in FIG. 1A are indicated as 82, A, B, and C, respectively.

FIG. 2 shows the DNA and amino acid sequences of the chimeric Immu31 (cImmu31) heavy and light chain variable regions expressed in Sp2/0 cells. FIG. 2A shows the DNA (SEQ ID NO: 34) and amino acid (SEQ ID NO: 35) sequences of the cImmu31V$_H$. FIG. 2B shows the DNA (SEQ ID NO: 36) and amino acid (SEQ ID NO: 37) sequences of the cImmu31Vκ. Amino acid sequences encoded by the corresponding DNA sequences are given as one letter codes. The amino acid residues in the CDR regions are shown in bold and underlined. Numbering of the nucleotide sequence is on the right side. The numbering of amino acids is same as that in FIG. 1. The restriction sites used for construction of the cImmu31 are boxed and indicated.

FIG. 4 shows the alignment of the amino acid sequences of light and heavy chain variable regions of the human antibodies, mouse Immu31 and hImmu31. FIG. 4A (SEQ ID NOS 38, 31 & 40, respectively, in order of appearance) shows the alignment of the V$_H$ sequences of EU, NEWM, Immu31, and hImmu31, and FIG. 4B shows the V$_K$ sequence alignment of REI, Immu31 and hImmu31 (SEQ ID NOS 43, 33 & 42, respectively, in order of appearance). Dots indicate the residues in Immu31 and hImmu31 that are identical to the corresponding residues in the human antibodies. Dashes indicate the gaps introduced into the sequences to facilitate the alignment. Boxed regions represent the CDR regions. Both N- and C-terminal residues (underlined) of hImmu31 are fixed by the staging vectors used. Kabat's Ig molecule numbering scheme is used as in FIG. 1A and FIG. 1B. FIG. 4C shows the sequence alignment of hImmu31 V$_K$ and the variants hImmu31V$_K$T69 and hImmu31V$_K$T39 (SEQ ID NOS 42 & 45-46, respectively, in order of appearance). Dots indicate the residues in hImmu31V$_K$T69 and hImmu31V$_K$T39 that are identical to the corresponding residues of hImmu31V$_K$.

FIG. 5 shows the DNA and amino acid sequences of the humanized Immu31 (hImmu31) heavy and light chain variable regions expressed in Sp2/0 cells. FIG. 5A shows the DNA (SEQ ID NO. 39) and amino acid (SEQ ID NO. 40) sequences of the hImmu31VH and FIG. 5B shows the DNA (SEQ ID NO. 41) and amino acid (SEQ ID NO. 42) sequences of the hImmu31Vκ. Amino acid sequences encoded by the corresponding DNA sequences are given as one letter codes. The amino acid residues in the CDR regions are shown in bold and underlined. Kabat's Ig molecule numbering scheme is used for amino acid residues as in FIG. 1A and FIG. 1B.

DETAILED DESCRIPTION OF THE INVENTION

1. Overview

Figure 3:
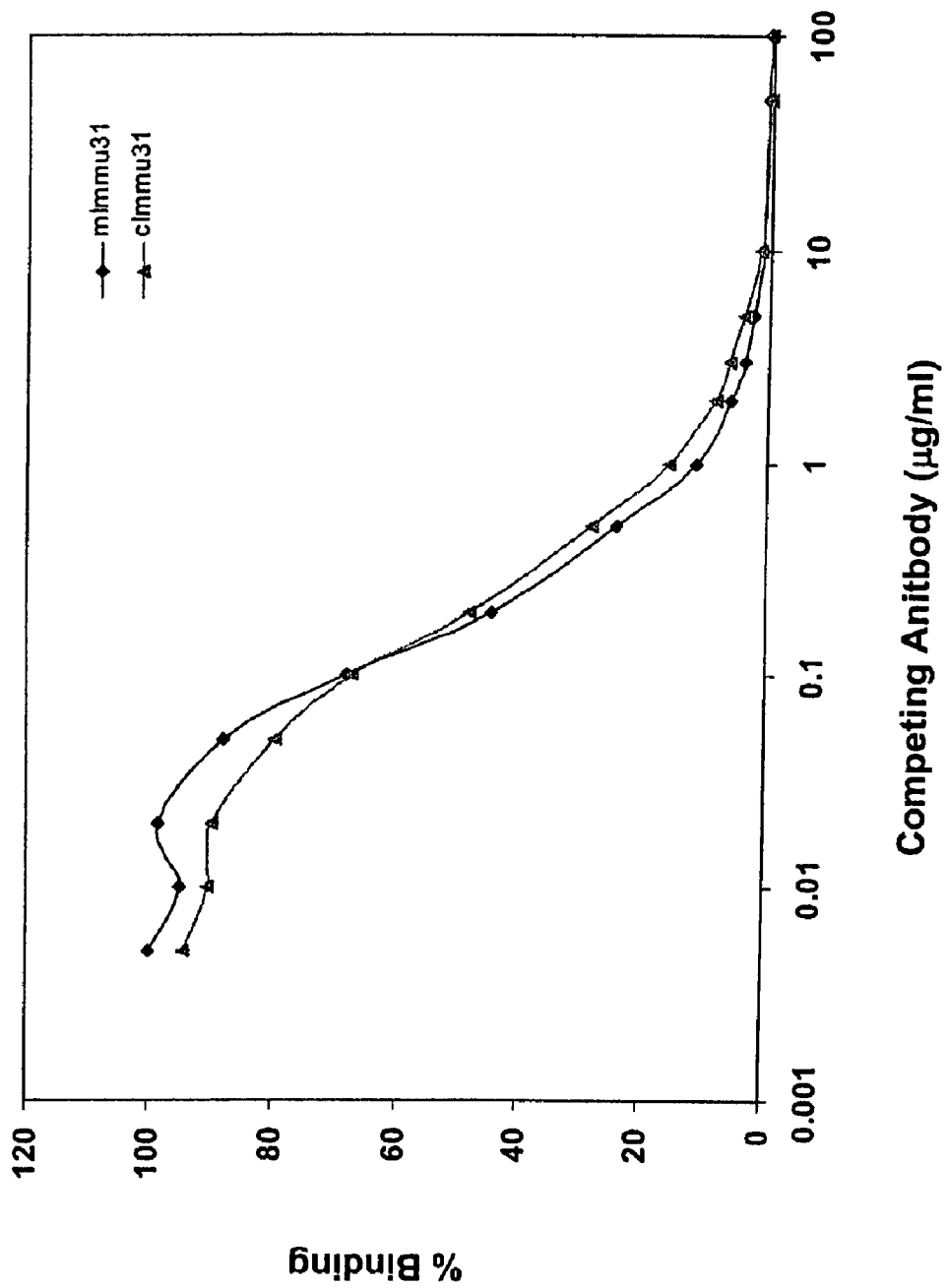
FIG. 3 shows the results of a competitive cell surface-binding assay to compare the binding affinity of cImmu31 with that of murine Immu31. Varying concentrations of cImmu31 (triangle line) or mImmu31 (diamond line) were mixed with a constant amount of biotinylated murine Immu31 and incubated for 1 h in the wells of 96-well ELISA plate precoated with AFP. After washing, HRP-conjugated streptavidin was added and incubated for 1 h at room temperature. The amount of HRP-conjugated streptavidin bound to the AFP-bound biotinylated Immu31 was revealed by reading OD$_{490}$ after the addition of a substrate solution containing 4 mM ortho-phenylenediamine dihydrochloride and 0.04% H$_2$O$_2$. The results showed that cImmu31 and the murine Immu31 competed equally well for the binding of radiolabeled Immu31 to AFP, confirming the cloned V genes are authentic.

The present invention provides murine, humanized, chimeric and human anti-alpha-fetoprotein (AFP) antibodies, fusion proteins, or fragments thereof useful for treatment and/or diagnosis of mammalian subjects, as an immunoconjugate or in combination with, but unconjugated to, other therapeutic and/or diagnostic agents. In a preferred embodiment, the anti-AFP antibody is an Immu31 antibody. The Immu31 antibodies and fragments thereof bind the alpha-fetoprotein antigen. As used herein, the phrase "Immu31" antibody or fragments means any antibody or fragment that binds the same epitope on the AFP antigen as an antibody or antibody fragment comprising CDR1 of a heavy chain variable region that comprises an amino acid sequence of SYVIH (SEQ ID NO: 4), CDR2 of a heavy chain variable region that comprises an amino acid sequence of YIHPYNGGT-KYNEKFKG (SEQ ID NO: 5), CDR3 of a heavy chain variable region that comprises an amino acid sequence of SGGGDPFAY (SEQ ID NO: 6), and CDR1 of a light chain variable region that comprises an amino acid sequence of KASQDINKYIG (SEQ ID NO: 1), CDR2 of a light chain variable region that comprises an amino acid sequence of YTSALLP (SEQ ID NO: 2), and CDR3 of a light chain variable region that comprises an amino acid sequence of LQYDDLWT (SEQ ID NO: 3).

The Immu31 antibodies, fusion proteins, and fragments thereof of the present invention may also be administered with another conjugated or unconjugated Immu31 antibody, fusion protein, or fragment thereof, or a conjugated or unconjugated non-Immu31 antibody, fusion protein, or fragment thereof.

The chimeric or humanized anti-AFP MAbs and fragments thereof of the present invention contain specific murine CDRs or a combination of murine CDRs from more than one murine or chimeric anti-AFP MAb. Preferably, the chimeric and humanized anti-AFP antibodies of the present invention contain CDRs from a muring Immu31 antibody. The Immu31 Mabs and fragments thereof of the present invention are murine, humanized, chimeric or fully human Mabs. The chimeric and humanized antibodies contain the amino acid sequence of the CDRs of a murine Immu31 (mImmu31) MAb and the light and heavy chain constant regions of a human antibody.

In a preferred embodiment, the humanized Immu31 MAb or fragment thereof of the present invention comprises the CDRs of a murine Immu31 MAb and the framework (FR) regions of the light and heavy chain variable regions of a human antibody and the light and heavy chain constant regions of a human antibody. Preferably, the CDRs of the light chain variable region of the humanized Immu31 MAb comprises CDR1 comprising amino acids KASQDINKYIG (SEQ ID NO: 1); CDR2 comprising amino acids YTSALLP (SEQ ID NO: 2); and CDR3 comprising amino acids LQY-DDLWT (SEQ ID NO: 3); and the CDRs of the heavy chain variable region of the Immu31 MAb comprises CDR1 comprising amino acids SYVIH (SEQ ID NO: 4); CDR2 comprising amino acids YIHPYNGGTKYNEKFKG (SEQ ID NO: 5) and CDR3 comprising amino acids SGGGDPFAY (SEQ ID NO: 6).

In another embodiment, the humanized Immu31 MAb or fragment thereof may further contain in the FRs of the light and heavy chain variable regions of the hImmu31 antibody, at least one amino acid from the corresponding FRs of the murine MAb. Specifically, the humanized Immu31 MAb or fragment thereof contains at least one amino acid residue 5, 27, 28, 30, 46, 48, 66, 67 and 94 of the murine heavy chain variable region of FIG. 5A, designated as hImmu31VH and of at least one amino acid residue 4, 39, 48, 49, 58, 69, 100 and 107 of the murine light chain variable region FIG. 5B, designated hImmu31Vk. One or more of the murine amino acid sequences can be maintained in the human FR regions of the light and heavy variable chains if necessary to maintain proper binding or to enhance binding to AFP. More preferably the humanized Immu31 MAb or fragment thereof of the present invention comprises the hImmu31VH of FIG. 5A and the hImmu31$V_K$ of FIG. 5B.

In a related vein, chimeric Immu31 (cImmu31) MAb or fragment thereof of the present invention comprises the CDRs of a murine Immu31 MAb and the FR regions of the light and heavy chain variable regions of the murine Immu31 MAb. In other words, the cImmu31 antibody comprises the Fvs of the parental murine (i.e., mImmu31) MAb, and the light and heavy chain constant regions of a human antibody, wherein the CDRs of the light chain variable region of the chimeric Immu31 MAb comprise CDR1 comprising amino acids KASQDINKYIG; CDR2 comprising amino acids YTSALLP; and CDR3 comprising amino acids LQYD-DLWT; and the CDRs of the heavy chain variable region of the chimeric Immu31 MAb comprise CDR1 comprising amino acids SYVIH; CDR2 comprising amino acids YIH-PYNGGTKYNEKFKG and CDR3 comprising SGGGDP-FAY.

More preferably the chimeric Immu31 MAb or fragment thereof comprises the complementarity-determining regions (CDRs) of a murine Immu31 MAb and the framework (FR) regions of the light and heavy chain variable regions of the murine Immu31 MAb and the light and heavy chain constant regions of a human antibody, wherein the CDRs and $FR^s$ of the heavy and light chain variable region of the chimeric Immu31 MAb comprise the sequence shown in FIGS. 2A and 2B, respectively, designated cImmu31VH and cImmu31 $V_K$.

The present invention also contemplates antibody fusion proteins or fragments thereof comprising at least two anti-AFP MAbs or fragments thereof. Preferably, the anti-AFP antibodies and fragments thereof are the Immu31 antibodies and fragments thereof of the present invention. Also preferred, the antibody fusion proteins of the present invention are composed of one anti-AFP MAb and one or more of the second MAbs to provide specificity to different antigens, and are described in more detail below. Likewise, the antibody fusion protein of the present invention can be used in combination with yet another antibody. For example, the antibody fusion protein can be used in combination therapy with another antibody, which can be administered before, after or concurrently with the fusion protein, and is reactive with an antigen selected from the group consisting of CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigenstenascin, an oncogene, an oncogene product, IL-6, IGF-1, IGFR-1, tumor angiogenesis antigens, such as vascular endothelium growth factor (VEGF), placental growth factor (PlGF), ED-B fibronectin, and other vascular growth factors, Ga 733, ferritin and acidic isoferritin (AIF) of primary hepatic carcinoma, or a combination thereof.

In another preferred embodiment, the anti-AFP antibody is an Immu31 antibody and the antibody fusion protein or fragment thereof of the present invention is also intended to encompass an antibody fusion protein or fragment thereof comprising at least one first Immu31 MAb or fragment thereof as described above and at least one second non-Immu31 MAb or fragment thereof. Preferably, the non-Immu31 antibody or fragment thereof is a carcinoma associated antibody. MOre preferably the carcinoma associated MAb is a MAb reactive with CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens tumor necrosis antigenstenascin, an oncogene an oncogene product, IL-6, IGF-1, IGFR-1, tumor angiogenesis antigens, such as vascular endothelium growth factor (VEGF), placental growth factor (PlGF), ED-B fibronectin, and other vascular growth factors, Ga 733, ferritin and acidic isoferritin (AIF) of primary hepatic carcinoma, or a combination thereof, and even an anti-AFP MAb that is different from the Immu31 MAb described herein.

The humanized, chimeric and human Immu31 antibody may possess enhanced affinity binding with the epitope as a result of CDR mutation and manipulation of the CDR and other sequences in the variable region to obtain a superior therapeutic agent for the treatment of hepatocellular carcinoma, hepatoblastoma, germ cell tumors, and other α-fetoprotein (AFP) producing tumors. Modification to the binding specificity, affinity or avidity of an antibody is known and described in WO 98/44001, as affinity maturation, and this application summarizes methods of modification and is incorporated in its entirety by reference.

It may also be desirable to modify the antibodies of the present invention to improve effector function, e.g., so as to enhance antigen-dependent cell-mediated cytotoxicity (ADCC) and/or complement dependent cytotoxicity (CDC) of the antagonist. One or more amino acid substitutions or the introduction of cysteine in the Fc region may be made, thereby improving internalization capability and/or increased complement-mediated cell killing and ADCC. See Caron et al., *J. Ex. Med.* 176:1191-1195 (1991) and Shopes, B. J. *Immunol.* 148:2918-2022 (1992), incorporated herein by reference in their entirety. An antibody fusion protein may be prepared that has dual Fc regions with both enhanced complement lysis and ADCC capabilites.

Another embodiment of the present invention is a DNA sequence comprising a nucleic acid encoding a MAb or fragment thereof selected from the group consisting
(a) an Immu31 MAb or fragment thereof as described herein,
(b) an antibody fusion protein or fragment thereof comprising at least of the Immu31 MAbs or fragments thereof of the present invention,
(c) an antibody fusion protein or fragment thereof comprising at least one first MAb or fragment thereof comprising an Immu31 MAb or fragment thereof as described herein and at least one second MAb or fragment thereof, other than the Immu31 MAb or fragment thereof described herein, and
(d) an antibody fusion protein or fragment thereof comprising at least one first MAb or fragment thereof comprising the Immu31 MAb or fragment thereof and at least one second MAb or fragment thereof, wherein the second MAb is a carcinoma associated MAb reactive with CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and other vascular growth factors, Ga 733, ferritin and acidic isoferritin (AIF) of primary hepatic carcinoma, or a combination thereof.

In a related vein, expression vectors comprising the DNA sequences are also considered herein. In the case of vectors for use in preparing the humanized, chimeric and human Immu31 MAbs or antibody fusion proteins thereof or fragments thereof, these vectors contain the coding sequences for the light and heavy chain constant regions and the hinge region of the human immunoglobulin, as well as the secretion signal peptide. These vectors additionally contain, where required, promoter/enhancer elements to initiate the Ig gene expression in the selected host cell, and a drug-resistant marker for selection of transfected cells. Vectors that are particularly useful in the present invention are DHFR (such as pdHL2) or GS-vector, particularly when used to express a chimeric, humanized or human antibody, such as an IgG, where the vector codes for the heavy and light chain constant regions and hinge region of IgG1. More preferably, the light and heavy chain constant regions and hinge region are from a human EUmyeloma immunoglobulin, where optionally at least one of the amino acid residues in the allotype positions is changed to that found in a different IgG1 allotype, and wherein optionally amino acid I253 of the heavy chain of EU (based on the EU numbering system) may be replaced with alanine. See Edelman et al., *Proc. Natl. Acad. Sci. USA* 63: 78-85 (1969), incorporated herein in its entirety by reference.

Host cells containing the DNA sequences encoding the Immu31 MAbs or fragments thereof or antibody fusion proteins or fragments thereof of the present invention or host cells containing the vectors that contain these DNA sequences are encompassed by the present invention. Particularly useful host cells are mammalian cells, and more specifically, myeloma cell lines, such as Sp2/0, YB2/0, NS0, and CHO, such as DG-44, as discussed in more detail below. Also useful for producing monoclonal antibodies and other fusion proteins is the PER.C6 human cell line.

Also encompassed by the present invention is the method of expressing a Immu31 MAb or fragment thereof or a Immu31 fusion protein or fragment thereof comprising: (a) transfecting a mammalian cell with a DNA sequence of encoding a Immu31 MAb or fragment thereof or an antibody fusion protein or fragments thereof, and (b) culturing the cell transfected with the DNA sequence that secretes the Immu31 or fragment thereof or Immu31 antibody fusion protein or fragment thereof. Known techniques may be used that include a selection marker on the vector so that host cells that express the MAbs and the marker can be easily selected.

The present invention also encompasses liver cell targeting diagnostic/detection or therapeutic immunoconjugates comprising an anti-AFP MAb or fragment thereof or an anti-AFP fusion protein or fragment thereof, that bind to the AFP expressing cell and is bound to at least one diagnostic/detection and/or at least one therapeutic agent.

In a preferred embodiment, the diagnostic/detection immunoconjugate comprises an Immu31 MAb or fragment thereof or an antibody fusion protein or fragment thereof, and at least one diagnostic/detection agent. Examples of diagnostic/detection agents include diverse labels, radionuclides, chelators, dyes, fluorescent compounds, chromagens, and other marker moieties. Radionuclides useful for positron emission tomography include, but are not limited to: F-18, Mn-51, Mn-52m, Fe-52, Co-55, Cu-62, Cu-64, Ga-68, As-72, Br-75, Br-76, Rb-82m, Sr-83, Y-86, Zr-89, Tc-94m, In-110, I-120, and I-124. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and Tl-201. Decay energies of useful gamma-ray emitting radionuclides are preferably 20-2000 keV, more preferably 60-600 keV, and most preferably 100-300 keV. The diagnostic agent of the present invention may also be a contrast agent such as manganese, iron or gadolinium.

Also preferred, the therapeutic immunoconjugate of the present invention comprises an Immu31 antibody or fragment thereof, or an Immu31 fusion protein or fragment thereof, and at least one therapeutic agent. Examples of therapeutic agents include a radioactive label, an immunomodulator, a hormone, a photoactive therapeutic agent, a cytotoxic agent, which may be a drug or a toxin, and a combination thereof. The drugs useful in the present invention are those drugs that possess the pharmaceutical property selected from the group consisting of antimitotic, alkylating, antimetabolite, antibiotic, alkaloid, antiangiogenic, apoptotic agents and combinations thereof. More specifically, these drugs are selected from the group consisting of nitrogen mustards, ethylenimine derivatives, alkyl sulfonates, nitrosoureas, triazenes, folic acid analogs, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, antagonists, endostatin, taxols, camptothecins, anthracyclines, taxanes, and their analogs, and a combination thereof. The toxins encompassed by the present invention are bacterial, plant, or animal toxins, such as those selected from the group consisting of ricin, abrin, alpha toxin, saporin, onconase, i.e., ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin.

Suitable immunomodulators for the present invention include cytokine, a stem cell growth factor, a lymphotoxin, a hematopoietic factor, a colony stimulating factor (CSF), an interferon (IFN), erythropoietin, thrombopoietin and a combination thereof. More specifically lymphotoxins, including tumor necrosis factor (TNF), hematopoietic factors, including interleukin (IL-1, IL-2, IL-3, IL-6, IL-10, IL-12, IL-18), colony stimulating factor, including granulocyte-colony stimulating factor (G-CSF) or granulocyte macrophage-colony stimulating factor (GM-CSF)), interferon, including interferons-α, -β or -γ, and stem cell growth factor, including designated "S1 factor."

Particularly useful therapeutic immunoconjugates comprise one or more radioactive labels that have an energy between 60 and 700 keV. Such radioactive labels include, but are not limited to $^{32}$P, $^{33}$P, $^{47}$Sc, $^{59}$Fe, $^{64}$Cu, $^{67}$Cu, $^{75}$Se, $^{77}$As, $^{89}$Sr, $^{90}$Y, $^{99}$Mo, $^{105}$Rh, $^{109}$Pd, $^{111}$Ag, $^{125}$I, $^{131}$I, $^{142}$Pr, $^{143}$Pr, $^{149}$Pm, $^{153}$Sm, $^{161}$Tb, $^{166}$Ho, $^{169}$Er, $^{177}$Lu, $^{186}$Re, $^{188}$Re, $^{189}$Re, $^{194}$Ir, $^{198}$Au, $^{199}$Au, $^{211}$Pb, $^{212}$Pb, $^{213}$Bi, $^{58}$Co, $^{67}$Ga, $^{80m}$Br, $^{99m}$Tc, $^{103m}$Rh, $^{109}$Pt, $^{111}$In, $^{119}$Sb, $^{125}$I, $^{161}$Ho, $^{189m}$Os, $^{192}$Ir, $^{152}$Dy, $^{211}$At, $^{212}$Bi, $^{223}$Ra, $^{219}$Rn, $^{215}$Po, $^{211}$Bi, $^{225}$Ac, $^{223}$Fr, $^{217}$At, 213Bi and $^{255}$Fm, and combinations thereof. Other useful therapeutic conjugates are photoactive therapeutic agent, such as a chromogen or dye.

The present invention particularly encompasses methods of treating hepatocellular carcinoma, hepatoblastoma, germ cell tumors, and other AFP-producing tumors in a subject, such as a mammal, including humans, domestic or companion pets, such as dogs and cats, comprising administering to the subject a therapeutically effective amount of an anti-AFP MAb or a fragment thereof of the present invention, formulated in a pharmaceutically acceptable vehicle. Preferably the anti-AFP antibody or fragment thereof is an Immu31 antibody or fragment thereof. This therapy utilizes a "naked antibody" that does not have a therapeutic agent bound to it. The administration of the "naked Immu31 antibody" can be supplemented by administering to the subject concurrently or sequentially a therapeutically effective amount of at least one other "naked antibody" that binds to or is reactive with another antigen on the surface of the target cell or that has other functions, such as effector functions in the Fc portion of the MAb, that is therapeutic and which is discussed herein. For example, preferred MAbs that can supplement the naked Immu31 antibody are humanized, chimeric, human or murine (in the case of non-human animals) carcinoma associated antibodies or fragments thereof. Such carcinoma associated antibodies or fragments thereof preferably are selected from the group consisting of a MAb reactive with CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and other vascular growth factors, Ga 733, ferritin and acidic isoferritin (AIF) of primary hepatic carcinoma, or a combination thereof.

Both the naked Immu31 antibody therapy alone or in combination with other naked MAbs or fragments thereof as discussed above can be further supplemented with the administration, either concurrently or sequentially, of a therapeutically effective amount of at least one therapeutic agent, formulated in a pharmaceutically acceptable vehicle. As discussed herein the therapeutic agent may comprises a cytotoxic agent, a radioactive label, an immunomodulator, a hormone, a photoactive therapeutic agent or a combination thereof, formulated in a pharmaceutically acceptable vehicle.

In another therapeutic method, both the naked Immu31 therapy alone or in combination with other naked MAbs, as discussed above, can be further supplemented with the administration, either concurrently or sequentially, of a therapeutically effective amount of at least one therapeutic immunoconjugate, described herein and formulated in a pharmaceutically acceptable vehicle. The therapeutic immunoconjugate comprises at least one humanized, chimeric, human or murine (for non-human subjects) MAb selected from the group consisting of a MAb reactive with CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and other vascular growth factors, Ga 733, ferritin and acidic isoferritin (AIF) of primary hepatic carcinoma, or a combination thereof. The therapeutic immunoconjugate may be conjugated to at least one therapeutic agent selected from the group consisting of a cytotoxic agent, a radioactive label, an immunomodulator, a hormone, a photoactive therapeutic agent or a combination thereof, formulated in a pharmaceutically acceptable vehicle.

As described herein the present invention particularly encompasses a method of treating a hepatocellular carcinoma, hepatoblastoma, germ cell tumors, and other AFP producing tumors in a subject comprising administering to a subject a therapeutically effective amount of an antibody fusion protein or fragment thereof comprising at least two anti-AFP MAbs or fragments thereof of the present invention or comprising at least one anti-AFP MAb or fragment thereof of the present invention and at least one carcinoma associated MAb. Preferably, the carcinoma associated antibody is selected from the group consisting of MAbs reactive with CEA, EGP-1, EGP-2, (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and against other vascular growth factors, Ga 733, ferritin and acidic isoferritin (AIF) of primary hepatic carcinoma, or a combination thereof. Preferably, the anti-AFP antibody or fragment thereof is an Immu31 antibody or fragment thereof.

This therapeutic method can further be supplemented with the administration to the subject concurrently or sequentially of a therapeutically effective amount of at least one therapeutic agent, formulated in a pharmaceutically acceptable vehicle, wherein the therapeutic agent is preferably a cytotoxic agent, a radioactive label, an immunomodulator, a hormone, a photo active therapeutic agent or a combination thereof, formulated in a pharmaceutically acceptable vehicle.

Further, the antibody fusion proteins and fragments thereof of the present invention can be administered to a subject concurrently or sequentially with a therapeutically effective amount of a therapeutic conjugate comprising at least one MAb bound to at least one therapeutic agent, wherein said MAb component of the conjugate preferably comprises at least one humanized, chimeric, human or murine (for non-human subjects) MAb selected from the group consisting of a MAb reactive with CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and other vascular growth factors, Ga 733, ferritin and acidic isoferritin (AIF) of primary hepatic carcinoma, or a combination thereof.

The antibody fusion protein itself may also be conjugated to at least one therapeutic agent. These therapeutic agents can be a combination of different recited agents or combinations of the same agents, such as two different therapeutic radioactive labels.

Also encompassed by the present invention is a method of diagnosing/detecting hepatocellular carcinoma, hepatoblastoma, germ cell tumors, and other AFP producing tumors in a subject comprising administering to the subject, such as a mammal, including humans and domestic and companion pets, such as dogs, cats, rabbits, guinea pigs, a diagnostic/detection immunoconjugate comprising an anti-AFP MAb or fragment thereof or an anti-AFP fusion protein or fragment thereof of the present invention that binds to the AFP expressing cell, wherein the anti-AFP MAb or fragment thereof or antibody fusion protein or fragment thereof is bound to at least one diagnostic/detection agent. The anti-AFP antibody, fusion protein, or fragment thereof is preferably an Immu31 antibody, fusion protein, or fragment thereof. Optionally, the diagnostic/detection immunoconjugate is formulated in a pharmaceutically acceptable vehicle. The useful diagnostic agents are described herein.

2. Definitions

In the description that follows, a number of terms are used and the following definitions are provided to facilitate understanding of the present invention.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as $F(ab')_2$, $F(ab)_2$, Fab', Fab, Fv, sFv and the like. Regardless of structure, an antibody fragment binds with the same antigen that is recognized by the intact antibody. For example, an anti-AFP monoclonal antibody fragment binds with an epitope of AFP. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

A naked antibody is generally an entire antibody which is not conjugated to a therapeutic agent. This is so because the Fc portion of the antibody molecule provides effector functions, such as complement fixation and ADCC (antibody dependent cell cytotoxicity), which set mechanisms into action that may result in cell lysis. Naked antibodies include both polyclonal and monoclonal antibodies, as well as certain recombinant antibodies, such as chimeric, humanized or human antibodies. However, it is possible that the Fc portion is not required for therapeutic function, rather an antibody exerts its therapeutic effect through other mechanisms, such as induction of cell cycle resting and apoptosis. In this case, naked antibodies also include the unconjugated antibody fragments defined above.

A chimeric antibody is a recombinant protein that contains the variable domains including the complementarity determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domains of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A fully human antibody also can be constructed by genetic or chromosomal transfection methods, as well as phage display technology, all of which are known in the art. See for example, McCafferty et al., *Nature* 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, *Current Opinion in Structural Biology* 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

A diagnostic agent is a molecule or atom which is administered conjugated to an antibody moiety, i.e., antibody or antibody fragment, or subfragment, and is useful in diagnosing a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g. paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An immunomodulator is a therapeutic agent as defined in the present invention that when present, typically stimulates immune cells to proliferate or become activated in an immune response cascade, such as macrophages, B-cells, and/or T cells. An example of an immunomodulator as described herein is a cytokine. As the skilled artisan will understand, certain interleukins and interferons are examples of cytokines that stimulate T cell or other immune cell proliferation.

An expression vector is a DNA molecules comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as an transgenic animal, that have been genetically engineered to contain the cloned gene(s) in the chromosome or genome of the host cell or cells of the host cells. Suitable mammalian host cells include myeloma cells, such as SP2/0 cells, and NS0 cells, as well as Chinese Hamster Ovary (CHO) cells, hybridoma cell lines and other mammalian host cell useful for expressing antibodies. Also particularly useful to express MAbs and other fusion proteins, is a human cell line, PER.C6 disclosed in WO 0063403 A2, which produces 2 to 200-fold more recombinant protein as compared to conventional mammalian cell lines, such as CHO, COS, Vero, Hela, BHK and SP2-cell lines. Special transgenic animals with a modified immune system are particularly useful for making fully human antibodies.

As used herein, the term antibody fusion protein is a recombinantly produced antigen-binding molecule in which two or more of the same or different natural antibody, single-chain antibody or antibody fragment segments with the same or different specificities are linked. An anti-AFP fusion protein comprises an alpha-fetoprotein binding site. Preferably, the anti-AFP fusion protein is an Immu31 fusion protein. The Immu31 fusion protein and fragment thereof of the present invention comprise at least one arm that binds to the same AFP epitope an antibody or antibody fragment comprising CDR1 of a heavy chain variable region that comprises an amino acid sequence of SYVIH (SEQ ID NO: 4), CDR2 of a heavy chain variable region that comprises an amino acid sequence of YIHPYNGGTKYNEKFKG (SEQ ID NO: 5), CDR3 of a heavy chain variable region that comprises an amino acid sequence of SGGGDPFAY (SEQ ID NO: 6), and CDR1 of a light chain variable region that comprises an amino acid sequence of KASQDINKYIG (SEQ ID NO: 1), CDR2 of a light chain variable region that comprises an amino acid sequence of YTSALLP (SEQ ID NO: 2), and CDR3 of a light chain variable region that comprises an amino acid sequence of LQYDDLWT (SEQ ID NO: 3).

Valency of the fusion protein indicates the total number of binding arms or sites the fusion protein has to antigen(s) or epitope(s); i.e., monovalent, bivalent, trivalent or multivalent. The multivalency of the antibody fusion protein means that it can take advantage of multiple interactions in binding to an antigen, thus increasing the avidity of binding to the antigen, or to different antigens. Specificity indicates how many different types of antigen or epitope an antibody fusion protein is able to bind; i.e., monospecific, bispecific, trispecific, multispecific. Using these definitions, a natural antibody, e.g., an IgG, is bivalent because it has two binding arms but is monospecific because it binds to one type of antigen or epitope. A monospecific, multivalent fusion protein has more than one binding site for the same antigen or epitope. For example, a mono specific diabody is a fusion protein with two binding sites reactive with the same antigen. The fusion protein may comprise a multivalent or multispecific combination of different antibody components or multiple copies of the same antibody component. The fusion protein may additionally comprise a therapeutic agent. Examples of therapeutic agents suitable for such fusion proteins include immunomodulators ("antibody-immunomodulator fusion protein") and toxins ("antibody-toxin fusion protein"). One preferred toxin comprises a ribonuclease (RNase), preferably a recombinant RNase.

A multispecific antibody is an antibody that can bind simultaneously to at least two targets that are of different structure, e.g., two different antigens, two different epitopes on the same antigen, or a hapten and an antigen or epitope. One specificity would be for, for example, a B-cell, T-cell, myeloid-, plasma-, or mast-cell antigen or epitope. Another specificity could be to a different antigen on the same cell type, such as CD20, CD19, CD21, CD23, CD46, CD80, HLA-DR, CD74, or CD22 on B-cells. Multispecific, multivalent antibodies are constructs that have more than one binding site, and the binding sites are of different specificity. For example, a bispecific diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to, for example, a B-cell, T-cell, myeloid-, plasma-, and mast-cell antigen or epitope and at least one other arm that specifically binds to a targetable conjugate that bears a therapeutic or diagnostic agent. A variety of bispecific fusion proteins can be produced using molecular engineering. In one form, the bispecific fusion protein is divalent, consisting of, for example, a scFv with a single binding site for one antigen and a Fab fragment with a single binding site for a second antigen. In another form, the bispecific fusion protein is tetravalent, consisting of, for example, an IgG with two binding sites for one antigen and two identical scFv for a second antigen.

Caninized or felinized antibodies are recombinant proteins in which rodent (or another species) complementarity determining regions of a monoclonal antibody (MAb) have been transferred from heavy and light variable chains of rodent (or another species) immunoglobulin into a dog or cat, respectively, immunoglobulin variable domain.

Domestic animals include large animals such as horses, cattle, sheep, goats, llamas, alpacas, and pigs, as well as companion animals. In a preferred embodiment, the domestic animal is a horse.

Companion animals include animals kept as pets. These are primarily dogs and cats, although small rodents, such as guinea pigs, hamsters, rats, and ferrets, are also included, as are subhuman primates such as monkeys. In a preferred embodiment the companion animal is a dog or a cat.

3. Preparation of Monoclonal Antibodies Including Chimeric, Humanized and Human Antibodies Monoclonal antibodies (MAbs) are a homogeneous population of antibodies to a particular antigen and the antibody comprises only one type of antigen binding site and binds to only one epitope on an antigenic determinant. Rodent monoclonal antibodies to specific antigens may be obtained by methods known to those skilled in the art. See, for example, Kohler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991) [hereinafter "Coligan"]. Briefly, monoclonal antibodies can be obtained by injecting mice with a composition comprising an antigen, verifying the presence of antibody production by removing a serum sample, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Abs to peptide backbones are generated by well-known methods for Ab production. For example, injection of an immunogen, such as (peptide)$_n$-KLH, wherein KLH is keyhole limpet hemocyanin, and n=1-30, in complete Freund's adjuvant, followed by two subsequent injections of the same immunogen suspended in incomplete Freund's adjuvant into immunocompetent animals. The animals are given a final i.v. boost of antigen, followed by spleen cell harvesting three days later. Harvested spleen cells are then fused with Sp2/0-Ag14 myeloma cells and culture supernatants of the resulting clones analyzed for anti-peptide reactivity using a direct-binding ELISA. Fine specificity of generated Abs can be analyzed for by using peptide fragments of the original immunogen. These fragments can be prepared readily using an automated peptide synthesizer. For Ab production, enzyme-deficient hybridomas are isolated to enable selection of fused cell lines. This technique also can be used to raise antibodies to one or more of the chelates comprising the linker, e.g., In(III)-DTPA chelates. Monoclonal mouse antibodies to an In(III)-di-DTPA are known (Barbet '395 supra).

After the initial raising of antibodies to the immunogen, the variable genes of the monoclonal antibodies can be cloned from the hybridoma cells, sequenced and subsequently prepared by recombinant techniques. Humanization and chimerization of murine antibodies and antibody fragments are well known to those skilled in the art. For example, humanized monoclonal antibodies are produced by transferring mouse complementary determining regions from heavy and light variable chains of the mouse immunoglobulin into a human variable domain, and then, substituting human residues in the framework regions of the murine counterparts. In a preferred embodiment, some human residues in the framework regions of the humanized anti-AFP antibody or fragments thereof are replaced by their murine counterparts. Preferably, the humanized anti-AFP antibody is a humanized Immu31 antibody. It is also preferred that a combination of framework sequences from 2 different human antibodies are used for $V_H$. Still preferred, the two human antibodies are EU and NEWM. The constant domains of the antibody molecule is derived from those of a human antibody. The use of antibody components derived from humanized monoclonal antibodies obviates potential problems associated with the immunogenicity of murine constant regions.

General techniques for cloning murine immunoglobulin variable domains are described, for example, by the publication of Orlandi et al., *Proc. Nat'l Acad. Sci. USA* 86: 3833 (1989), which is incorporated by reference in its entirety. Techniques for constructing chimeric antibodies are well known to those of skill in the art. As an example, Leung et al., *Hybridoma* 13:469 (1994), describe how they produced an LL2 chimera by combining DNA sequences encoding the $V_K$ and $V_H$ domains of LL2 monoclonal antibody, an anti-CD22 antibody, with respective human $_K$ and $IgG_1$ constant region domains. This publication also provides the nucleotide sequences of the LL2 light and heavy chain variable regions, $V_K$ and $V_H$, respectively. Techniques for producing humanized MAbs are described, for example, by Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J Immun.* 150: 2844 (1993), each of which is hereby incorporated by reference.

Another method for producing the antibodies of the present invention is by production in the milk of transgenic livestock. See, e.g., Colman, A., *Biochem. Soc. Symp.*, 63: 141-147, 1998; U.S. Pat. No. 5,827,690, both of which are incorporated in their entirety by reference. Two DNA constructs are prepared which contain, respectively, DNA segments encoding paired immunoglobulin heavy and light chains. The DNA segments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

A chimeric antibody is a recombinant protein that contains the variable domains including the CDRs derived from one species of animal, such as a rodent antibody, while the remainder of the antibody molecule; i.e., the constant domains, is derived from a human antibody. Accordingly, a chimeric monoclonal antibody (MAb) can also be humanized by replacing the sequences of the murine FR in the variable domains of the chimeric MAb with one or more different human FR. Specifically, mouse CDRs are transferred from heavy and light variable chains of the mouse immunoglobulin into the corresponding variable domains of a human antibody. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Further, the affinity of humanized, chimeric and human MAbs to a specific epitope can be increased by mutagenesis of the CDRs, so that a lower dose of antibody may be as effective as a higher dose of a lower affinity MAb prior to mutagenesis. See for example, WO0029584A1.

A fully human antibody of the present invention, i.e., a human anti-AFP MAb or another human antibody, such as anti-CEA, anti-TAG-72, anti-Tn, anti-Le(y), anti-MUC1, anti-MUC2, anti-MUC3, anti-MUC4, anti-EGFR, anti-HER2 and anti-TNF (tumor necrosis factor) used for combination therapy with humanized or chimeric Immu31 antibodies, can be obtained from a transgenic non-human animal. See, e.g., Mendez et al., *Nature Genetics*, 15: 146-156 (1997) and U.S. Pat. No. 5,633,425, which are incorporated in their entirety by reference. For example, a human antibody can be recovered from a transgenic mouse possessing human immunoglobulin loci. Preferably, the anti-APP antibody is an Immu31 antibody. The mouse humoral immune system is humanized by inactivating the endogenous immunoglobulin genes and introducing human immunoglobulin loci. The human immunoglobulin loci are exceedingly complex and comprise a large number of discrete segments which together occupy almost 0.2% of the human genome. To ensure that transgenic mice are capable of producing adequate repertoires of antibodies, large portions of human heavy- and light-chain loci must be introduced into the mouse genome. This is accomplished in a stepwise process beginning with the formation of yeast artificial chromosomes (YACs) containing either human heavy- or light-chain immunoglobulin loci in germline configuration. Since each insert is approximately 1 Mb in size, YAC construction requires homologous recombination of overlapping fragments of the immunoglobulin loci. The two YACs, one containing the heavy-chain loci and one containing the light-chain loci, are introduced separately into mice via fusion of YAC-containing yeast spheroblasts with mouse embryonic stem cells. Embryonic stem cell clones are then microinjected into mouse blastocysts. Resulting chimeric males are screened for their ability to transmit the YAC through their germline and are bred with mice deficient in murine antibody production. Breeding the two transgenic strains, one containing the human heavy-chain loci and the other containing the human light-chain loci, creates progeny which produce human antibodies in response to immunization.

Unrearranged human immunoglobulin genes also can be introduced into mouse embryonic stem cells via microcell-mediated chromosome transfer (MMCT). See, e.g., Tomizuka et al., *Nature Genetics*, 16: 133 (1997). In this methodology microcells containing human chromosomes are fused with mouse embryonic stem cells. Transferred chromosomes are stably retained, and adult chimeras exhibit proper tissue-specific expression.

As an alternative, an antibody or antibody fragment of the present invention may be derived from human antibody fragments isolated from a combinatorial immunoglobulin library. See, e.g., Barbas et al., *METHODS: A Companion to Methods in Enzymology* 2: 119 (1991), and Winter et al., *Ann. Rev. Immunol.* 12: 433 (1994), which are incorporated by reference. Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

Further, recent methods for producing bispecific MAbs include engineered recombinant MAbs which have additional cysteine residues so that they crosslink more strongly than the more common immunoglobulin isotypes. See, e.g., FitzGerald et al., *Protein Eng.* 10(10):1221-1225, 1997. Another approach is to engineer recombinant fusion proteins linking two or more different single-chain antibody or antibody fragment segments with the needed dual specificities. See, e.g., Coloma et al., *Nature Biotech.* 15:159-163, 1997. A variety of bispecific fusion proteins can be produced using molecular engineering. In one form, the bispecific fusion protein is monovalent, consisting of, for example, a scFv with a single binding site for one antigen and a Fab fragment with a single binding site for a second antigen. In another form, the bispecific fusion protein is divalent, consisting of, for example, an IgG with two binding sites for one antigen and two scFv with two binding sites for a second antigen.

Bispecific fusion proteins linking two or more different single-chain antibodies or antibody fragments are produced in similar manner. Recombinant methods can be used to produce a variety of fusion proteins. For example a fusion protein comprising a Fab fragment derived from a humanized monoclonal Immu31 antibody and a scFv derived from a murine anti-di-DTPA can be produced. A flexible linker, such as GGGS (SEQ ID NO: 47) connects the scFv to the constant region of the heavy chain of the Immu31 antibody. Alternatively, the scFv can be connected to the constant region of the light chain of another humanized antibody. Appropriate linker sequences necessary for the in-frame connection of the heavy chain Fd to the scFv are introduced into the VL and Vκ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the VH region of an Immu31 antibody. The resulting vector can be used to transfect an appropriate host cell, such as a mammalian cell for the expression of the bispecific fusion protein.

4. Preparation of Chimeric, Humanized and Human Anti-aFP Antibodies

Cell lines and culture media used in the present invention include Immu31 hybridoma cells and Sp2/0-Ag14 myeloma cells (ATCC, Rockville, Md.). The monoclonal hybridoma producing Immu31 was obtained by fusing the spleen cells prepared from a mouse that had been immunized with alpha-fetoprotein with SP2/0Ag14. These cells may be cultured in Hybridoma serum-free media (HSFM) (Life Technologies, Grand Island, N.Y.) supplemented with 10% fetal bovine serum (FBS) (Hyclone Laboratories, Logan, Utah) and antibiotics (complete media). Alternatively, they may be cultured in Dulbecco's modified Eagle's Medium (DMEM) supplemented with 10% FCS (Gibco/BRL, Gaithersburg, Mass.) containing 10% of FCS and 75 µg/ml gantamicin (complete HSFM) or, where indicated, in HSFM containing only antibiotics. Selection of the transfectomas may be carried out in complete HSFM containing 500 units/ml of hygromycin (Calbiochem, San Diego, Calif.). All cell lines are preferably maintained at 37° C. in 5% $CO_2$.

Obtaining Vκ and $V_H$ Gene Segments

Isolation of the Vκ and $V_H$ gene segments can be accomplished by several means that are well-known in the art. Two such means include, but are not limited to, PCR cloning and cDNA library screening.

PCR cloning techniques are well-known in the art. In brief, however, PCR cloning of $V_\kappa$ and $V_H$ gene fragments maybe accomplished as follows. Total RNA may be isolated from a Immu31 hybridoma cell line using commercially available kits such as the Fast Track RNA Isolation kit (Invitrogen, San Diego, Calif.). The first strand cDNA may then be reverse transcribed from RNA using a cDNA cycle kit (Invitrogen). In this process, 5 µg of total RNA is annealed to an oligo dT or random hexamer primer, or a murine IgG CH1-specific primer or a murine Ck-specific primer. Examples of such primers include CH1B (5'-ACA GTC ACT GAG CTG G-3') (SEQ ID NO: 8) and Ck3-BH1 (5'-GCC GGA TCC TGA CTG GAT GGT GGG AAG ATG GAT ACA-3') (SEQ ID NO: 9), respectively. The first strand cDNA may be used as templates to amplify the $V_H$ and Vκ sequences by PCR, as described by Orlandi et al. For the Vκ region, a primer pair such as VK1BACK (5'-GAC ATT CAG CTG ACC CAG TCT CCA-3') (SEQ ID NO: 10) and IgKC3' (5'-CTC ACT GGA TGG TGG GAA GAT GGA TAC AGT TGG-3') (SEQ ID NO: 11) may be used. For the $V_H$ region, a primer pair such as VH1BACK (5'-AGG T(C/G)(A/C) A(A/G)C TGC AG(C/G) AGT C(A/T)G G-3') (SEQ ID NO: 12) and CH1B may be used. After amplification, the Vκ and $V_H$ fragments may then be gel-purified and cloned into a cloning vector such as the TA cloning vector (Invitrogen) for sequence analyses by the dideoxytermination method. Sequences confirmed to be of immunoglobulin origin may then be used to construct chimeric Ab expression vectors using methods described by Leung et al. (Hybridoma, 13:469 (1994)).

As a preferred alternative to isolating the VK and $V_H$ gene segments by PCR cloning, cDNA library screening may be utilized. cDNA screening methods also are well known in the art. In brief, however, a cDNA library may be constructed from the mRNA extracted from the murine Immu31 hybridoma cells in pSPORT vector (Life Technologies). The first strand cDNA may be synthesized by priming ply A RNA from Immu31 hybridoma with an oligo dT primer-NotI adaptor (Life Technologies). After the second strand synthesis and attachment of SalI adaptors, the cDNA pool may be size fractionated through a cDNA size fractionation column. Fractionated cDNA may then be ligated to pSPORT vector and subsequently transformed into *Escherichia coli* DH5α. A library may then be plated, transferred to filters, and amplified.

Screening of the cDNA library may be accomplished by hybridization with labeled probes specific for the heavy and light chains. For example [32-P]-labeled probes such as MUCH-1 (5'-AGA CTG CAG GAG AGC TGG GAA GGT GTG CAC-3') (SEQ ID NO: 13) for heavy chain and MUCK-1 (5'-GAA GCA CAC GAC TGA GGC ACC TCC AGA TGT-3') (SEQ ID NO: 14) for light chain. Clones that are positive on a first screening may be transferred to duplicate plates and screened a second time with the same probes.

RNA isolation, cDNA synthesis, and amplification can be carried out as follows. Total cell RNA can be prepared from a Immu31 hybridoma cell line, using a total of about $10^7$ cells, according to Sambrook et al., (Molecular Cloning: A Laboratory Manual, Second ed., Cold Spring Harbor Press, 1989), which is incorporated by reference. First strand cDNA can be reverse transcribed from total RNA conventionally, such as by using the SuperScript preamplification system (Gibco/BRL, Gaithersburg, Md.). Briefly, in a reaction volume of 20 μl, 50 ng of random hexamer primers can be annealed to 5 μg of RNAs in the presence of 2 μl of 10× synthesis buffer [200 mM Tris-HCl (pH 8.4), 500 mM KCl, 25 mM $MgCl_2$, 1 mg/ml BSA], 1 μl of 10 mM dNTP mix, 2 μl of 0.1 M DTT, and 200 units of SuperScript reverse transcriptase. The elongation step is initially allowed to proceed at room temperature for 10 min followed by incubation at 42° C. for 50 min. The reaction can be terminated by heating the reaction mixture at 90° C. for 5 min.

Synthesizing and labeling the screening probes can be accomplished by well-known means. Depending on the detection systems utilized, probe labeling will vary. Many kits for this purpose are commercially available. One method for 32-P labeling of oligonucleotides includes the use of with [γ-$^{32}$P]ATP (Amersham Arlington Heights, Ill.) and T4 polynucleotide kinase (New England Biolabs, Beverly, Mass.), followed by column purification.

Preparation of a Chimeric Anti-Afp Antibody

In general, to prepare chimeric anti-AFP MAb, $V_H$ and V κchains of a AFP antibody may be obtained by methods such as those described above and amplified by PCR. In a preferred embodiment, the chimeric anti-AFP antibody is a Immu31 antibody. The Vκ PCR products may be subcloned into a pBR327 based staging vector (VKpBR) as described by Leung et al., Hybridoma, 13:469 (1994). The $V_H$ PCR products may be subcloned into a similar pBluescript-based staging vector (VHpBS). The fragments containing the Vκ and $V_H$ sequences, along with the promoter and signal peptide sequences, can be excised from the staging vectors using HindIII and BamHI restriction endonucleases. The Vκ fragments (about 600 bp) can be subcloned into a mammalian expression vector (for example, pKh) conventionally. pKh is a pSVhyg-based expression vector containing the genomic sequence of the human kappa constant region, an Ig enhancer, a kappa enhancer and the hygromycin-resistant gene. Similarly, the about 800 bp $V_H$ fragments can be subcloned into pG1g, a pSVgpt-based expression vector carrying the genomic sequence of the human IgG1 constant region, an Ig enhancer and the xanthine-guanine phosphoribosyl transferase (gpt) gene. The two plasmids may be co-transfected into mammalian cells, such as Sp2/0-Ag14 cells, by electroporation and selected for hygromycin resistance. Colonies surviving selection are expanded, and supernatant fluids monitored for production of cImmu31 MAb by an ELISA method. A transfection efficiency of about $1-10 \times 10^6$ cells is desirable. An antibody expression level of between 0.10 and 2.5 μg/m$^1$ can be expected with this system.

Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al. *J Immunol. Methods* 125:191 (1989), Losman et al., *Clin. Cancer Res.* 5:3101 (1999) and in Losman et al., *Cancer,* 80:2660 (1997) for the expression in Sp2/0-Ag 14 cells. Another vector that is useful in the present invention is the GS-vector, as described in Barnes et al., *Cytotechnology* 32:109-123 (2000), which is preferably expressed in the NS0 cell line and CHO cells. Other appropriate mammalian expression systems are described in Werner et al., Arzneim.-Forsch./Drug Res. 48(II), Nr. 8, 870-880 (1998).

Preparation of a Humanized Anti-Afp Antibody

In a preferred embodiment, the humanized anti-AFP antibody is a humanized Immu31 antibody. Once the sequences for the hImmu31 Vκ and $V_H$ domains are designed, CDR engrafting can be accomplished by gene synthesis using long synthetic DNA oligonucleotides as templates and short oligonucleotides as primers in a PCR reaction. In most cases, the DNA encoding the Vκ or $V_H$ domain will be approximately 350 bp long. By taking advantage of codon degeneracy, a unique restriction site may easily be introduced, without changing the encoded amino acids, at regions close to the middle of the V gene DNA sequence. For example, at DNA nucleotide positions 169-174 (amino acid positions 56-57) for the hImmu31 VH domain, a unique KpnI site can be introduced while maintaining the originally designed amino acid sequence (see the sequence in FIG. 5A). Two long non-overlapping single-stranded DNA oligonucleotides (~150 bp) upstream and downstream of the KpnI site can be generated by automated DNA oligonucleotide synthesizer (Cyclone Plus DNA Synthesizer, Milligen-Biosearch). As the yields of full length DNA oligonucleotides may be expected to be low, they can be amplified by two pairs of flanking oligonucleotides in a PCR reaction. The primers can be designed with the necessary restriction sites to facilitate subsequent sequence assembly and subcloning. Primers for the oligonucleotides should contain overlapping sequence at the KpnI site so that the resultant PCR products can be joined in-frame at the KpnI site to form a full length DNA sequence encoding the hImmu31 VH domain. The ligation of the PCR products for the oligos at the KpnI site and their subcloning into the PstII/BstEII sites of the staging vector, VHpBS, can be completed in a single three-fragment ligation step. The subcloning of the correct sequence into VHpBS can be first analyzed by restriction digestion analysis and subsequently conformed by sequencing reaction according to Sanger et al., *Proc. Natl. Acad. Sci. USA* 74 5463 (1977).

The HindIII/BamHI fragment containing the Ig promoter, leader sequence and the hImmu31 $V_H$ sequence can be excised from the staging vector and subcloned to the corresponding sites in a pSVgpt-based vector, pG1g, which contains the genomic sequence of the human 1 gG constant region, an Ig enhancer and a gpt selection marker, forming the final expression vector, hImmu31pG1g. Similar strategies can be employed for the construction of the hImmu31 Vκ sequence. The restriction site chosen for the ligation of the PCR products for the long oligonucleotides can be NsiI in this case.

The DNA sequence containing the Ig promoter, leader sequence and the hImmu31 Vκ sequence can be excised from the staging vector VKpBR by treatment with BamHI/HindIII, and can be subcloned into the corresponding sites of a pSVhyg-based vector, pKh, which contains the genomic sequence of human kappa chain constant regions, a hygromycin selection marker, an Ig and a kappa enhancer, forming the final expression vector, hImmu31pKh.

The two plasmids can be co-transfected into an appropriate cell, e.g., myeloma Sp2/0-Ag14, colonies selected for hygromycin resistance, and supernatant fluids monitored for production of hImmu31 antibodies by, for example, an ELISA assay, as described below. Alternately, the Vκ and VH expression cassettes can be assembled in the modified staging vectors, VKpBR2 and VHpBS2, excised as XbaI/BamHI and XhoI/BamHI fragments, respectively, and subcloned into a single expression vector, such as pdHL2, as described by Gilles et al., *J Immunol. Methods* 125:191 (1989), Losman et al., *Clin. Cancer Res.* 5:3101 (1999) and in Losman et al., *Cancer*, 80:2660 (1997) for the expression in Sp2/0-Ag 14 cells. Another vector that is useful in the present invention is the GS vector, as described in Barnes et al., *Cytotechnology* 32: 109-123 (2000), which is preferably expressed in the NS0 cell line and CHO cells. Other appropriate mammalian expression systems are described in Werner et al., Arzneim.-Forsch./Drug Res. 48(11), Nr. 8, 870-880 (1998).

Transfection, and assay for antibody secreting clones by ELISA, can be carried out as follows. About 10 μg of hImmu31pKh (light chain expression vector) and 20 μg of hImmu31pG1 g (heavy chain expression vector) can be used for the transfection of 5×10⁶ SP2/0 myeloma cells by electroporation (BioRad, Richmond, Calif.) according to Co et al., J. Immunol., 148: 1149 (1992) which is incorporated by reference. Following transfection, cells may be grown in 96-well microtiter plates in complete HSFM medium (GIBCO, Gaithersburg, Md.) at 37° C., 5% CO$_2$. The selection process can be initiated after two days by the addition of hygromycin selection medium (Calbiochem, San Diego, Calif.) at a final concentration of 500 μg/ml of hygromycin. Colonies typically emerge 2-3 weeks post-electroporation. The cultures can then be expanded for further analysis.

Screening the Clones and Isolating Antibodies

Transfectoma clones that are positive for the secretion of chimeric or humanized heavy chain can be identified by ELISA assay. Briefly, supernatant samples (100 μl) from transfectoma cultures are added in triplicate to ELISA microtiter plates precoated with goat anti-human (GAH)-IgG, F(ab')$_2$ fragment-specific antibody (Jackson ImmunoResearch, West Grove, Pa.). Plates are incubated for 1 h at room temperature. Unbound proteins are removed by washing three times with wash buffer (PBS containing 0.05% polysorbate 20). Horseradish peroxidase (HRP) conjugated GAH-IgQ Fc fragment-specific antibodies (Jackson ImmunoResearch, West Grove, Pa.) are added to the wells, (100 μl of antibody stock diluted×10⁴, supplemented with the unconjugated antibody to a final concentration of 1.0 μg/ml). Following an incubation of 1 h, the plates are washed, typically three times. A reaction solution, [100 μl, containing 167 μg of orthophenylene-diamine (OPD) (Sigma, St. Louis, Mo.), 0.025% hydrogen peroxide in PBS], is added to the wells. Color is allowed to develop in the dark for 30 minutes. The reaction is stopped by the addition of 50 μl of 4 N HCl solution into each well before measuring absorbance at 490 nm in an automated ELISA reader (Bio-Tek instruments, Winooski, Vt.). Bound chimeric antibodies are than determined relative to an irrelevant chimeric antibody standard (obtainable from Scotgen, Ltd., Edinburg, Scotland).

Antibodies can be isolated from cell culture media as follows. Transfectoma cultures are adapted to serum-free medium. For production of chimeric antibody, cells are grown as a 500 ml culture in roller bottles using HSFM. Cultures are centrifuged and the supernatant filtered through a 0.2 micron membrane. The filtered medium is passed through a protein A column (1×3 cm) at a flow rate of 1 ml/min. The resin is then washed with about 10 column volumes of PBS and protein A-bound antibody is eluted from the column with 0.1 M glycine buffer (pH 3.5) containing 10 mM EDTA. Fractions of 1.0 ml are collected in tubes containing 10 μl of 3 M Tris (pH 8.6), and protein concentrations determined from the absorbancies at 280/260 μm. Peak fractions are pooled, dialyzed against PBS, and the antibody concentrated, for example, with the Centricon 30 (Amicon, Beverly, Mass.). The antibody concentration is determined by ELISA, as before, and its concentration adjusted to about 1 mg/ml using PBS. Sodium azide, 0.01% (w/v), is conveniently added to the sample as preservative.

The affinity of a chimeric, humanized or human anti-AFP antibody may be evaluated using a direct binding assay or a competitive binding assay.

Modifying/Optimizing the Recombinant Antibodies

As humanization sometimes results in a reduction or even loss of antibody affinity, additional modification might be required in order to restore the original affinity (See, for example, Tempest et al., *Bio/Technology* 9: 266 (1991); Verhoeyen et al., *Science* 239: 1534 (1988)), which are incorporated by reference. Knowing that cImmu31 exhibits a binding affinity comparable to that of its murine counterpart, defective designs, if any, in the original version of hImm31u can be identified by mixing and matching the light and heavy chains of cImmu31 to those of the humanized version. Preferably, some human residues in the framework regions are replaced by their murine counterparts. Also preferred, a combination of framework sequences from 2 different human antibodies, such as EU and NEWM are used for $V_H$. For example, FR1-3 can come from EU and FR 4 from NEWM.

Other modifications, such as Asn-linked glycosylation sites, can be introduced into a chimerized, human, or humanized Immu31 antibody by conventional oligonucleotide directed site-specific mutagenesis. Detailed protocols for oligonucleotide-directed mutagenesis and related techniques for mutagenesis of cloned DNA are well known. For example, see Sambrook et al., and Ausubel et al. above.

For example, to introduce an Asn in position 18 of hImmu31 Vκ (FIG. 4B), one may alter codon 18 from AGG for Arg to AAC for Asn. To accomplish this, a single stranded DNA template containing the antibody light chain sequence is prepared from a suitable strain of $E.\ coli$ (e.g., dut⁻, ung⁻) in order to obtain a single strand DNA molecule containing a small number of uracils in place of thymidine. Such a DNA template can be obtained by M13 cloning or by in vitro transcription using a SP6 promoter. See, for example, Ausubel et al., eds., CURRENT PROTOCOLS IN MOLECULAR BIOLOGY, John Wiley & Sons, NY, 1987. An oligonucleotide containing the mutated sequence is synthesized conventionally, annealed to the single-stranded template and the product treated with T4 DNA polymerase and T4 DNA ligase to produce a double-stranded DNA molecule. Transformation of wild type E. (dut⁺, ung⁺) cells with the double-stranded DNA provides an efficient recovery of mutated DNA.

Alternatively, an Asn-linked glycosylation site can be introduced into an antibody light chain using an oligonucleotide containing the desired mutation as the primer and DNA clones of the variable regions for the Vk chain, or by using RNA from cells that produce the antibody of interest as a template. Also see, Huse, in ANTIBODY ENGINEERING: A PRACTICAL GUIDE, Boerrebaeck, ed., W.H. Freeman & Co., pp. 103-120, 1992. Site-directed mutagenesis can be performed, for example, using the TRANSFORMER™ kit (Clonetech, Palo Alto, Calif.) according to the manufacturer's instructions.

Alternatively, a glycosylation site can be introduced by synthesizing an antibody chain with mutually priming oligonucleotides, one such containing the desired mutation. See, for example, Uhlmann, Gene 71: 29 (1988); Wosnick et al., Gene 60: 115 (1988); Ausubel et al., above, which are incorporated by reference.

Although the general description above referred to the introduction of an Asn glycosylation site in position 18 of the light chain of an antibody, it will occur to the skilled artisan that it is possible to introduce Asn-linked glycosylation sites elsewhere in the light chain, or even in the heavy chain variable region.

5. Production of Antibody Fragments

Antibody fragments which recognize specific epitopes can be generated by known techniques. The antibody fragments are antigen binding portions of an antibody, such as F(ab')$_2$, Fab', Fab, Fv, sFv and the like. Other antibody fragments include, but are not limited to: the F(ab)'$_2$ fragments which can be produced by pepsin digestion of the antibody molecule and the Fab' fragments, which can be generated by reducing disulfide bridges of the F(ab)'$_2$ fragments. Alternatively, Fab' expression libraries can be constructed (Huse et al., 1989, Science, 246:1274-1281) to allow rapid and easy identification of monoclonal Fab' fragments with the desired specificity. The present invention encompasses antibodies and antibody fragments.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. Nos. 4,704,692, 4,946,778, R. Raag and M. Whitlow, "Single Chain Fvs." FASEB Vol 9:73-80 (1995) and R. E. Bird and B. W. Walker, "Single Chain Antibody Variable Regions," TIBTECH, Vol 9: 132-137 (1991). These references are incorporated herein by reference.

To obtain high-affinity scFv, an scFv library with a large repertoire can be constructed by isolating V-genes from non-immunized human donors using PCR primers corresponding to all known $V_H$, Vκ and $V_\lambda$ gene families. See, e.g., Vaughn et al., *Nat. Biotechnol.,* 14: 309-314 (1996). Following amplification, the Vκ and $V_\lambda$ pools are combined to form one pool. These fragments are ligated into a phagemid vector. The scFv linker, (Gly-Gly-Gly-Gly-Ser)$_3$ (SEQ ID NO: 15), is then ligated into the phagemid upstream of the $V_L$ fragment. The $V_H$ and linker-$V_L$ fragments are amplified and assembled on the $J_H$ region. The resulting $V_H$-linker-$V_L$ fragments are ligated into a phagemid vector. The phagemid library can be panned using filters, as described above, or using immunotubes (Nunc; Maxisorp). Similar results can be achieved by constructing a combinatorial immunoglobulin library from lymphocytes or spleen cells of immunized rabbits and by expressing the scFv constructs in *P. pastoris*. See, e.g., Ridder et al., *Biotechnology,* 13: 255-260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., *Br. J Cancer,* 78: 181-188 (1998); Osbourn et al., *Immunotechnology,* 2: 181-196 (1996).

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. For example, an antibody fragment can be produced by enzymatic cleavage of antibodies with pepsin to provide a 100 Kd fragment denoted F(ab')$_2$. This fragment can be further cleaved using a thiol reducing agent, and optionally a blocking group for the sulfhydryl groups resulting from cleavage of disulfide linkages, to produce 50 Kd Fab' monovalent fragments. Alternatively, an enzymatic cleavage using papain produces two monovalent Fab fragments and an Fc fragment directly. These methods are described, for example, by Goldenberg, U.S. Pat. Nos. 4,036,945 and 4,331,647 and references contained therein, which patents are incorporated herein in their entireties by reference. Also, see Nisonoff et al., *Arch Biochem. Biophys.* 89: 230 (1960); Porter, *Biochem. J.* 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Another form of an antibody fragment is a peptide coding for a single complementarity-determining region (CDR). A CDR is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in MONOCLONAL ANTIBODIES: PRODUCTION, ENGINEERING AND CLINICAL APPLICATION, Ritter et al. (eds.), pages 166-179 (Cambridge University Press 1995); and Ward et al., "Genetic Manipulation and Expression of Antibodies," in MONOCLONAL ANTIBODIES: PRINCIPLES AND APPLICATIONS, Birch et al., (eds.), pages 137-185 (Wiley-Liss, Inc. 1995).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

6. Fusion Proteins

The antibody fusion proteins of the present invention comprise two or more antibodies or fragments thereof and each of the antibodies that compose this fusion protein can contain a therapeutic agent or diagnostic agent. In other words, the antibody fusion protein or fragment thereof can comprise at least one first anti-AFP MAb or fragment thereof and at least one second MAb or fragment thereof that is not an anti-AFP MAb. In a preferred embodiment, the anti-AFP antibody or fragment thereof is an Immu31 antibody or fragment thereof. Preferably, the second MAb is a carcinoma-associated antibody, such as an antibody against CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and other vascular growth factors, Ga 733, 17-1A, ferritin and acidic isoferritin (AIF) of primary hepatic carcinoma, or a combination thereof.

Additionally, one or more of the antibodies or fragments thereof that comprise the antibody fusion protein can have at least one therapeutic or diagnostic/detection agent attached. Further, the diagnostic/detection agents or therapeutic agents need not be the same but can be different therapeutic agents; for example, one can attach a drug and a radioisotope to the same fusion protein. Particularly, an IgG can be radiolabeled with $^{131}$I and attached to a drug. The $^{131}$I can be incorporated into the tyrosine of the IgG and the drug attached to the epsilon amino group of the IgG lysines. Both therapeutic and diagnostic agents also can be attached to reduced SH groups and to the carbohydrate side chains.

Also preferred, the antibody fusion protein of the present invention comprises at least two anti-AFP monoclonal antibodies or fragments thereof, and these may be to different epitopes of the alphafetoprotein antigen or of different human immunoglobulin backbone sequences (or IgGs). Preferably, the anti-AFP antibodies or fragments there of are Immu31 antibodies or fragments thereof.

Multispecific and Multivalent Antibodies

In another embodiment of the instant invention is a conjugated multivalent Immu31 antibody. Compositions and methods for multivalent, multispecific agents are described in Rossi et al., U.S. Patent Application Ser. No. 60/436,359, filed Dec. 24, 2002, and U.S. Patent Application Ser. No. 60/464, 532, filed Apr. 23, 2003, which are incorporated herein by reference in its entirety.

The Immu31 antibodies and fragments thereof of the present invention, as well as other antibodies with different specificities for use in combination therapy, can be made as a multispecific antibody, comprising at least one binding site to an alpha fetoprotein antigen and at least one binding site to another antigen, or a multivalent antibody comprising multiple binding sites to the same epitope or antigen. In a preferred embodiment, the multispecific antibody or fragment thereof comprises at least one binding site to an Immu31 epitope and at least one binding site that is not to the AFP antigen. The Immu31 epitope is an epitope on the AFP antigen that is recognized by the Immu31 antibodies of the present invention. Also preferred, the multispecific antibody or fragment thereof comprises at least one binding site to an Immu31 epitope and at least one binding site to a different epitope on the AFP antigen.

The present invention provides a bispecific antibody or antibody fragment having at least one binding region that specifically binds AFP and at least one other binding region that specifically binds another targeted cell marker or a targetable conjugate. The targetable conjugate comprises a carrier portion which comprises or bears at least one epitope recognized by at least one binding region of the bispecific antibody or antibody fragment. Preferably, the bispecific antibody binds to an Immu31 epitope in the AFP antigen.

A variety of recombinant methods can be used to produce bi-specific antibodies and antibody fragments. For example, bi-specific antibodies and antibody fragments can be produced in the milk of transgenic livestock. See, e.g., Colman, A., *Biochem. Soc. Symp.,* 63: 141-147, 1998; U.S. Pat. No. 5,827,690. Two DNA constructs are prepared which contain, respectively, DNA segments encoding paired immunoglobulin heavy and light chains. The fragments are cloned into expression vectors which contain a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted fragment is flanked on its 3' side by cognate genomic sequences from a mammary-specific gene. This provides a polyadenylation site and transcript-stabilizing sequences. The expression cassettes are coinjected into the pronuclei of fertilized, mammalian eggs, which are then implanted into the uterus of a recipient female and allowed to gestate. After birth, the progeny are screened for the presence of both transgenes by Southern analysis. In order for the antibody to be present, both heavy and light chain genes must be expressed concurrently in the same cell. Milk from transgenic females is analyzed for the presence and functionality of the antibody or antibody fragment using standard immunological methods known in the art. The antibody can be purified from the milk using standard methods known in the art.

Other recent methods for producing bsAbs include engineered recombinant Abs which have additional cysteine residues so that they crosslink more strongly than the more common immunoglobulin isotypes. See, e.g., FitzGerald et al., Protein Eng. 10(10): 1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bi-specific fusion proteins can be produced using molecular engineering. In one form, the bi-specific fusion protein is monovalent, consisting of, for example, a scFv with a single binding site for one antigen and a Fab fragment with a single binding site for a second antigen. In another form, the bi-specific fusion protein is divalent, consisting of, for example, an IgG with two binding sites for one antigen and two scFv with two binding sites for a second antigen.

An anti-AFP multivalent antibody or fragment thereof is also contemplated in the present invention. Preferably, the anti-AFP multivalent antibody or fragment thereof is an Immu31 multivalent antibody or fragment thereof. This multivalent antibody is constructed by association of a first and a second polypeptide. The first polypeptide comprises a first single chain Fv molecule covalently linked to a first immunoglobulin-like domain which preferably is an immunoglobulin light chain variable region domain. The second polypeptide comprises a second single chain Fv molecule covalently linked to a second immunoglobulin-like domain which preferably is an immunoglobulin heavy chain variable region domain. Each of the first and second single chain Fv molecules forms a target binding site, and the first and second immunoglobulin-like domains associate to form a third target binding site.

A single chain Fv molecule with the VL-L-VH configuration, wherein L is a linker, may associate with another single chain Fv molecule with the VH-L-VL configuration to form a bivalent dimer. In this case, the VL domain of the first scFv and the VH domain of the second scFv molecule associate to form one target binding site, while the VH domain of the first scFv and the VL domain of the second scFv associate to form the other target binding site.

Another embodiment of the present invention is an Immu31 bispecific, trivalent antibody comprising two heterologous polypeptide chains associated non-covalently to form three binding sites, two of which have affinity for one target and a third which has affinity for a hapten that can be made and attached to a carrier for a diagnostic and/or therapeutic agent. Preferably, the antibody has two Immu31 binding sites and one CEA or MUC1 binding site. The bispecific, trivalent targeting agents have two different scFvs, one scFv contains two $V_H$ domains from one antibody connected by a short linker to the $V_L$ domain of another antibody and the second scFv contains two $V_L$ domains from the first antibody connected by a short linker to the $V_H$ domain of the other antibody. The methods for generating multivalent, multispecific agents from $V_H$ and $V_L$ domains provide that individual chains synthesized from a DNA plasmid in a host organism are composed entirely of $V_H$ domains (the $V_H$-chain) or entirely of $V_L$ domains (the $V_L$-chain) in such a way that any agent of multivalency and multispecificity can be produced by non-covalent association of one $V_H$-chain with one $V_L$-chain. For example, forming a trivalent, trispecific agent, the $V_H$-chain will consist of the amino acid sequences of three $V_H$ domains, each from an antibody of different specificity, joined by peptide linkers of variable lengths, and the $V_L$-chain will consist of complementary $V_L$ domains, joined by peptide linkers similar to those used for the $V_H$-chain. Since the $V_H$ and $V_L$ domains of antibodies associate in an anti-parallel fashion, the preferred method in this invention has the $V_L$ domains in the $V_L$-chain arranged in the reverse order of the $V_H$ domains in the $V_H$-chain.

Diabodies, Triabodies and Tetrabodies

The anti-AFP antibodies and fragments thereof of the present invention can also be used to prepare functional bispecific single-chain antibodies (bscAb), also called diabodies, and can be produced in mammalian cells using recombinant methods. Preferably, the anti-AFP antibody or fragment thereof is an Immu31 antibody or fragment thereof. See, e.g., Mack et al., *Proc. Natl. Acad. Sci.,* 92: 7021-7025, 1995, incorporated. For example, bscAb are produced by joining two single-chain Fv fragments via a glycine-serine linker using recombinant methods. The V light-chain ($V_L$) and V heavy-chain ($V_H$) domains of two antibodies of interest are isolated using standard PCR methods. The $V_L$ and $V_H$ cDNA's obtained from each hybridoma are then joined to form a single-chain fragment in a two-step fusion PCR. The first PCR step introduces the (Gly-4-Ser1)3 linker (SEQ ID NO: 15), and the second step joins the $V_L$ and $V_H$ amplicons. Each single chain molecule is then cloned into a bacterial expression vector. Following amplification, one of the single-chain molecules is excised and sub-cloned into the other vector, containing the second single-chain molecule of interest. The resulting bscAb fragment is subcloned into an eukaryotic expression vector. Functional protein expression can be obtained by transfecting the vector into chinese hamster ovary cells. Bispecific fusion proteins are prepared in a similar manner. Bispecific single-chain antibodies and bispecific fusion proteins are included within the scope of the present invention.

For example, a humanized, chimeric or human or murine Immu31 monoclonal antibody can be used to produce antigen specific diabodies, triabodies, and tetrabodies. The monospecific diabodies, triabodies, and tetrabodies bind selectively to targeted antigens and as the number of binding sites on the molecule increases, the affinity for the target cell increases and a longer residence time is observed at the desired location. For diabodies, the two chains comprising the $V_H$ polypeptide of the humanized Immu31 MAb connected to the Vκ polypeptide of the humanized Immu31 MAb by a five amino acid residue linker are utilized. Each chain forms one half of the humanized Immu31 diabody. In the case of triabodies, the three chains comprising $V_H$ polypeptide of the humanized Immu31 MAb connected to the Vκ polypeptide of the humanized Immu31 MAb by no linker are utilized. Each chain forms one third of the hImmu31 triabody.

Also contemplated in the present invention is a bi-specific antibody or antibody fragment having at least one arm that is reactive against a targeted tissue such as AFP and at least one other arm that is reactive against a targetable construct. Preferably, one arm of the bispecific antibody binds the Immu31 epitope. The targetable construct is comprised of a carrier portion and at least 2 units of a recognizable hapten. Examples of recognizable haptens include, but are not limited to, histamine succinyl glycine (HSG) and fluorescein isothiocyanate. The targetable construct may be conjugated to a variety of agents useful for treating or identifying diseased tissue. The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may be used.

Large quantities of bscAb and fusion proteins can be produced using *Escherichia coli* expression systems. See, e.g., Zhenping et al., *Biotechnology*, 14: 192-196, 1996. A functional bscAb can be produced by the coexpression in *E. coli* of two "cross-over" scFv fragments in which the $V_L$ and $V_H$ domains for the two fragments are present on different polypeptide chains. The V light-chain ($V_L$) and V heavy-chain ($V_H$) domains of two antibodies of interest are isolated using standard PCR methods. The cDNA's are then ligated into a bacterial expression vector such that C-terminus of the $V_L$ domain of the first antibody of interest is ligated via a linker to the N-terminus of the $V_H$ domain of the second antibody. Similarly, the C-terminus of the $V_L$ domain of the second antibody of interest is ligated via a linker to the N-terminus of the $V_H$ domain of the first antibody. The resulting dicistronic operon is placed under transcriptional control of a strong promoter, e.g., the *E. coli* alkaline phosphatase promoter which is inducible by phosphate starvation. Alternatively, single-chain fusion constructs have successfully been expressed in *E. coli* using the lac promoter and a medium consisting of 2% glycine and 1% Triton X-100. See, e.g., Yang et al., *Appl. Environ. Microbiol.*, 64: 2869-2874, 1998. An *E. coli*, heat-stable, enterotoxin II signal sequence is used to direct the peptides to the periplasmic space. After secretion, the two peptide chains associate to form a non-covalent heterodimer which possesses both antigen binding specificities. The bscAb is purified using standard procedures known in the art, e.g., Staphylococcal protein A chromatography.

Functional bscAbs and fusion proteins also can be produced in the milk of transgenic livestock. See, e.g., Colman, A., *Biochem. Soc. Symp.*, 63: 141-147, 1998; U.S. Pat. No. 5,827,690. The bscAb fragment, obtained as described above, is cloned into an expression vector containing a promoter sequence that is preferentially expressed in mammary epithelial cells. Examples include, but are not limited to, promoters from rabbit, cow and sheep casein genes, the cow α-lactoglobulin gene, the sheep β-lactoglobulin gene and the mouse whey acid protein gene. Preferably, the inserted bscAb is flanked on its 3' side by cognate genomic sequences from a mammary-specific gene. This provides a polyadenylation site and transcript-stabilizing sequences. The expression cassette is then injected into the pronuclei of fertilized, mammalian eggs, which are then implanted into the uterus of a recipient female and allowed to gestate. After birth, the progeny are screened for the presence of the introduced DNA by Southern analysis. Milk from transgenic females is analyzed for the presence and functionality of the bscAb using standard immunological methods known in the art. The bscAb can be purified from the milk using standard methods known in the art. Transgenic production of bscAb in milk provides an efficient method for obtaining large quantities of bscAb.

Functional bscAb and fusion proteins also can be produced in transgenic plants. See, e.g., Fiedler et al., *Biotech.*, 13: 1090-1093, 1995; Fiedler et al., *Immunotechnology*, 3: 205-216, 1997. Such production offers several advantages including low cost, large scale output and stable, long term storage. The bscAb fragment, obtained as described above, is cloned into an expression vector containing a promoter sequence and encoding a signal peptide sequence, to direct the protein to the endoplasmic recticulum. A variety of promoters can be utilized, allowing the practitioner to direct the expression product to particular locations within the plant. For example, ubiquitous expression in tobacco plants can be achieved by using the strong cauliflower mosaic virus 35S promoter, while organ specific expression is achieved via the seed specific legumin B4 promoter. The expression cassette is transformed according to standard methods known in the art. Transformation is verified by Southern analysis. Transgenic plants are analyzed for the presence and functionality of the bscAb using standard immunological methods known in the art. The bscAb can be purified from the plant tissues using standard methods known in the art.

Additionally, transgenic plants facilitate long term storage of bscAb and fusion proteins. Functionally active scFv proteins have been extracted from tobacco leaves after a week of storage at room temperature. Similarly, transgenic tobacco seeds stored for 1 year at room temperature show no loss of scFv protein or its antigen binding activity.

Functional bscAb and fusion proteins also can be produced in insect cells. See, e.g., Mahiouz et al., *J Immunol. Methods*, 212: 149-160 (1998). Insect-based expression systems provide a means of producing large quantities of homogenous and properly folded bscAb. The baculovirus is a widely used expression vector for insect cells and has been successfully applied to recombinant antibody molecules. See, e.g., Miller, L. K., *Ann. Rev. Microbiol.*, 42: 177 (1988); Bei et al., *J Immunol. Methods*, 186: 245 (1995). Alternatively, an inducible expression system can be utilized by generating a stable insect cell line containing the bscAb construct under the transcriptional control of an inducible promoter. See, e.g., Mahiouz et al., *J Immunol. Methods*, 212: 149-160 (1998). The bscAb fragment, obtained as described above, is cloned into an expression vector containing the *Drosphila* metallothionein promoter and the human HLA-A2 leader sequence. The construct is then transfected into *D. melanogaster* SC-2 cells. Expression is induced by exposing the cells to elevated amounts of copper, zinc or cadmium. The presence and functionality of the bscAb is determined using standard immunological methods known in the art. Purified bscAb is obtained using standard methods known in the art.

The ultimate use of the bispecific diabodies described herein is for pre-targeting Immu31 positive tumors for subsequent specific delivery of diagnostic/detection or therapeutic agents. These diabodies bind selectively to targeted antigens allowing for increased affinity and a longer residence time at the desired location. Moreover, non-antigen bound diabodies are cleared from the body quickly and exposure of normal tissues is minimized. The diagnostic/detection and therapeutic agents can include isotopes, drugs, toxins, cytokines, hormones, growth factors, conjugates, radionuclides, and metals. For example, gadolinium metal is used for magnetic resonance imaging (MRI). Examples of radionuclides are $^{225}$Ac, $^{18}$F, $^{68}$Ga, $^{67}$Ga, $^{90}$Y, $^{86}$Y, $^{111}$In, $^{131}$I, $^{125}$I, $^{123}$I, $^{99m}$Tc, $^{94m}$Tc, $^{186}$Re, $^{188}$Re, $^{177}$Lu, $^{62}$Cu, $^{64}$Cu, $^{67}$Cu, $^{212}$Bi, $^{213}$Bi, $^{32}$P, $^{11}$C, $^{13}$N, $^{15}$O, $^{76}$Br, and $^{211}$At. Other radionuclides are also available as diagnostic and therapeutic agents, especially those in the energy range of 60 to 4,000 keV.

More recently, a tetravalent tandem diabody (termed tandab) with dual specificity has also been reported (Cochlovius et al., Cancer Research (2000) 60: 4336-4341). The bispecific tandab is a dimer of two identical polypeptides, each containing four variable domains of two different antibodies ($V_{H1}$, $V_{L1}$, $V_{H2}$, $V_{L2}$) linked in an orientation to facilitate the formation of two potential binding sites for each of the two different specificities upon self-association.

7. Immu31 Immunoconjugates

Any of the anti-AFP antibodies or fragments thereof, or antibody fusion proteins or fragments thereof of the present invention can be conjugated with one or more therapeutic and/or diagnostic/detection agents. Generally, one therapeutic or diagnostic/detection agent is attached to each antibody or antibody fragment but more than one therapeutic agent or diagnostic agent can be attached to the same antibody, fusion protein, or fragment thereof. Such a therapeutic or diagnostic/ detection agent may be a peptide which bears a diagnostic/ detection or therapeutic agent. An immunoconjugate retains the immunoreactivity of the antibody component, i.e., the antibody moiety has about the same or slightly reduced ability to bind the cognate antigen after conjugation as before conjugation.

A wide variety of diagnostic/detection and therapeutic agents can be advantageously conjugated to the antibody, fusion protein, or fragment thereof of the present invention. In a preferred embodiment, the diagnostic/detection agents are selected from the group consisting of radioisotopes for nuclear imaging, intraoperative and endoscopic detection, enhancing agents for use in magnetic resonance imaging or in ultrasonography, radiopaque and contrast agents for X-rays and computed tomography, and fluorescent compounds for fluoroscopy, including endoscopic fluoroscopy. Fluorescent and radioactive agents conjugated to antibodies or used in bispecific, pretargeting methods, are particularly useful for endoscopic, intraoperative or intravascular detection of the targeted antigens associated with diseased tissues or clusters of cells, such as malignant tumors, as disclosed in Goldenberg U.S. Pat. Nos. 5,716,595, 6,096,289 and U.S. application Ser. No. 09/348,818, incorporated herein by reference in their entirety, particularly with gamma-, beta-, and positron-emitters. Radionuclides useful for positron emission tomography include, but are not limited to: F-18, Mn-51, Mn-52m, Fe-52, Co-55, Cu-62, Cu-64, Ga-68, As-78, Br-75, Br-76, Rb-82m, Sr-83, Y-86, Zr-89, Tc-94m, In-110, I-120, and 1-124.

The therapeutic agents recited here are those agents that also are useful for administration separately with a naked antibody, as described herein. Therapeutic agents include, for example, chemotherapeutic drugs such as vinca alkaloids and other alkaloids, anthracyclines, epidophyllotoxins, taxanes, antimetabolites, alkylating agents, antibiotics, COX-2 inhibitors, antimitotics, antiangiogenic and apoptotoic agents, particularly doxorubicin, methotrexate, taxol, CPT-11, camptothecans, and others from these and other classes of anticancer agents, and the like. Other useful cancer chemotherapeutic drugs for the preparation of immunoconjugates and antibody fusion proteins include nitrogen mustards, alkyl sulfonates, nitrosoureas, triazenes, folic acid analogs, COX-2 inhibitors, pyrimidine analogs, purine analogs, platinum coordination complexes, hormones, toxins (e.g., RNAse, *Pseudomonas* exotoxin), and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

A toxin, such as *Pseudomonas* exotoxin, may also be complexed to or form the therapeutic agent portion of an immunoconjugate of the Immu31 antibody or fragment thereof of the present invention. Additionally, the toxin may be used in combination with a naked Immu31 antibody or fragment thereof, an Immu31 fusion protein or fragment thereof, or a Immu31 antibody or fragment thereof conjugated to a different therapeutic agent. Other toxins suitably employed in the preparation of such conjugates or other fusion proteins, include ricin, abrin, ribonuclease (RNase), DNase I, *Staphylococcal* enterotoxin-A, pokeweed antiviral protein, gelonin, diphtherin toxin, *Pseudomonas* exotoxin, and *Pseudomonas* endotoxin. See, for example, Pastan et al., Cell 47:641 (1986), and Goldenberg, C A—*A Cancer Journal for Clinicians* 44:43 (1994). Additional toxins suitable for use in the present invention are known to those of skill in the art and are disclosed in U.S. Pat. No. 6,077,499, which is incorporated in its entirety by reference. These can be derived, for example, from animal, plant and microbial sources, or chemically or recombinantly engineered. The toxin can be a plant, microbial, or animal toxin, or a synthetic variation thereof.

An immunomodulator, such as a cytokine may also be conjugated to, or form the therapeutic agent portion of the Immu31 immunoconjugate, or be administered unconjugated to the chimeric, humanized or human anti-AFP antibody, fusion protein, or fragment thereof of the present invention. As used herein, the term "immunomodulator" includes cytokines, stem cell growth factors, lymphotoxins, such as tumor necrosis factor (TNF), and hematopoietic factors, such as interleukins (e.g., interleukin-1 (IL-1), IL-2, IL-3, IL-6, IL-10, IL-12 and IL-18), colony stimulating factors (e.g., granulocyte-colony stimulating factor (G-CSF) and granulocyte macrophage-colony stimulating factor (GM-CSF)), interferons (e.g., interferons-α, -β and -γ), the stem cell growth factor designated "S1 factor," erythropoietin and thrombopoietin. Examples of suitable immunomodulator moieties include IL-2, IL-6, IL-10, IL-12, IL-18, interferon-γ, TNF-α, and the like. Alternatively, subjects can receive a naked Immu31 antibody or fragment thereof, or naked fusion protein or fragment thereof, and a separately administered cytokine, which can be administered before, concurrently or after administration of the naked Immu31 antibody or fragment, or naked Immu31 fusion protein or fragment thereof. The Immu31 antibody or fragment there or fusion protein or fragment thereof of may also be conjugated to an immunomodulator. The immunomodulator may also be conjugated to a hybrid antibody consisting of one or more antibodies or antibody fragments binding to different antigens. Such an antigen may also be an immunomodulator. For example, CD40 or other immunomodulators may be administered in combination with a Immu31 antibody or fragment thereof either together, before or after the antibody combinations are administered.

Furthermore, an Immu31 antibody or fragment thereof, or fusion protein or fragment thereof may comprise a γ-emitting radionuclide or a positron-emitter useful for diagnostic imaging. Examples of diagnostic/detection agents include diverse labels, radionuclides, chelators, dyes, contrast agents, fluorescent compounds, chromagens, and other marker moieties. Radionuclides useful for positron emission tomography include, but are not limited to: $^{18}$F, $^{51}$Mn, $^{52m}$Mn, $^{52}$Fe, $^{55}$Co, $^{62}$Cu, $^{64}$Cu, $^{68}$Ga, $^{72}$As, $^{75}$Br, $^{76}$Br, $^{82m}$Rb, $^{83}$Sr, $^{86}$Y, $^{89}$Zr, $^{94m}$Tc, $^{110}$In, $^{120}$I, and $^{124}$I. Total decay energies of useful positron-emitting radionuclides are preferably <2,000 keV, more preferably under 1,000 keV, and most preferably <700 keV. Radionuclides useful as diagnostic agents utilizing gamma-ray detection include, but are not limited to: Cr-51, Co-57, Co-58, Fe-59, Cu-67, Ga-67, Se-75, Ru-97, Tc-99m, In-111, In-114m, I-123, I-125, I-131, Yb-169, Hg-197, and T1-201. Decay energies of useful gamma-ray emitting radionuclides are preferably 20-2000 keV, more preferably 60-600 keV, and most preferably 100-300 keV.

Additionally, radionuclides suitable for treating a diseased tissue include, but are not limited to, P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, and Bi-213, Co-58, Ga-67, Br-80m, Tc-99m, Rh-103m, Pt-109, In-111, Sb-119, I-125, Ho-161, Os-189m, Ir-192, Dy-152, At-211, Bi-212, Ra-223, Rn-219, Po-215, Bi-211, Ac-225, Fr-221, At-217, Bi-213 and Fm-255.

Suitable diagnostic imaging isotopes are usually in the range of 20 to 2,000 keV, while suitable therapeutic radionuclides are usually in the range of 20 to 10,000 keV. See for example, U.S. patent application entitled "Labeling Targeting Agents with Gallium-68"—Inventors G. L. Griffiths and W. J. McBride, (U.S. Provisional Application No. 60/342,104), which discloses positron emitters, such as $^{18}$F, $^{68}$Ga, $^{94m}$Tc, and the like, for imaging purposes and which is incorporated in its entirety by reference. A suitable radionuclide is an Auger emitter, and preferably has an energy of less than 1000 keV. Also preferred is a β emitter and has an energy between 20 and 5000 keV or an α emitter and has an energy between 2000 and 10,000 keV.

A therapeutic or diagnostic/detection agent can be attached at the hinge region of a reduced antibody component via disulfide bond formation. As an alternative, such peptides can be attached to the antibody component using a heterobifunctional cross-linker, such as N-succinyl 3-(2-pyridyldithio) proprionate (SPDP). Yu et al., *Int. J. Cancer* 56: 244 (1994). General techniques for such conjugation are well known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same peptide that is bound to a thiol group, or the carbohydrate moiety can be used to bind a different peptide.

Methods for conjugating peptides to antibody components via an antibody carbohydrate moiety are well known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, all of which are incorporated in their entirety by reference. The general method involves reacting an antibody component having an oxidized carbohydrate portion with a carrier polymer that has at least one free amine function and that is loaded with a plurality of peptide. This reaction results in an initial Schiff base (imine) linkage, which can be stabilized by reduction to a secondary amine to form the final conjugate.

However, if the Fc region is absent, for example, if the antibody used as the antibody component of the immunoconjugate is an antibody fragment, it is still possible to attach a diagnostic/detection a therapeutic agent. A carbohydrate moiety can be introduced into the light chain variable region of a full-length antibody or antibody fragment. See, for example, Leung et al., *J Immunol.* 154: 5919 (1995); Hansen et al., U.S. Pat. No. 5,443,953 (1995), Leung et al., U.S. Pat. No. 6,254,868, all of which are incorporated in their entirety by reference. The engineered carbohydrate moiety is used to attach the therapeutic or diagnostic agent.

8. Targetable Constructs

The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates maybe used.

Peptides having as few as two amino-acid residues may be used, preferably two to ten residues, if also coupled to other moieties such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates. For instance, the known peptide DTPA-Tyr-Lys(DTPA)-OH (wherein DTPA is diethylenetriaminepentaacetic acid) has been used to generate antibodies against the indium-DTPA portion of the molecule. However, by use of the non-indium-containing molecule, and appropriate screening steps, new Abs against the tyrosyl-lysine dipeptide can be made. More usually, the antigenic peptide will have four or more residues, such as the peptide DOTA-Phe-Lys(HSG)-Tyr-Lys(HSG)-NH$_2$ (SEQ ID NO: 7), wherein DOTA is 1,4,7,10-tetraazacyclododecane-tetraacetic acid and HSG is the histamine succinyl glycyl group of the formula:

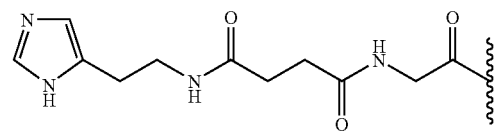

The non-metal-containing peptide may be used as an immunogen, with resultant Abs screened for reactivity against the Phe-Lys-Tyr-Lys (SEQ ID NO: 48) backbone.

The invention also contemplates the incorporation of unnatural amino acids, e.g., D-amino acids, into the backbone structure to ensure that, when used with the final bsAb/linker system, the arm of the bsAb which recognizes the linker moiety is completely specific. The invention further contemplates other backbone structures such as those constructed from non-natural amino acids and peptoids.

The peptides to be used as immunogens are synthesized conveniently on an automated peptide synthesizer using a solid-phase support and standard techniques of repetitive orthogonal deprotection and coupling. Free amino groups in the peptide, that are to be used later for chelate conjugation, are advantageously blocked with standard protecting groups such as an acetyl group. Such protecting groups will be known to the skilled artisan. See Greene and Wuts *Protective*

*Groups in Organic Synthesis,* 1999 (John Wiley and Sons, N.Y). When the peptides are prepared for later use within the bsAb system, they are advantageously cleaved from the resins to generate the corresponding C-terminal amides, in order to inhibit in vivo carboxypeptidase activity.

The haptens of the immunogen comprise an immunogenic recognition moiety, for example, a chemical hapten. Using a chemical hapten, preferably the HSG hapten, high specificity of the linker for the antibody is exhibited. This occurs because antibodies raised to the HSG hapten are known and can be easily incorporated into the appropriate bispecific antibody. Thus, binding of the linker with the attached hapten would be highly specific for the antibody or antibody fragment.

Chelate Moieties

The presence of hydrophilic chelate moieties on the linker moieties helps to ensure rapid in vivo clearance. In addition to hydrophilicity, chelators are chosen for their metal-binding properties, and are changed at will since, at least for those linkers whose bsAb epitope is part of the peptide or is a non-chelate chemical hapten, recognition of the metal-chelate complex is no longer an issue.

A chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, *Chem. Britain* 22:430 (1986)). Moreover, monoclonal antibodies have been coupled with photoactivated dyes for achieving phototherapy. Mew et al., *J. Immunol.* 130:1473 (1983); idem., *Cancer Res.* 45:4380 (1985); Oseroff et al., *Proc. Natl. Acad. Sci. USA* 83:8744 (1986); idem., *Photochem. Photobiol.* 46:83 (1987); Hasan et al., *Prog. Clin. Biol. Res.* 288:471 (1989); Tatsuta et al., *Lasers Surg. Med.* 9:422 (1989); Pelegrin et al., *Cancer* 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

Particularly useful metal-chelate combinations include 2-benzyl-DTPA and its monomethyl and cyclohexyl analogs, used with $^{47}$Sc, $^{52}$Fe, $^{55}$Co, $^{67}$Ga, $^{68}$Ga, $^{111}$In, $^{89}$Zr, $^{90}$Y, $^{161}$Tb, $^{177}$Lu, $^{212}$Bi, $^{213}$Bi, $^{225}$Ac for radio-imaging and RAIT. The same chelators, when complexed with non-radioactive metals, such as Mn, Fe and Gd can be used for MRI, when used along with the bsAbs of the invention. Macrocyclic chelators such as NOTA (1,4,7-triaza-cyclononane-N,N', N"-triacetic acid), DOTA, and TETA (p-bromoacetamidobenzyl-tetraethylaminetetraacetic acid) are of use with a variety of metals and radiometals, most particularly with radionuclides of Ga, Y and Cu, respectively.

DTPA and DOTA-type chelators, where the ligand includes hard base chelating functions such as carboxylate or amine groups, are most effective for chelating hard acid cations, especially Group Ia and Group IIIa metal cations. Such metal-chelate complexes can be made very stable by tailoring the ring size to the metal of interest. Other ring-type chelators such as macrocyclic polyethers are of interest for stably binding nuclides such as $^{223}$Ra for RAIT. Porphyrin chelator may be used with numerous radiometals, and are also useful as certain cold metal complexes for bsAb-directed immunophototherapy. More than one type of chelators may be conjugated to a carrier to bind multiple metal ions, e.g., cold ions, diagnostic radionuclides and/or therapeutic radionuclides. Particularly useful therapeutic radionuclides include, but are not limited to, $^{32}$P, $^{33}$P, $^{47}$Sc, $^{64}$Cu, $^{67}$Cu, $^{67}$Ga, $^{90}$Y, $^{111}$Ag, $^{111}$In, $^{125}$I, $^{131}$I, $^{142}$Pr, $^{153}$Sm, $^{166}$Tb, $^{166}$Dy, $^{166}$Ho, $^{177}$Lu, $^{186}$Re, $^{188}$Re, $^{189}$Re, $^{212}$Pb, $^{212}$Bi, $^{213}$Bi, $^{211}$At, $^{223}$Ra and $^{225}$Ac. Particularly useful diagnostic/detection radionuclides include, but are not limited to, $^{18}$F, $^{52}$Pe, $^{62}$Cu, $^{64}$Cu, $^{67}$Cu, $^{67}$Ga, $^{68}$Ga, $^{86}$Y, $^{89}$Zr, $^{94m}$Tc, $^{94}$Tc, $^{99m}$Tc, $^{111}$In, $^{123}$I, $^{124}$I, $^{125}$I, $^{131}$I, $^{154-158}$Gd and $^{175}$Lu.

Chelators such as those disclosed in U.S. Pat. No. 5,753,206, especially thiosemi-carbazonylglyoxylcysteine (Tscg-Cys) and thiosemicarbazinyl-acetylcysteine (Tsca-Cys) chelators are advantageously used to bind soft acid cations of Tc, Re, Bi and other transition metals, lanthanides and actinides that are tightly bound to soft base ligands, especially sulfur- or phosphorus-containing ligands. It can be useful to link more than one type of chelator to a peptide, e.g., a DTPA or similar chelator for, say In(III) cations, and a thiol-containing chelator, e.g., Tscg-Cys, for Tc cations. Because antibodies to a di-DTPA hapten are known (Barbet'395, supra) and are readily coupled to a targeting antibody to form a bsAb, it is possible to use a peptide hapten with cold diDTPA chelator and another chelator for binding a radioisotope, in a pretargeting protocol, for targeting the radioisotope. One example of such a peptide is Ac-Lys(DTPA)-Tyr-Lys(DTPA)-Lys (Tscg-CYS-)-NH$_2$ (SEQ ID NO: 16). This peptide can be preloaded with In(III) and then labeled with 99-m-Tc cations, the In(III) ions being preferentially chelated by the DTPA and the Tc cations binding preferentially to the thiol-containing Tscg-Cys. Other hard acid chelators such as NOTA, DOTA, TETA and the like can be substituted for the DTPA groups, and Mabs specific to them can be produced using analogous techniques to those used to generate the anti-di-DTPA Mab.

It will be appreciated that two different hard acid or soft acid chelators can be incorporated into the linker, e.g., with different chelate ring sizes, to bind preferentially to two different hard acid or soft acid cations, due to the differing sizes of the cations, the geometries of the chelate rings and the preferred complex ion structures of the cations. This will permit two different metals, one or both of which may be radioactive or useful for MRI enhancement, to be incorporated into a linker for eventual capture by a pretargeted bsAb.

Preferred chelators include NOTA, DOTA and Tscg and combinations thereof. These chelators have been incorporated into a chelator-peptide conjugate motif as exemplified in the following constructs:

(a) DOTA-Phe-Lys(HSG)-D-Tyr-Lys(HSG)-NH$_2$;

(b) DOTA-Phe-Lys(HSG)-Tyr-Lys(HSG)-NH$_2$; (SEQ ID NO: 7)

(c) Ac-Lys(HSG)D-Tyr-Lys(HSG)-Lys(Tscg-Cys)-NH$_2$;

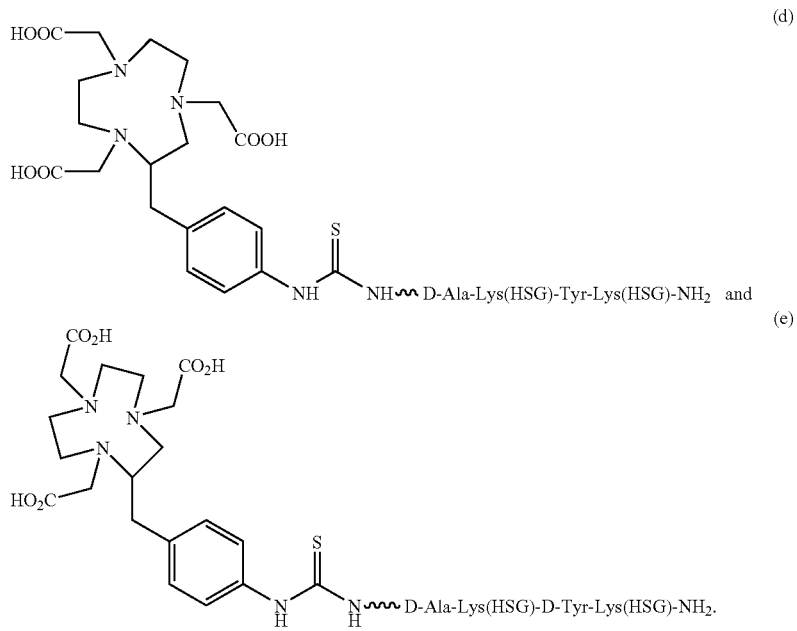

The chelator-peptide conjugates (d) and (e), above, has been shown to bind $^{68}$Ga and is thus useful in positron emission tomography (PET) applications.

Chelators are coupled to the linker moieties using standard chemistries which are discussed more fully in the working Examples below. Briefly, the synthesis of the peptide Ac-Lys(HSG)D-Tyr-Lys(HSG)-Lys(Tscg-Cys-)-NH$_2$ was accomplished by first attaching Aloc-Lys(Fmoc)-OH to a Rink amide resin on the peptide synthesizer. The protecting group abbreviations "Aloe" and "Fmoc" used herein refer to the groups allyloxycarbonyl and fluorenylmethyloxy carbonyl. The Fmoc-Cys(Trt)-OH and TscG were then added to the side chain of the lysine using standard Fmoc automated synthesis protocols to form the following peptide: Aloc-Lys(Tscg-Cys(Trt)-rink resin. The Aloe group was then removed. The peptide synthesis was then continued on the synthesizer to make the following peptide: (Lys(Aloc)-D-Tyr-Lys(Aloc)-Lys(Tscg-Cys(Trt)-)-rink resin. Following N-terminus acylation, and removal of the side chain Aloe protecting groups. The resulting peptide was then treated with activated N-trityl-HSG-OH until the resin gave a negative test for amines using the Kaiser test. See Karacay et al. *Bioconjugate Chem.,* 11:842-854 (2000). The synthesis of Ac-Lys(HSG)D-Tyr-Lys(HSG)-Lys(Tscg-Cys-)-NH$_2$, as well as the syntheses of DOTA-Phe-Lys(HSG)-D-Tyr-Lys(HSG)-NH$_2$; and DOTA-Phe-Lys(HSG)-Tyr-Lys(HSG)-NH$_2$ (SEQ ID NO: 7) are described in greater detail below.

9. Preparation of Metal Chelates

Chelator-peptide conjugates may be stored for long periods as solids. They may be metered into unit doses for metal-binding reactions, and stored as unit doses either as solids, aqueous or semi-aqueous solutions, frozen solutions or lyophilized preparations. They may be labeled by well-known procedures. Typically, a hard acid cation is introduced as a solution of a convenient salt, and is taken up by the hard acid chelator and possibly by the soft acid chelator. However, later addition of soft acid cations leads to binding thereof by the soft acid chelator, displacing any hard acid cations which may be chelated therein. For example, even in the presence of an excess of cold $^{111}$InCl$_3$, labeling with 99m-Tc(V) glucoheptonate or with Tc cations generated in situ with stannous chloride and Na99m-TcO$_4$ proceeds quantitatively on the soft acid chelator. Other soft acid cations such as $^{186}$Re, $^{188}$Re, $^{213}$Bi and divalent or trivalent cations of Mn, Co, Ni, Pb, Cu, Cd, Au, Fe, Ag (monovalent), Zn and Hg, especially $^{64}$Cu and $^{67}$Cu, and the like, some of which are useful for radioimmunodiagnosis or radioimmunotherapy, can be loaded onto the linker peptide by analogous methods. Re cations also can be generated in situ from perrhenate and stannous ions or a prereduced rhenium glucoheptonate or other transchelator can be used. Because reduction of perrhenate requires more stannous ion (typically above 200 μg/mL final concentration) than is needed for the reduction of Tc, extra care needs to be taken to ensure that the higher levels of stannous ion do not reduce sensitive disulfide bonds such as those present in disulfide-cyclized peptides. During radiolabeling with rhenium, similar procedures are used as are used with the Tc-99m. A preferred method for the preparation of ReO metal complexes of the Tscg-Cys-ligands is by reacting the peptide with ReOCl$_3$(P(Ph$_3$)$_2$ but it is also possible to use other reduced species such as R$^e$O(ethylenediamine)$_2$.

10. Humanized, Chimeric and Human Antibodies Use for Treatment and Diagnosis

Contemplated in the present invention is the use of murine, humanized, chimeric and human anti-AFP antibodies and fragments thereof in delivery methods of therapeutic and diagnostic/detection agents, and therapeutic and diagnostic/detection methods. Preferably, the murine, chimeric, humanized and human anti-AFP antibodies and fragments thereof are chimeric, humanized or human Immu31 antibodies.

For example, a method of delivering a diagnostic/detection agent, a therapeutic agent, or a combination thereof to a target comprising (i) administering to a subject the antibody or fragment thereof an antibody, fusion protein, or fragment thereof; (ii) waiting a sufficient amount of time for an amount of the non-binding protein to clear the subject's blood stream;

and (iii) administering to said subject a carrier molecule comprising a diagnostic/detection agent, a therapeutic agent, or a combination thereof, that binds to a binding site of said antibody. Preferably, the carrier molecule binds to more than one binding site of the antibody.

The present invention also contemplates methods of diagnosing or detecting a malignancy in a subject. Diagnosis/detection may be accomplished by administering a diagnostically effective amount of a diagnostic/detection immunoconjugate, comprising an anti-AFP monoclonal antibody or fragment thereof or a fusion protein or fragment thereof, wherein said anti-AFP MAb or fragment thereof or fusion protein or fragment thereof is bound to at least one diagnostic/detection agent, formulated in a pharmaceutically acceptable excipient, and detecting said label. Preferably, the anti-AFP antibody, fusion protein, or fragment thereof is an Immu31 antibody.

In a related vein, a method of diagnosing or detecting a malignancy in a subject comprising (i) performing an in vitro diagnosis assay on a specimen from said subject with a composition comprising a anti-AFP MAb or fragment thereof or a antibody fusion protein or fragment thereof of any one of the antibodies, fusion proteins, or fragments thereof of the present invention, is also considered. Preferably, the in vitro diagnosis assay is selected from the group consisting of immunoassays, RT-PCR and immunohistochemistry.

In the methods described herein, radioactive and non-radioactive agents can be used as diagnostic agents. A suitable non-radioactive diagnostic agent is a contrast agent suitable for magnetic resonance imaging, a radiopaque compound for X-rays or computed tomography, or a contrast agent suitable for ultrasound. Magnetic imaging agents include, for example, non-radioactive metals, such as manganese, iron and gadolinium, complexed with metal-chelate combinations that include 2-benzyl-DTPA and its monomethyl and cyclohexyl analogs, when used along with the antibodies of the invention. See U.S. Ser. No. 09/921,290 filed on Oct. 10, 2001, which is incorporated in its entirety by reference. In a preferred embodiment, the contrast agent is an ultrasound-enhancing agent. Still preferred, the ultrasound-enhancing agent is a liposome. Radiopaque and contrast materials are used for enhancing X-rays and computed tomography, and include iodine compounds, barium compounds, gallium compounds, thallium compounds, etc. Specific compounds include barium, diatrizoate, ethiodized oil, gallium citrate, iocarmic acid, iocetamic acid, iodamide, iodipamide, iodoxamic acid, iogulamide, iohexyl, iopamidol, iopanoic acid, iprocemic acid, iosefamic acid, ioseric acid, iosulamide meglumine, iosemetic acid, iotasul, iotetric acid, iothalamic acid, iotroxic acid, ioxaglic acid, ioxotrizoic acid, ipodate, meglumine, metrizamide, metrizoate, propyliodone, and thallous chloride.

Also described in the present invention is the use of murine, chimeric, humanized and human anti-AFP antibodies and fragments thereof in methods for treating malignancies. For example, a malignancy of particular interest in this patent is a cancer of the liver. Occasionally, ovarian carcinoma, and rarely gastrointestinal and lung cancers may produce AFP. Preferably, the anti-AFP antibodies and fragements thereof are Immu31 antibodies and fragments thereof. The method comprises administering to a subject a therapeutically effective amount of an antibody or fragment thereof or an antibody fusion protein or fragment thereof comprising at least two MAbs or fragments thereof, wherein at least one anti-AFP MAb or fragment thereof or fusion proteins or fragments thereof are any one of the antibodies of the present invention, formulated in a pharmaceutically suitable excipient. In another embodiment, a second MAb, fusion protein or fragment thereof is not an anti-AFP antibody, fusion protein or fragment thereof.

In a related vein, a method of treating a cancer cell in a subject comprising (i) administering to said subject a therapeutically effective amount of a composition comprising a naked or conjugated anti-AFP MAb or fragment thereof or antibody fusion protein or fragment thereof, of any one of the antibodies, fusion proteins, or fragments thereof of the present invention, (ii) formulating said anti-AFP MAb or fragment thereof or antibody fusion protein or fragment thereof in a pharmaceutically suitable excipient, is contemplated. Preferably, such a composition further comprises a second antibody, fusion protein, or fragment thereof. The second antibody, fusion protein, or fragment thereof may or may not be an anti-AFP antibody, fusion protein or fragment thereof. Also preferred, the anti-AFP antibody, fusion protein, or fragment thereof is an Immu31 antibody, fusion protein, or fragment thereof. The preferred mode of administration is parenterally. Also preferred, the dosage is repeatedly administered. Still preferred, the anti-AFP antibody is administered in a dosage of 20 to 2000 milligrams protein per dose.

The compositions for treatment contain at least one naked murine, humanized, chimeric or human anti-AFP antibody or fragment thereof alone or in combination with other anti-AFP antibodies or antibody fragments thereof, such as other anti-AFP humanized, chimeric or human antibodies. Preferably, the anti-AFP antibody, fusion protein, or fragment thereof in the composition for treatment is administered in a dosage of 20-2000 milligrams per dose. Also preferred, the anti-AFP antibody or fragment thereof in the composition for treatment is an Immu31 antibody or fragment thereof. The present invention also contemplates treatment with at least one naked humanized, chimeric or human anti-AFP antibody or fragment thereof in combination with other antibodies or antibody fragments thereof that are not anti-AFP antibodies, whereby these other antibodies can be administered unconjugated (naked) or conjugated with at least one diagnostic/detection or therapeutic agent. For example, other antibodies suitable for combination therapy include, but are not limited to, carcinoma-associated antibodies and fragments thereof such as antibodies CEA, EGP-1, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and against other vascular growth factors, Ga 733, ferritin and acidic isoferritin (AIF) of primary hepatic carcinoma, or a combination thereof. Suitable antibodies could also include those targeted against oncogene markers or products, or antibodies against tumor-vasculature markers, such as the angiogenesis factor, VEGF, and antibodies against certain immune response modulators, such as antibodies to CD40. Additionally, treatment can be effected with at least one humanized, chimeric or human anti-AFP immunoconjugate or fragment thereof alone or in combination with another anti-AFP antibodies or antibody fragments thereof, such as other anti-AFP humanized, chimeric or human antibody. Preferably, the anti-AFP antibody is a fragment thereof is an Immu31 antibody or fragment thereof. Still preferred, compositions for treatment can contain at least one humanized, chimeric or human anti-AFP immunoconjugate or fragment thereof in combination with other antibodies or antibody fragments thereof that are not anti-AFP antibodies, these being either naked or conjugated to a therapeutic agent. Such non-anti-AFP antibodies Similarly, conjugated and naked anti-AFP humanized, chimeric or human antibodies or fragments thereof may be used alone or may be administered with, but unconjugated to, the various diagnostic/detection or therapeutic agents described herein. Also, naked or conjugated anti-AFP antibodies to the same or different epitope or antigen may be also combined with one or more of the antibodies of the present invention. Preferably, the anti-AFP antibody or fragment thereof is an Immu31 antibody or fragment thereof.

Accordingly, the present invention contemplates the administration of murine, humanized, chimeric and human Immu31 antibodies and fragments thereof alone, as a naked antibody, or administered as a multimodal therapy. Multimodal therapies of the present invention further include immunotherapy with naked or conjugated anti-AFP antibodies supplemented with administration of other conjugated or unconjugated antibody, fusion protein, or fragment thereof. For example, a humanized, chimeric or human Immu31 antibody may be combined with another naked humanized, naked chimeric or naked human Immu31 antibody, or a humanized, chimeric or human Immu31 antibody immunoconjugate, such as a humanized, chimeric or human Immu31 antibody conjugated to an isotope, one or more chemotherapeutic agents, cytokines, enzymes, enzyme-inhibitors, hormones or hormone antagonists, metals, toxins, or a combination thereof. A fusion protein of a murine, humanized, chimeric or human Immu31 antibody and a toxin or may also be used in this invention. Many different antibody combinations may be constructed, either as naked antibodies or as partly naked and partly conjugated with a therapeutic agent or immunomodulator, or merely in combination with another therapeutic agents, such as a cytotoxic drug or with radiation.

The compositions for treatment contain at least one murine, humanized, chimeric or human monoclonal anti-AFP antibody or fragment thereof alone or in combination with other antibodies and fragments thereof, such as other naked or conjugated, murine, humanized, chimeric, or human antibodies, or fragments thereof, or fusion proteins or fragments thereof, or therapeutic agents. In particular, combination therapy with a fully human antibody is also contemplated and is produced by the methods as set forth above.

Naked or conjugated antibodies, fusion proteins, or fragments thereof may be also combined with one or more of the antibodies, fusion proteins, or fragments thereof to the same or different epitope or antigen. For example, a naked, murine, humanized, chimeric or human Immu31 antibody may be combined with a naked murine, humanized, naked chimeric or naked human Immu31 antibody; a murine, humanized, chimeric or human naked Immu31 antibody may be combined with a Immu31 immunoconjugate; a naked murine, humanized, chimeric, human Immu31 antibody may be combined with a different antibody radioconjugate or a different naked antibody; a murine, humanized, chimeric or fully human Immu31 antibody may be combined with a murine, humanized, chimeric or human Immu31 antibody conjugated to an isotope, or to one or more chemotherapeutic agents, cytokines, toxins, enzymes, enzyme inhibitors, hormones, hormone antagonists, or a combination thereof. A fusion protein of a murine, humanized, chimeric or human Immu31 antibody and a toxin or immunomodulator may also be used in this invention. Many different antibody combinations, targeting at least two different antigens may be constructed, either as naked antibodies or as partly naked and partly conjugated with a therapeutic agent or immunomodulator, or merely in combination with another therapeutic agents, such as a cytotoxic drug or with radiation.

Multimodal therapies of the present invention further include immunotherapy with naked Immu31 antibodies or fragments thereof supplemented with administration of carcinoma associated antibodies in the form of a conjugated or unconjugated antibody, fusion proteins, or fragment thereof. In a preferred embodiment, antibodies or fragments thereof for multimodal therapy include, but are not limited to, antibodies against CEA, EGP-I, EGP-2 (e.g., 17-1A), MUC-1, MUC-2, MUC-3, MUC-4, PAM-4, KC4, TAG-72, EGFR, HER2/neu, BrE3, Le-Y, A3, Ep-CAM, Tn, and Thomson-Friedenreich antigens, tumor necrosis antigens, tenascin, an oncogene, an oncogene product, IL-6, IGF-1, IGFR-1, tumor angiogenesis antigens, such as vascular endothelium growth factor (VEGF), placental growth factor (P1GF), ED-B fibronectin, and other vascular growth factors, Ga 733, ferritin and acidic isoferritin (AIF) of primary hepatic carcinoma, or a combination thereof. These antibodies include polyclonal, monoclonal, chimeric, human or humanized antibodies and fragments thereof that recognize at least one epitope on these antigenic determinants.

In another form of multi modal therapy, subjects receive naked anti-AFP antibodies or fragments thereof, and/or anti-AFP immunoconjugates or fragments thereof, in conjunction with standard cancer chemotherapy. Preferably, the anti-AFP antibody or fragment thereof is an Immu31 antibody or fragment thereof. 5-fluorouracil in combination with folinic acid, alone or in combination with irinotecan (CPT-11), is a regimen used to treat colorectal cancer. Other suitable combination chemotherapeutic regimens are well known, such as with oxaliplatin alone, or in combination with these other drugs, to those of skill in the art. In ovarian cancer, still other chemotherapeutic agents may be preferred, such as any one of the taxanes and platinum agents, Thio-TEPA and other alkylating agents (e.g., chlorambucil), as well as gemcitabine and other more recent classes of cytotoxic drugs. In a preferred multimodal therapy, both chemotherapeutic drugs and cytokines are co-administered with a conjugated or unconjugated anti-AFP antibody, fusion protein, or fragment thereof, according to the present invention. Preferably, the anti-AFP antibody or fragment thereof is an Immu31 antibody or fragment thereof. The cytokines, chemotherapeutic drugs and antibody, fusion protein, or fragment thereof, can be administered in any order, or together.

The present invention also encompasses the use of the bsAb and at least one therapeutic or diagnostic/detection agent associated with the linker moieties discussed above in intraoperative, intravascular, and endoscopic tumor and lesion detection, biopsy and therapy as described in U.S. Pat. No. 6,096,289, and incorporated herein by reference. Preferably, the bispecific antibody has at least one arm that binds the AFP antigen, and more preferably, the Immu31 epitope.

The anti-AFP antibodies, fusion proteins, and fragments thereof of the present invention can be employed not only for therapeutic or imaging purposes, but also as aids in performing research in vitro. For example, the bsAbs of the present invention can be used in vitro to ascertain if a targetable construct can form a stable complex with one or more bsAbs. Such an assay would aid the skilled artisan in identifying targetable constructs which form stable complexes with bsAbs. This would, in turn, allow the skilled artisan to identify targetable constructs which are likely to be superior as therapeutic and/or imaging agents. Preferably, the anti-AFP antibody, fusion protein, or fragment thereof is an Immu31 antibody, fusion protein, or fragment thereof.

The assay is advantageously performed by combining the targetable construct in question with at least two molar equivalents of a bsAb. Following incubation, the mixture is analyzed by size-exclusion HPLC to determine whether or not the construct has bound to the bsAb. Alternatively, the assay is performed using standard combinatorial methods wherein solutions of various bsAbs are deposited in a standard 96-well plate. To each well, is added solutions of targetable construct(s). Following incubation and analysis, one can readily determine which construct(s) bind(s) best to which bsAb(s).

It should be understood that the order of addition of the bsAb to the targetable construct is not crucial; that is, the bsAb may be added to the construct and vice versa. Likewise, neither the bsAb nor the construct needs to be in solution; that is, they may be added either in solution or neat, whichever is most convenient. Lastly, the method of analysis for binding is not crucial as long as binding is established. Thus, one may analyze for binding using standard analytical methods including, but not limited to, FABMS, high-field NMR or other appropriate method in conjunction with, or in place of, size-exclusion HPLC.

Bispecific Antibody Therapy and Diagnosis

The present invention provides a bispecific antibody or antibody fragment having at least one binding region that specifically binds a targeted cell marker and at least one other binding region that specifically binds a targetable conjugate. The targetable conjugate comprises a carrier portion which comprises or bears at least one epitope recognized by at least one binding region of the bispecific antibody or antibody fragment.

For example, a method of treating or identifying diseased tissues in a subject, comprising: (A) administering to said subject a bi-specific antibody or antibody fragment having at least one arm that specifically binds a targeted tissue and at least one other arm that specifically binds a targetable conjugate, wherein said one arm that specifically binds a targeted tissue is an Immu31 antibody; (B) optionally, administering to said subject a clearing composition, and allowing said composition to clear non-localized antibodies or antibody fragments from circulation; (C) administering to said subject a first targetable conjugate which comprises a carrier portion which comprises or bears at least one epitope recognizable by said at least one other arm of said bi-specific antibody or antibody fragment, and one or more conjugated therapeutic or diagnostic agents; and (D) when said therapeutic agent is an enzyme, further administering to said subject 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or 4) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site, is described. Optionally, when said first targetable conjugate comprises a prodrug, administering a second targetable conjugate which comprises a carrier portion which comprises or bears at least one epitope recognizable by said at least one other arm of said bi-specific antibody or antibody or antibody fragment, and an enzyme capable of converting said prodrug to a drug or of reconverting a detoxified intermediate of said drug to a toxic form. Preferably, the targetable conjugate comprises at least two HSG haptens.

In a related vein, a method for detecting or treating tumors expressing AFP in a mammal is described. This method comprises (A) administering an effective amount of a bispecific antibody or antibody fragment comprising at least one arm that specifically binds a targeted tissue and at least one other arm that specifically binds a targetable conjugate, wherein said one arm that specifically binds a targeted tissue is an Immu31 antibody or fragment thereof; and (B) administering a targetable conjugate selected from the group consisting of (i) DOTA-Phe-Lys(HSG)-D-Tyr-Lys(HSG)-NH$_2$; (ii) DOTA-Phe-Lys(HSG)-Tyr-Lys(HSG)-NH$_2$ (SEQ ID NO: 7); (iii) Ac-Lys(HSG)D-Tyr-Lys(HSG)-Lys(Tscg-Cys)-NH$_2$;

and 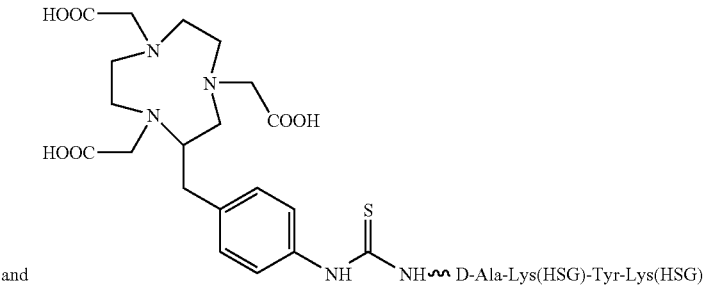 (iv)

-continued

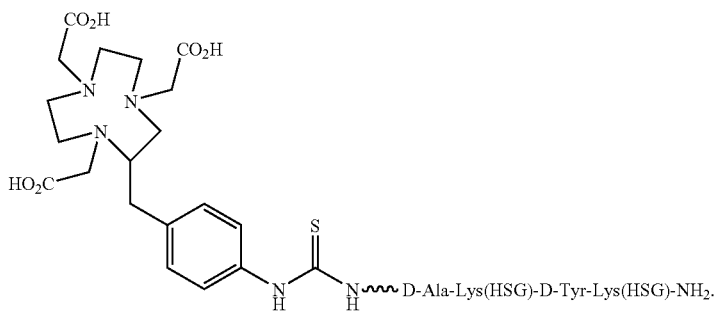

(v)

Optionally, the method further comprises administering to a subject a clearing composition, and allowing the composition to clear non-localized antibodies or antibody fragments from the circulation.

Bispecific antibodies and fragments thereof of the present invention are useful in pretargeting methods and provide a preferred way to deliver two therapeutic agents or two diagnostic/detection agents to a subject. U.S. Ser. No. 09/382,186 discloses a method of pretargeting using a bispecific antibody, in which the bispecific antibody is labeled with $^{125}$I and delivered to a subject, followed by a divalent peptide labeled with $^{99m}$Tc. The delivery results in excellent tumor/normal tissue ratios for $^{131}$I and $^{99m}$Tc, thus showing the utility of two diagnostic radioisotopes. Any combination of known therapeutic agents or diagnostic agents can be used to label the Immu31 antibodies, Immu31 fusion proteins, and fragments thereof of the present invention. The binding specificity of the Immu31 immunoconjugate, the efficacy of the therapeutic agent or diagnostic agent and the effector activity of the Fc portion of the antibody can be determined by standard testing of the conjugates.

The administration of a bsAb and a therapeutic agent associated with the linker moieties discussed above may be conducted by administering the bsAb at some time prior to administration of the therapeutic agent which is associated with the linker moiety. The doses and timing of the reagents can be readily devised by a skilled artisan, and are dependent on the specific nature of the reagents employed. If a bsAb-F(ab')$_2$ derivative is given first, then a waiting time of 24-72 hr before administration of the linker moiety would be appropriate. If an IgG-Fab' bsAb conjugate is the primary targeting vector, then a longer waiting period before administration of the linker moiety would be indicated, in the range of 3-10 days.

After sufficient time has passed for the bsAb to target to the diseased tissue, the diagnostic/detection agent is administered. Subsequent to administration of the diagnostic/detection agent, imaging can be performed. Tumors can be detected in body cavities by means of directly or indirectly viewing various structures to which energy of the appropriate wavelength is delivered and then collected. Lesions at any body site can be viewed so long as nonionizing radiation or energy can be delivered and recaptured from these structures. For example, PET which is a high resolution, non-invasive, imaging technique can be used with the inventive antibodies for the visualization of human disease. In PET, 511 keV gamma photons produced during positron annihilation decay are detected.

The linker moiety may also be conjugated to an enzyme capable of activating a prodrug at the target site or improving the efficacy of a normal therapeutic by controlling the body's detoxification pathways. Following administration of the bsAb, an enzyme conjugated to the linker moiety, a low MW hapten recognized by the second arm of the bsAb, is administered. After the enzyme is pretargeted to the target site, a cytotoxic drug is injected, which is known to act at the target site. The drug may be one which is detoxified by the mammal's ordinary detoxification processes. For example, the drug may be converted into the potentially less toxic glucuronide in the liver. The detoxified intermediate can then be reconverted to its more toxic form by the pretargeted enzyme at the target site. Alternatively, an administered prodrug can be converted to an active drug by the pretargeted enzyme. The pretargeted enzyme improves the efficacy of the treatment by recycling the detoxified drug. This approach can be adopted for use with any enzyme-drug pair.

The enzyme capable of activating a prodrug at the target site or improving the efficacy of a normal therapeutic by controlling the body's detoxification pathways may alternatively be conjugated to the hapten. The enzyme-hapten conjugate is administered to the subject following administration of the pre-targeting bsAb and is directed to the target site. After the enzyme is localized at the target site, a cytotoxic drug is injected, which is known to act at the target site, or a prodrug form thereof which is converted to the drug in situ by the pretargeted enzyme. As discussed above, the drug is one which is detoxified to form an intermediate of lower toxicity, most commonly a glucuronide, using the mammal's ordinary detoxification processes. The detoxified intermediate, e.g., the glucuronide, is reconverted to its more toxic form by the pretargeted enzyme and thus has enhanced cytotoxicity at the target site. This results in a recycling of the drug. Similarly, an administered prodrug can be converted to an active drug through normal biological processes. The pretargeted enzyme improves the efficacy of the treatment by recycling the detoxified drug. This approach can be adopted for use with any enzyme-drug pair.

The invention further contemplates the use of the inventive bsAb and the diagnostic agent(s) in the context of Boron Neutron Capture Therapy (BNCT) protocols. BNCT is a binary system designed to deliver ionizing radiation to tumor cells by neutron irradiation of-tumor-localized $^{10}$B atoms. BNCT is based on the nuclear reaction which occurs when a stable isotope, isotopically enriched $^{10}$B (present in 19.8% natural abundance), is irradiated with thermal neutrons to produce an alpha particle and a $^7$Li nucleus. These particles have a path length of about one cell diameter, resulting in high linear energy transfer. Just a few of the short-range 1.7 MeV alpha particles produced in this nuclear reaction are sufficient to target the cell nucleus and destroy it. Success with BNCT of cancer requires methods for localizing a high concentration of $^{10}B$ at tumor sites, while leaving non-target organs essentially boron-free. Compositions and methods for treating tumors in subjects using pre-targeting bsAb for BNCT are described in co-pending patent application Ser. No. 09/205,243, incorporated herein in its entirety and can easily be modified for the purposes of the present invention.

A clearing agent may be used which is given between doses of the bsAb and the linker moiety. The present inventors have discovered that a clearing agent of novel mechanistic action may be used with the invention, namely a glycosylated anti-idiotypic (anti-Id) Fab' fragment targeted against the disease targeting arms) of the bsAb. For example, anti-CSAp (Mu-9 Ab)x anti-peptide bsAb is given and allowed to accrete in disease targets to its maximum extent. To clear residual bsAb, an anti-idiotypic (anti-Id) Ab to Mu-9 is given, preferably as a glycosylated Fab' fragment. The clearing agent binds to the bsAb in a monovalent manner, while its appended glycosyl residues direct the entire complex to the liver, where rapid metabolism takes place. Then the therapeutic which is associated with the linker moiety is given to the subject. The anti-Id Ab to the Mu-9 arm of the bsAb has a high affinity and the clearance mechanism differs from other disclosed mechanisms (see Goodwin et al., ibid), as it does not involve cross-linking, because the anti-Id-Fab' is a monovalent moiety.

nostic agents; and (C) optionally, a clearing composition useful for clearing non-localized antibodies and antibody fragments; and (D) optionally, when said therapeutic agent conjugated to said first targetable conjugate is an enzyme, 1) a prodrug, when said enzyme is capable of converting said prodrug to a drug at the target site; or 2) a drug which is capable of being detoxified in said subject to form an intermediate of lower toxicity, when said enzyme is capable of reconverting said detoxified intermediate to a toxic form, and, therefore, of increasing the toxicity of said drug at the target site, or 3) a prodrug which is activated in said subject through natural processes and is subject to detoxification by conversion to an intermediate of lower toxicity, when said enzyme is capable of reconverting said detoxified intermediate to a toxic form, and, therefore, of increasing the toxicity of said drug at the target site, or 4) a second targetable conjugate which comprises a carrier portion which comprises or bears at least one epitope recognizable by said at least one other arm of said bi-specific antibody or antibody fragment, and a prodrug, when said enzyme is capable of converting said prodrug to a drug at the target site. Preferably, the targetable conjugate is selected from the group consisting of (i) DOTA-Phe-Lys(HSG)-D-Tyr-Lys(HSG)-NH$_2$; (ii) DOTA-Phe-Lys(HSG)-Tyr-Lys(HSG)-NH$_2$ (SEQ ID NO: 7); (iii) Ac-Lys(HSG)D-Tyr-Lys(HSG)-Lys(Tscg-Cys)-NH$_2$;

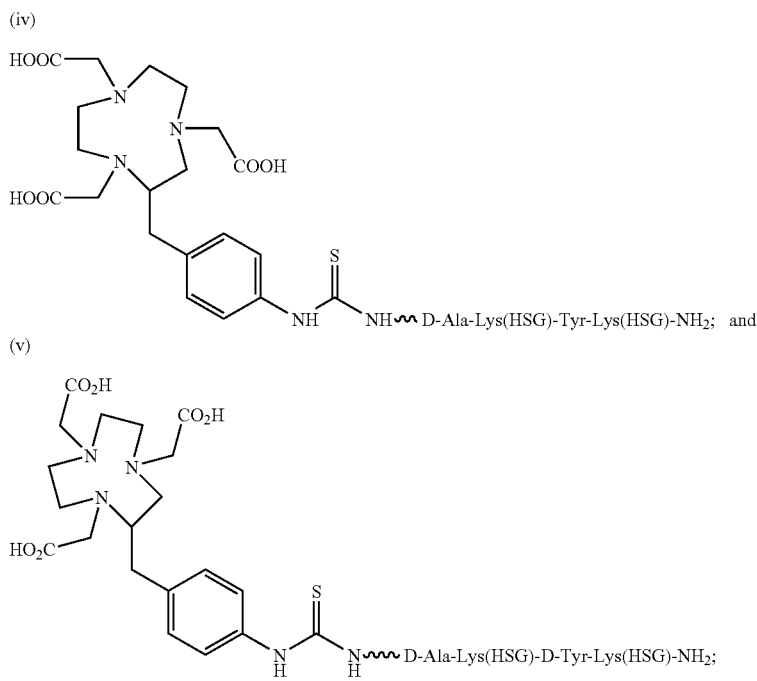

Also contemplated herein is a kit useful for treating or identifying diseased tissues in a subject comprising: (A) a bi-specific antibody or antibody fragment having at least one arm that specifically binds a targeted tissue and at least one other arm that specifically binds a targetable conjugate, wherein said one arm that specifically binds a targeted tissue is an Immu31 antibody or fragment thereof; (B) a first targetable conjugate which comprises a carrier portion which comprises or bears at least one epitope recognizable by said at least one other arm of said bi-specific antibody or antibody fragment, and one or more conjugated therapeutic or diag- A method of screening for a targetable conjugate is also described, comprising (A) contacting said targetable construct with a bi-specific antibody or antibody fragment having at least one arm that specifically binds a targeted tissue and at least one other arm that specifically binds said targetable conjugate to give a mixture, wherein said one arm that specifically binds a targeted tissue is a Immu31 antibody or fragment thereof; and (B) optionally incubating said mixture; and (C) analyzing said mixture.

The present invention further provides a method for imaging malignant tissue or cells in a mammal expressing AFP; a method of intraoperatively identifying/disclosing diseased tissues expressing AFP, in a subject; a method for endoscopic identification of diseased tissues expressing AFP, in a subject and a method for the intravascular identification of diseased tissues expressing AFP, in a subject. Such methods comprise (A) administering an effective amount of a bispecific antibody or antibody fragment comprising at least one arm that specifically binds a targeted tissue expressing AFP and at least one other arm that specifically binds a targetable conjugate, wherein said one arm that specifically binds a targeted tissue is an Immu31 antibody or fragment thereof; and (B) administering a targetable conjugate selected from the group consisting of (i) DOTA-Phe-Lys(HSG)-D-Tyr-Lys(HSG)-NH$_2$; (ii) DOTA-Phe-Lys(HSG)-Tyr-Lys(HSG)-NH$_2$ (SEQ ID NO: 7); (iii) Ac-Lys(HSG)D-Tyr-Lys(HSG)-Lys(Tscg-Cys)-NH$_2$;

labeled with a diagnostic/detection radioisotope, a MRI image-enhancing agent or a fluorescent label.

In a related vein, a method for close-range lesion detection, during an operative, intravascular, laparoscopic, or endoscopic procedure, wherein the method comprises: (A) injecting a subject to such a procedure parenterally with an effective amount of an Immu31 immunoconjugate or fragment thereof, (B) conducting the procedure within 48 hours of the injection; (C) scanning the accessed interior of the subject at close range with a detection means for detecting the presence of said labeled antibody or fragment thereof; and (D) locating the sites of accretion of said labeled antibody or fragment thereof by detecting elevated levels of said labeled antibody or fragment thereof at such sites with the detection means, is also described.

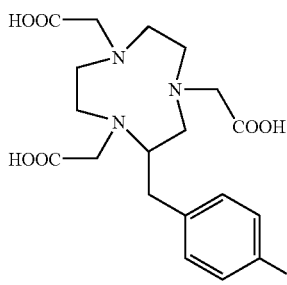

(iv)

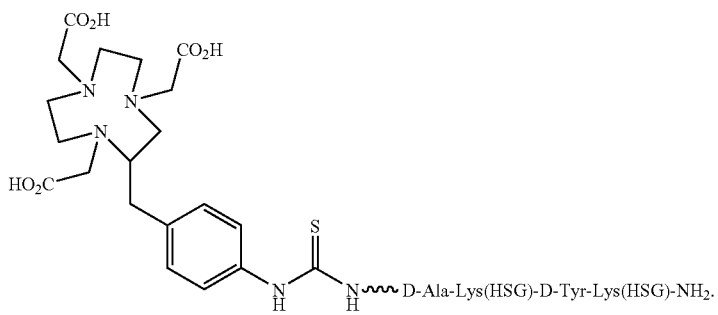

(v)

Also considered herein is a method of detection of lesions during an endoscopic, laparoscopic, intravascular catheter, or surgical procedure, wherein the method comprises: (A) injecting a subject who is to undergo such a procedure with a bispecific antibody F(ab)$_2$ or F(ab')$_2$ fragment, wherein the bispecific antibody or fragment has a first antibody binding site which specifically binds to a AFP antigen, and has a second antibody binding site which specifically binds to a hapten, and permitting the antibody fragment to accrete at target sites; (B) optionally clearing non-targeted antibody fragments using a galactosylated anti-idiotype clearing agent if the bispecific fragment is not largely cleared from circulation within about 24 hours of injection, and injecting a bivalent labeled hapten, which quickly localizes at the target site and clears through the kidneys; (C) detecting the presence of the hapten by close-range detection of elevated levels of accreted label at the target sites with detection means, within 48 hours of the first injection, and conducting said procedure, wherein said detection is performed without the use of a contrast agent or subtraction agent. Preferably, the hapten is 11. Pharmaceutically Suitable Excipients The murine, humanized, chimeric and human Immus31 MAbs to be delivered to a subject can consist of the MAb alone, immunoconjugate, fusion protein, or can comprise one or more pharmaceutically suitable excipients, one or more additional ingredients, or some combination of these.

The conjugated or unconjugated anti-AFP antibodies and fragments thereof, or fusion proteins and fragments thereof, of the present invention can be formulated according to known methods to prepare pharmaceutically useful compositions. Preferably, the anti-AFP antibody or fragment thereof is an Immu31 antibody or fragment thereof. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The conjugated or unconjugated anti-AFP antibody, fusion protein, or fragments thereof of the present invention can be formulated for intravenous administration via, for example, bolus injection or continuous infusion. Preferably, the anti-AFP antibody or fragments is an Immu31 antibody or fragment thereof. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic or diagnostic/detection immunoconjugate or naked antibody, fusion protein, or fragments thereof. Control release preparations can be prepared through the use of polymers to complex or adsorb the immunoconjugate or naked antibody. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate or antibody from such a matrix depends upon the molecular weight of the immunoconjugate or antibody, the amount of immunoconjugate, antibody within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON' S PHARMACEUTICAL SCIENCES, 18th Edition (Mack Publishing Company 1990), and revised editions thereof.

The conjugated or unconjugated anti-AFP antibody, fusion protein, or fragments thereof may also be administered to a mammal subcutaneously or even by other parenteral routes. Moreover, the administration may be by continuous infusion or by single or multiple boluses. In general, the dosage of an administered immunoconjugate, or naked antibody, fusion protein or fragments thereof for humans will vary depending upon such factors as the patient's age, weight, height, sex, general medical condition and previous medical history. Typically, it is desirable to provide the recipient with a dosage of immunoconjugate, naked antibody fusion protein, naked antibody, or fragments thereof that is in the range of from about 1 mg/kg to 20 mg/kg as a single intravenous infusion, although a lower or higher dosage also may be administered as circumstances dictate. This dosage may be repeated as needed, for example, once per week for 4-10 weeks, preferably once per week for 8 weeks, and more preferably, once per week for 4 weeks. It may also be given less frequently, such as every other week for several months. The dosage may be given through various parenteral routes, with appropriate adjustment of the dose and schedule.

For purposes of therapy, the conjugated or unconjugated antibody, fusion protein, or fragment thereof is administered to a mammal in a therapeutically effective amount. Preferably, the anti-AFP antibody or fragment thereof is an Immu31 antibody or fragment thereof. A suitable subject for the present invention is usually a human, although a non-human animal subject is also contemplated. An antibody preparation is said to be administered in a "therapeutically effective amount" if the amount administered is physiologically significant. An agent is physiologically significant if its presence results in a detectable change in the physiology of a recipient mammal. In particular, an antibody preparation of the present invention is physiologically significant if its presence invokes an antitumor response or mitigates the signs and symptoms of an autoimmune disease state. A physiologically significant effect could also be the evocation of a humoral and/or cellular immune response in the recipient mammal.

12. Expression Vectors

The DNA sequence encoding a murine, humanized, chimeric or human Immu31 MAb can be recombinantly engineered into a variety of known host vectors that provide for replication of the nucleic acid. These vectors can be designed, using known methods, to contain the elements necessary for directing transcription, translation, or both, of the nucleic acid in a cell to which it is delivered. Known methodology can be used to generate expression constructs the have a protein-coding sequence operably linked with appropriate transcriptional/translational control signals. These methods include in vitro recombinant DNA techniques and synthetic techniques. For example, see Sambrook et al., 1989, MOLECULAR CLONING: A LABORATORY MANUAL, Cold Spring Harbor Laboratory (New York); Ausubel et al., 1997, CURRENT PROTOCOLS IN MOLECULAR BIOLOGY, John Wiley & Sons (New York). Also provided for in this invention is the delivery of a polynucleotide not associated with a vector.

Vectors suitable for use in the instant invention can be viral or non-viral. Particular examples of viral vectors include adenovirus, AAV, herpes simplex virus, lentivirus, and retrovirus vectors. An example of a non-viral vector is a plasmid. In a preferred embodiment, the vector is a plasmid.

An expression vector, as described herein, is a polynucleotide comprising a gene that is expressed in a host cell. Typically, gene expression is placed under the control of certain regulatory elements, including constitutive or inducible promoters, tissue-specific regulatory elements, and enhancers. Such a gene is said to be "operably linked to" the regulatory elements.

Preferably, the expression vector of the instant invention comprises the DNA sequence encoding a humanized, chimeric or human Immu31 MAb, which includes both the heavy and the light chain variable and constant regions. However, two expression vectors may be used, with one comprising the heavy chain variable and constant regions and the other comprising the light chain variable and constant regions. Still preferred, the expression vector further comprises a promoter, a DNA sequence encoding a secretion signal peptide, a genomic sequence encoding a human Ig light or heavy chain constant region, an Ig enhancer element and at least one DNA sequence encoding a selection marker.

The invention is further described by reference to the following examples, which are provided for illustration only. The invention is not limited to the examples but rather includes all variations that are evident from the teachings provided herein.

EXAMPLES

Example 1

Molecular Cloning and Sequence Elucidation for Immu31 Heavy and Light Chain Variable Regions The VH and Vκ genes of Immu31 was obtained by RT-PCR as described by Orlandi et al. (PNAS 86:3833-3837 (1989) and Leung et al. (Hybridoma 13:469-476 (1994).

The total RNA was prepared from Immu31 hybridoma cells and RT-PCR was performed to isolate the V genes as described (Leung et al. Hybridoma 13:469-476 (1994)). Briefly, the first strand cDNA was reverse transcribed from total RNA using the SuperScript preamplification system (GIBCO/BRL) in a reaction volume of 60 μl containing 20 μg of the RNAs annealed with 150 ng of random hexamer primer, 20 mM Tris-HCl, pH 8.4, 15 mM KCl, 2.5 mM $MgCl_2$, 5 mM dNTP mix, 10 mM DTT, 0.1 mg/ml BSA, and 600 units of SuperScript reverse trascriptase transcriptase. The elongation step was initially allowed to proceed at room temperature for 10 min followed by incubation at 42° C. for 50 min. The reaction was terminated by heating the reaction mixture at 90° C. for 5 min. PCR reactions using the first strand cDNA as templates were then carried out to amplify mouse Ig VH and Vκ genes. The Vκ sequence of Immu31 was amplified by using the primer pair VK1BACK (Orlandi et al. PNAS 86:3833-3837 (1989) CK3'-BH (Leung et al. (Leung et al., 1993)). The resulting PCR products were ~350 bp. While the VH sequence was amplified with VH1BACK (Orlandi et al. PNAS 86:3833-3837 (1989)) and CH1-C (5'-AGCTGG-GAAGGTGTGCAC-3') (SEQ ID NO. 17), which anneals to the CH1 region of murine γ chains, resulting in PCR products of ~500 bp. Both Vκ and VH PCR fragments were cloned into pCR2.1 AT-cloning vector and the DNA sequences were determined by DNA sequencing (Sanger et al. PNAS 74:5463-5467 (1974)).

Multiple clones (8 for each) were selected for sequencing to eliminate possible errors resulted from PCR reaction. Majority of clones contained an identical murine Ig VH (6) or Vκ (7) sequence, which was designated as Immu31VH and Immu31Vκ, respectively (FIG. 1). The amino acid sequences encoded by the genes were deduced and are also shown in FIG. 1. No defective mutations were identified within the sequences and important residues such as cycleines for intradomain disulfide linkages were located at appropriate positions. Comparison with other mouse Vκ sequences revealed that Immu31Vκ is a member of the kappa light chain subclass V while Immu31VH belongs to mouse Ig heavy chain subclass IIA (Kabat et al., 1991).

Example 2

Construction of the Expression Vector for a Chimeric Immu31

To evaluate the "authenticity" of the cloned V gene segments, the putative murine Vκ and VH were constructed into a chimeric Immu31 (cImmu31) containing human IgG and kappa constant domains and expressed in Sp2/0 cells. To facilitate subcloning of Immu31Vκ (FIG. 1A) to generate the expression vector, the DNA sequence was modified, at 3' end to include a BglII restriction site, AGATCT, by PCR amplification with primers VK1BACK and VK1FOR (Orlandi et al. PNAS 86:3833-3837 (1989)). The resulting PCR product was digested with PvuII and BglII and force-cloned into a pBR327-based staging vector (digested with PvuII and BclI), VKpBR, which contained Ig promoter, signal peptide sequence for secretion and convenient restriction sites to facilitate in-frame ligation of the VκPCR product (Leung et al.(Leung et al., 1994)). Similarly, the nucleotide sequences at positions 336-342 of Immu31VH (FIG. 1B) were converted to BstEII site, GGTCACC, by PCR with primers VH1BACK and VH1FOR (Orlandi et al., 1989). The VH PCR product was then digested with PstI and BstEII and ligated into PstI and BstEII digested VHpBS, a pBluescript-based staging vector containing an Ig promoter, a signal peptide sequence and convenient restriction sites for in-frame-ligation of a VH sequence. The final V sequences in the cImmu31 were designated as cImmu31VH and Vκ, confirmed by DNA sequencing and shown in FIGS. 2A and 2B, respectively.

The fragments containing the VH and Vκ sequences of cImmu31, together with the promoter and signal peptide sequences, were excised from the respective staging vectors, cImmu31 VHpBS and cImmu31 VKpBR, by double restriction-digestion with HindIII and BamHI. The ca. 850 bp VH fragment was then subcloned into the HindIII/BamHI site of a mammalian expression vector, pG1 g, in which cImmu31 VH was linked to the genomic sequence of the human γ1 constant gene (Leung et al. (Leung et al., 1994)). Similarly, the ca. 650 bp Vκ fragment was inserted into the HindIII/BamHI site of pKh, which carrying the genomic gene sequence of a human κ constant region, an Ig enhancer, a κ enhancer, and the hygromycin-resistant gene as a marker for selection of transfectants (Leung et al. (Leung et al., 1994)). The final expression vectors were designated as cImmu31pG1 g and cImmu31pKh, respectively.

Example 3

Transfection and Expression of Chimeric and Humanized Immu31

Same procedures were employed to express cImmu31 or hImmu31 in Sp2/0 cells by transfection as described by Leung et al. (Hybridoma 13:469-476 (1994)). As an example, expression of cImmu31 is described here. Briefly, linearized cImmu31pKh and cImmu31pG1g were co-transfected into Sp2/0 cells by electroporation. The transfected cells were grown in 96-well plate for 2 days and then selected by the addition of hygromycin at a final concentration of 500 units/ml. The colonies began to emerge 10-14 days after electroporation. Supernatants from colonies surviving selection were screened for the presence of mouse-human chimeric IgG by ELISA. Briefly, supernatant samples from surviving clones were added in triplicate to ELISA microtiter plates precoated with goat anti-human (GAR) IgG, F(ab')$_2$ fragment-specific antibody (Jackson ImmunoResearch, West Grove, Pa.). The plates were incubated for 1 h at room temperature. Unbound proteins were removed by washing three times with washing buffer (PBS with 0.05% polysorbate-20). Horseradish peroxidase (HRP)-conjugated GAR IgC, Fc fragment-specific antibody (Jackson ImmunoResearch) was then added to the wells. Following incubation for 1 h, the plates were washed six times with washing buffer. A substrate solution containing 4 mM of o-phenylenediamine dihydrochloride (OPD) and 0.04% $H_2O_2$, was added to the wells. The reaction was allowed to proceed in the dark for 30 min and stopped by the addition of $H_2SO_4$ solution into each well before measuring absorbance at 490 nm in an automated ELISA reader. The positive cell clones were expanded and cImmu31 was purified from cell culture supernatant by affinity chromatography on a Protein A column. A competition Ag-binding assay was carried out to compare the immunoreactivity of chimeric and murine Immu31 (Example 4). As shown in FIG. 3, cImmu31 and murine Immu31 competed equally well for the binding of biotinylated murine Immu31 to the AFP antigen. These data demonstrated that the immunoreactivity of cImmu31 is comparable to that of murine Immu31, thus confirming the authenticity of the Vκ and VH sequences obtained (FIG. 1).

Similar procedures were also used with another expression vector, pdHL2, as described in Example 5. Approximately 30 μg of hImmu31pdHL2 was linearized by digestion with SalI and transfected into Sp2/0 cells by electroporation. The transfected cells were plated into 96-well plate and were allowed to recover for 2 days. After two days, MTX at a final concentration of 0.025 µM was added to the medium to select transfectants. MTX-resistant clones emerged in 2 weeks and Supernatants from colonies surviving selection were monitored for human IgG secretion by ELISA as described above. Positive cell clones were expanded and hImmu31 was purified from cell culture supernatant by affinity chromatography on a Protein A column.

Example 4

The Ag-binding Activity Assays

The Ag-binding activities of cImmu31 and hImmu31 were determined with ELISA in ELISA microplate wells coated with AFP (Scripps Research Institute, La Jolla, Calif.). Briefly, constant amount of biotinylated murine Immu31 was mixed with varying concentrations (0.01-100 µg/ml) of testing Abs (Immu31, cImmu31 or hImmu31), and added into AFP-coated microwells, and incubated at room temperature for 1 h. After washing, HRP conjugated streptavidin was added and incubated for 1 h at room temperature. The amount of HRP-conjugated streptavidin bound to the AFP-bound biotinylated Immu31 was revealed by reading OD at 490 nm in an ELISA reader after the addition of a substrate solution containing 4 mM OPD and 0.04% $H_2O_2$.

Example 5

Choice of Human Frameworks and Sequence Design for hImmu31

By comparing the murine Immu31 V region FR sequences to that of human Abs in the Kabat database (Sequences of Proteins of Immunological Interest (Bethesda, Md.: U.S. Department of Health and Human Services, Public Health Service, National Institute of Health, 1991), the FRs of human REI and EU VH were found to exhibit the highest degree of sequence homology to that of Immu31 Vκ and Immu31VH, respectively (FIG. 4). One exception is the FR4 of Immu31VH, which showed the highest sequence homology with that of NEWM VH (FIG. 4A). Thus, the FR sequences of REI VK (FIG. 4B), FR1-3 of EU VH and FR4 of NEWM VH (FIG. 4A) were selected as the scaffold for grafting the respective CDRs of Immu31. A few amino acid residues in murine FRs that flank the putative CDRs were maintained in hImmu31 based on the consideration that these residues have more impact on Ag binding than other FR residues. These residues are 5Q, 27Y, 28A, 30T, 46Y, 48I, 66K, 67A and 94R of VH, and 4L, 39K, 48M, 49H, 58I, 69R, 100G and 107K of VK. Additionally, based on the results of previous humanization of LL2 (Leung et al. Mol. Immunol. 32:1413-1427 (1995>>, two charged residues, 39K in FR2 and 69R in FR3 of Immu31 Vκ, that have the potential of CDR contacts and might affect the immunoreactivity of the resultant Ab were retained in the design of the humanized FR sequences (FIG. 4B). In order to evaluate the impact of the charged murine residues 39K and 69R on the binding activity of the Ab, two alternate versions of humanized Vκ, hImmu31 VKT39, and hImmu31 VKT69, were designed by substituting either residue 39K or 69R with the corresponding human residue, threonine, respectively (FIG. 4C).

FIG. 3A compares the VH sequence of human EU with murine and humanized Immu31 VH, and 3B compares human REI with murine and humanized Immu31Vκ. The dots indicate the residues in Immu31 and hImmu31 sequences that are identical to the corresponding residues in the human VH and Vκ sequences. FIG. 3C shows the difference between hImmu31 Vκ and two variants, hImmu31 VκT69 and hImmu31 VκT39. The DNA and amino acid sequences of hImmu31 VH and Vκ are shown in FIGS. 5A and 5B, respectively.

Example 6

Expression and Characterization of hImmu31

The strategy as described by Leung et al, (Leung et al., 1994) was used to construct the designed Vκ and VH genes for hImmu31 using a combination of long oligonucleotide syntheses and PCR. Each variable chain was constructed in two parts, a 5'- and 3'-half, designated as "A" and "B" respectively. Each half was produced by PCR amplification of a single strand synthetic oligonucleotide template with two short flanking primers, using Taq polymerase. The amplified fragments were first cloned into the pCR2.1 TA cloning vector from Invitrogen (Carlsbad, Calif.) and subjected to DNA sequencing. The templates and primer pairs are listed as follows:

| Template | Primers |
|---|---|
| hImmu31VHA | VHBACK/VHa |
| hImmu31VHB | VHb/VHFOR |
| hImmu31VKA | VKBACK/VKa |
| hImmu31VKB | VKb/VKFOR |
| hImmu31VH domain | |

For the construction of the hImmu31VH domain, two long oligonucleotides, hImmu31VHA (135-mer) and hImmu31VHB (151-mer) were synthesized on an automated DNA synthesizer (Applied Biosystem). The sequence of long oligo hImmu31VHA represents the minus strand of the hImmu31VH domain complementary to nt 28 to 162 and that of hImmu31VHB was complement to nt 181-331 as listed below.

```
hImmu31VHA (135 bp)                (SEQ ID NO. 18)
5'-GTAAGGATGA ATATATCCAA TCCAATACAG ACCCTGTCCA

GGTGCCTGCC TGACCCAGTG TATAACATAG CTAGTAAAAG

CGTAGCCAGA AGCCTTGCAG GAGACCTTCA CTGATGACCC

AGGTTTCTTG ACTTC-3' hImmu31VHB (151 bp)                (SEQ ID NO. 19)
5'-CTTGGCCCCA GTAAGCAAAA GGGTCTCCCC CCCCAGATCT

TGCACAAAAA TAAAATGCCG TGTCCTCAGA CCTCAGGCTG

CTCAGCTCCA TGTAGGCTGT ATTGGTGGAT TCGTCAGCTG

TTATTGTGGC CTTGCCTTTG AACTTCTCAT T-3'
``` hImmu31VHA was amplified by PCR with a pair of primers VHBACK and VHa, while hImmu31VHB was amplified with VHb and VHFOR. The sequences of these primers are listed below:

```
VHBACK                             (SEQ ID NO. 20)
5'-CAGCTGCAGC AATCAGGGGC TGAAGTCAAG AAACCTG-3'
```

```
                                              -continued
VHa                                           (SEQ ID NO. 21)
5'-GTACTTGGTA CCACCATTGT AAGGATGAAT ATATCC-3'

VHb                                           (SEQ ID NO. 22)
5'-AATGGTGGTA CCAAGTACAA TGAGAAGTTC AAAGGC-3'

VHFOR                                         (SEQ ID NO. 23)
5'-GGAGACGGTG ACCAGGGAGC CTTGGCCCCA GTAAGC-3'
``` where underlined sequences represent the restriction sites, PstI, KpnI, KpnI and BstEII, respectively. The resulting double-stranded PCR products, VHA and VHB, were digested with PstI/KpnI and KpnI/BstEII, respectively, gel purified, and assembled into the PstI/BstEII sites of the heavy chain staging vector, VHpBS, forming the full length hImmu31VH gene (FIG. 5A). The humanized VH sequence was subcloned into the pG1g vector, and the resultant human IgG1 heavy chain expression vector was designated as hImmu31pG1g.

hImmu31Vκ Domain

Similarly, for the construction of hImmu31Vκ domain, long oligonucleotides hImmu31VKA and hImmu31VKB were used as template to construct the Vκ gene. hImmu31VKA represents the minus strand of the hImmu31Vκ domain complementary to nt 23 to 135 and that of hImmu31VKB was complementary to nt 155-306 of the designed hImmu31Vκ (FIG. 5B).

```
hImmu31VKA (113 bp)                           (SEQ ID NO. 24)
5'-TTTAGGTGCT TTCCCTGGTT TCTGCTGGTA CCAACCTATA

TACTTGTTAA TGTCTTGGCT TGCCTTACAA GTGATAGTGA

CCCTATCTCC AACAGATGCG CTCAGAGATG ATG-3' hImmu31VKB (152 bp)                           (SEQ ID NO. 25)
5'-CTTGGTCCCT CCACCGAACG TCCACAGATC ATCATACTGT

AGACAATAAT ATGTTGCAAT GTCTTCTGGT TGAAGAGAGC

TGATGGTGAA AGTATAATCT GTCCCAGATC CGCTGCCAGA

GAATCGCGAA GGGATACCTG GCAGTAATGC AG-3'
``` hImmu31 VKA was PCR-amplified with the primer pair of VKBACK and VKa, while hImmu31VKB was amplified with VKb and VKFOR. The sequences of these primers are listed below:

```
VKBACK                                        (SEQ ID NO. 26)
5'-GAC ATT CAG CTG ACC CAG TCT CCA TCA TCT CTG AGC
GC-3'

VKa                                           (SEQ ID NO. 27)
5'-A TGT GTA ATG CAT CAG CAG TTT AGG TGC TTT CC-3'

VKb                                           (SEQ ID NO. 28)
5'-CTG CTG ATG CAT TAC ACA TCT GCA TTA CTG CCA
GG-3'

VKFOR                                         (SEQ ID NO. 29)
5'-GA CCG GCA GAT CTG CAG CTT GGT CCC TCC AC-3'
```

The underlined sequences in VKBACK, VKa, VKb, and VKFOR represent PvuII, NsiI, NsiI and BglII restriction sites, respectively. The resulting double-stranded PCR products, VKA and VKB, were digested with PvuII/NsiI and NsiI/BglII, respectively, gel purified, and assembled into the PvuII/BclI sites of the light chain staging vector, VKpBR.

Finally, the humanized Vκ sequence was subcloned into the light chain expression vector, pKh, forming hImmu31pKh.

hImmu31VκT39 and hImmu31VκT69 were similarly constructed and the final expression vectors for these two variants were hImmu31T39pKh and hImmu31T69pKh, respectively.

The Final Expression Vector for hImmu31

Using the two-expression vector system described above, i.e. pG1g and pKh, is preferred in the initial stage of humanization because it provides flexibility of testing various combinations of Vκ and VH constructs. The defective designs, if any, residing in the individual heavy or light chain can be systematically identified and corrected by mixing and matching each of the humanized chains with their chimeric partners. However, the transfected cells generated from the pG1g/pKh system typically produce antibodies at a level of less than 1 mg/liter of terminal culture. To generate high-level antibody-producing cell lines, a single expression vector, pdHL2, is preferred for the production of hImmu31. pdHL2 contains the expression cassettes for both human IgG heavy and light chains under the control of IgH enhancer and $MT_1$ promoter, as well as a mouse dhfr gene, controlled by a weak SV40 promotor, as a marker for selection of transfectants and co-amplification of the trans-genes (Gillies et al., *J Immunol. Methods* 125:191 (1989); Losman et al., *Cancer* 80:2660 (1997)). By replacing the Vκ and VH segments of pdHL2, different chimeric or humanized Abs can be expressed.

To construct the pdHL2 expression vector for hImmu31, hImmu31VH and Vκ gene segments were subcloned into another set of staging vectors, VHpBS2 and VKpBR2, respectively. VHpBS2 is a modified staging vector of VHpBS (Leung et al., Hybridoma, 13:469 (1994)), into which a XhoI restriction site was introduced at 16 bases upstream of the translation initiation codon. Similarly, VKpBR2 is a modified staging vector of VKpBR (Leung et al., Hybridoma, 13:469 (1994)), into which a XbaI restriction site was introduced at 14 bases upstream of the translation initiation codon. The final expression vector hImmu31pdHL2 was constructed by sequentially subcloning the XbaI-BamHI and XhoI/BamHI fragments of hImmu31Vκ and VH, respectively, into pdHL2. The final expression vector was designated as hImmu31pdHL2.

Expression and Binding Activity Assays for hImmu31

The methods for transfection, screening positive transfected clones and binding activity assays for hImmu31 were same as described for cImmu31 (see Example 3).

Figure 6:
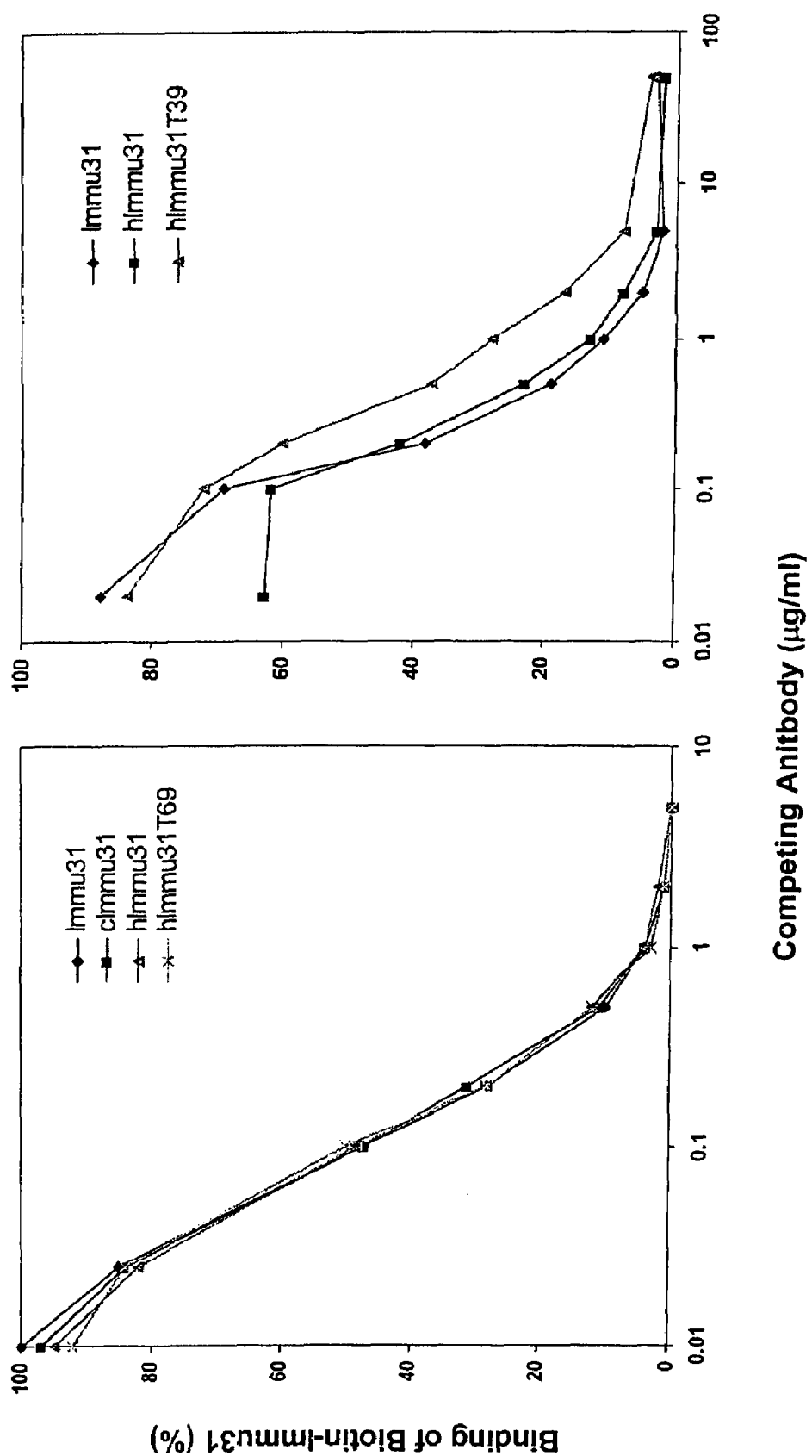
FIG. 6 shows the results of competitive cell surface binding assays to compare the binding affinity of hImmu31 and two variants, hImm31T39 and hImmu31T69, with that of murine and chimeric Immu31. Varying concentrations of a competing Ab, (hImmu31, hImm31 T39, hImmu31T69, cImmu31, or (murine) Immu31) was mixed with a constant amount of biotinylated murine Immu31 and incubated for 1 h in the wells of 96-well ELISA plate precoated with AFP. After washing, HRP-conjugated streptavidin was added and incubated for 1 h at room temperature. The amount of HRP-conjugated streptavidin bound to the AFP-bound biotinylated Immu31 was revealed by reading $OD_{490}$ after the addition of a substrate solution containing 4 mM ortho-phenylenediamine dihydrochloride and 0.04% $H_2O_2$. Chart A compares the binding affinity of hImmu31 (triangle) and hImmu31 T69 (cross) with cImmu31 (square) and Immu31 (diamond). The results showed that hImmu31, cImmu31 and Immu31 competed with biotin-Immu31 equally well for the binding to AFP, indicating the binding specificity and affinity of MAb Immu31 are preserved in the humanized Immu31. In addition, the binding affinity of hImmu31 T69 to AFP was shown to be comparable to other Immu31 Abs. Chart B compares hImmu31 T39 (triangle) with hImmu31 (square) and Immu31 (diamond). The binding affinity of hImmu31T39 was reduced significantly, indicating the importance of the charged residue 39K in Ag-binding.
Figure 7:
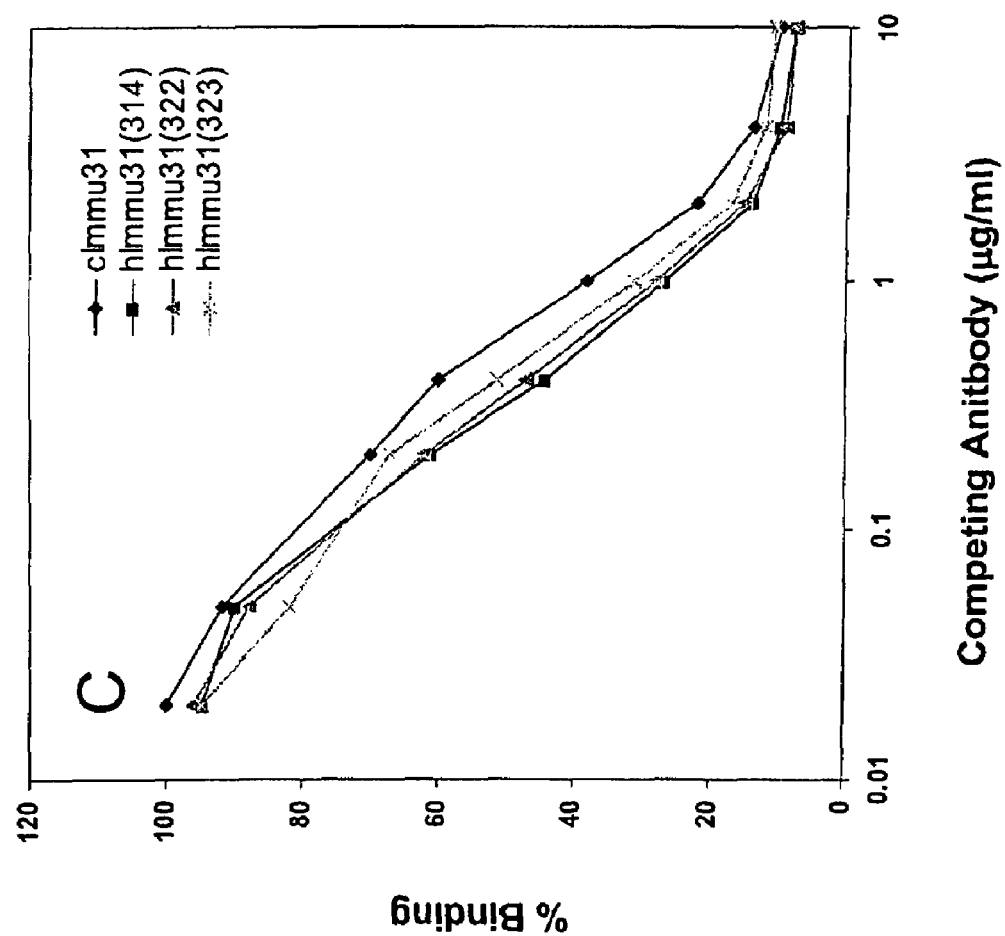
FIG. 7 shows the results of competitive cell surface binding assays to compare the binding affinity of hImmu31 expression using pdHL2 vector with that chimeric Immu31.

Three versions of the humanized Ab, hImmu31, hImmu31T39 and hImmu31T69, were expressed in Sp2/0 cells by co-transfection of the heavy chain expression vector, hImmu31pG1 g, with either of the kappa chain expression vectors: hImmu31pKh, hImmu31T39pKh or hImmu31T69pKh. The Ag-binding activities of these humanized Abs were evaluated by the same competitive binding assay. While the AFP binding affinity of hImmu31 and hImmu31T69 was similar to that of murine Immu31 or cImmu31, judging from their comparable competition with biotin-Immu31 (FIG. 6A), hImmu31T39 was somewhat inferior (FIG. 6B). These results demonstrated the successful humanization of Immu31 and revealed that the murine kappa chain FR residue $K^{39}$ but not $R^{69}$ is important for maintaining the immunoreactivity of Immu31.

The typical productivity of Abs from transfected Sp2/0 cells by using pKh and pG1g expression vector system is in the single digit range of milligram per liter, which is practically insufficient for production of large quantities of Abs for clinical applications. In the case of hImmu31, the highest productivity of the selected clone co-transfected with hImmu31 pKh and hImmu31pG1g was 2-3 mg/L. To increase the capability of the transfected cells to produce hImmu31, the heavy and kappa chain expression cassettes were re-constructed into one single expression vector, pdHL2, which contains the murine dhfr gene and allows for subsequent amplification of the transfected gene products with stepwise increase of MTX concentrations. Three hImmu31pdHL2 transfected clones, 314.2C11, 322.1G4 and 323.2H2, that were initially selected with 25 nM MTX and estimated to be producing 4, 15 and 8 mg/L of hImmu31, respectively, were subjected to amplification using procedures as described by Losman et al. (Cancer 80:2660 (1997)). As the MTX concentration in the cell culture medium gradually increased from 0.1 to 3 µM, the productivity of hImmu31 from these cells was increased concomitantly and finally exceeded 100 mg/L in termination roller bottle cultures (data not shown). The purified hImmu31 from hImmu31 pdHL2-transfected cells showed comparable immunoreactivity as that of its murine and chimeric counterparts (FIG. 6C).

Example 7

Therapy of a Patient with Hepatocelluar Carcinoma with Radiolabeled Humanized Anti-AFP Monoclonal Antibody A 57-year-old man presenting with jaundice, malaise, loss of weight, and general weakness, is diagnosed with an inoperable hepatocellular carcinoma that appears by computed tomography to extend about 6 em in diameter in the right lobe of the liver, and to also appear as a single 3-cm lesion in the left lobe. His serum AFP level at the time of presentation measures 150 ng/mL, with a 40% increase in his serum transaminase and bilirubin levels, and a 50% increase in his serum LDH level. The right lobe lesion is confirmed by biopsy to be hepatocellular carcinoma expressing AFP. The patient is then given two cycles of humanized Immu31 monoclonal antibody conjugated by DOTA with 90-Y, so that an infusion is administered for each therapy of a dose of 25 mCi (100 mg antibody protein). The first therapy is given in an outpatient setting, and is repeated 6 weeks later. Prior to each therapy, a diagnostic dose of 111-In conjugated by DOTA to the antibody is also injected in order to demonstrate tumor targeting and to estimate the radiation dose delivered to the tumor and to other normal tissues, such as liver, kidney and bone marrow, so that the therapeutic dose with 90-Y, given a week later, can be adjusted so as not to induce normal tissue/organ toxicity beyond what is considered tolerable (e.g., 2000 cGy to kidneys). The patient is then monitored for response by repeated computer tomography scans every 4-8 weeks post therapy, as well as by serum AFP, bilirubin, transaminase, and LDH levels. Eight weeks after the second therapeutic administration of the 90-Y-labeled antibody, his serum levels of bilirubin, transaminases, and LDH decreases to about 20% above normal, and his serum AFP titer is measured at 60 ng/mL, which also constitutes an improvement. CT measurements of his liver disease shows an almost complete disappearance of the left lobe lesion and a 40% reduction of the larger mass in the right lobe. The patient then became a candidate for surgical resection of his right lobe, since it is considered that the remaining small lesion in the left lobe is not cancer, but scar tissue. This is further confirmed by a diagnostic study performed with 111-In-labeled Immu31 antibody, which shows uptake in the right lobe mass but not in the left lobe, thus indicating that no AFP-expressing disease is in the left lobe.

All of the publications and patent applications and patents cited in this specification are herein incorporated in their entirety by reference.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. An isolated antibody or fragment thereof that binds an alpha-fetoprotein (AFP) antigen, the antibody or fragment thereof comprising the heavy chain CDR1 (SYVIH, SEQ ID NO:4), CDR2 (YIHPYNGGTKYNEKFKG, SEQ ID NO:5) and CDR3 (SGGGDPFAY, SEQ ID NO:6) and the light chain CDR1 (KASQDINKYIG, SEQ ID NO: 1), CDR2 (YTSALLP, SEQ ID NO:2) and CDR3 (LQYDDLWT, SEQ ID NO:3) sequences of the Immu31 antibody.

2. The antibody or fragment thereof of claim 1, wherein said antibody or fragment thereof is humanized.

3. The antibody or fragment thereof of claim 1, wherein said antibody or fragment thereof is chimeric.

4. The humanized antibody or fragment thereof of claim 2, comprising the framework (FR) regions of the light and heavy chain variable regions of a human antibody and the light and heavy chain constant regions of a human antibody.

5. The humanized antibody or fragment thereof of claim 4, wherein the FRs of the light and heavy chain variable regions of said antibody or fragment thereof comprise at least one amino acid substituted from the corresponding position(s) in the FRs of the murine Immu31 anti-AFP antibody.

6. The humanized antibody or fragment thereof of claim 5, wherein said amino acid from said murine Immu31 antibody is at least one amino acid selected from the group consisting of amino acid residues 5, 27, 28, 30, 46, 48, 66, 67 and 94 of the murine Immu31 heavy chain variable region (SEQ ID NO:31).

7. The humanized antibody or fragment thereof of claim 5, wherein said amino acid from said murine Immu31 antibody is at least one amino acid selected from the group consisting of amino acid residues 4, 39, 48, 49, 58, 69, 100 and 107 of the murine Immu31 light chain variable region (SEQ ID NO:33).

8. The chimeric antibody or fragment thereof of claim 3, wherein said antibody or fragment thereof comprises the cImmu31 VK amino acid sequence of SEQ ID NO:37.

9. The chimeric antibody or fragment thereof of claim 3, wherein said antibody or fragment thereof comprises the cImmu31 VH amino acid sequence of SEQ ID NO:35.

10. The humanized antibody or fragment thereof of claim 2, wherein said antibody or fragment thereof comprises a hImmu31 VK amino acid sequence of SEQ ID NO:42.

11. The humanized antibody or fragment thereof of claim 2, wherein said antibody or fragment thereof comprises a hImmu31 VH amino acid sequence of SEQ ID NO:40.

12. The antibody or fragment thereof of claim 1, wherein said fragment is selected from the group consisting of Fv, F(ab')2, Fab' and Fab.

13. The antibody or fragment thereof of claim 1, wherein said antibody or fragment is a naked antibody or fragment.

14. The antibody or fragment thereof of claim 1, wherein said antibody or fragment is conjugated to at least one diagnostic/detection agent or at least one therapeutic agent.

15. The antibody or fragment thereof of claim 14, wherein said diagnostic/detection agent is selected from the group consisting of a photoactive agent, a chromagen, a dye, a radionuclide, a contrast agent, a paramagnetic ion, an ultrasound-enhancing agent, a liposome and a radiopaque compound.

16. The antibody or fragment thereof of claim 14, wherein said therapeutic agent is selected from the group consisting of a radionuclide, boron, gadolinium or uranium atoms, an immunomodulator, a cytokine, a hormone, a hormone antagonist, an enzyme, an enzyme inhibitor, a photoactive therapeutic agent, a drug, a cytotoxic agent, a toxin, an angiogenesis inhibitor and a different antibody.

17. The antibody or fragment thereof of claim 16, wherein said drug is selected from the group consisting of antimitotic, alkylating, antimetabolite, anti-angiogenesis, apoptotic, alkaloid, COX-2-inhibiting agents, antibiotic agents, nitrogen mustards, ethylenimine derivatives, alkyl sulfonates, nitrosoureas, triazenes, folic acid analogs, anthracyclines, taxanes, COX-2 inhibitors, pyrimidine analogs, purine analogs, antibiotics, enzymes, epipodophyllotoxins, platinum coordination complexes, vinca alkaloids, substituted ureas, methyl hydrazine derivatives, adrenocortical suppressants, hormone antagonists, enzyme inhibitors, endostatin, taxols and other taxanes, camptothecins and doxorubicins.

18. The antibody or fragment thereof of claim 16, wherein said toxin is selected from the group consisting of ricin, abrin, alpha toxin, saporin, ribonuclease (RNase), DNase I, Staphylococcal enterotoxin-A, pokeweed antiviral protein, gelonin, diphtherin toxin, *Pseudomonas* exotoxin, and *Pseudomonas* endotoxin.

19. The antibody or fragment thereof of claim 18 wherein said therapeutic agent is a ribonuclease.

20. The antibody or fragment thereof of claim 16, wherein said immunomodulator is selected from the group consisting of a cytokine, a stem cell growth factor, a lymphotoxin, a hematopoietic factor, a colony stimulating factor (CSF), an interferon (IFN), a stem cell growth factor, erythropoietin, thrombopoietin.

21. The antibody or fragment thereof of claim 20, wherein said lymphotoxin is tumor necrosis factor (TNF), said hematopoietic factor is an interleukin (IL), said colony stimulating factor is granulocyte-colony stimulating factor (G-CSF) or granulocyte macrophage-colony stimulating factor (GM-CSF)), said interferon is interferons-α, -β or -γ and said stem cell growth factor is designated "Si factor".

22. The antibody or fragment thereof of claim 20, wherein said cytokine is selected from the group consisting of IL-1, IL-2, IL-3, IL-6, IL-10, IL-12, IL-18, interferon-γ and TNF-α.

23. The antibody or fragment thereof of claim 16, wherein said radionuclide is selected from the group consisting of P-32, P-33, Sc-47, Fe-59, Cu-64, Cu-67, Se-75, As-77, Sr-89, Y-90, Mo-99, Rh-105, Pd-109, Ag-111, I-125, I-131, Pr-142, Pr-143, Pm-149, Sm-153, Tb-161, Ho-166, Er-169, Lu-177, Re-186, Re-188, Re-189, Ir-194, Au-198, Au-199, Pb-211, Pb-212, Bi-213, Co-58, Ga-67, Br-80m, Tc-99m, Rh-103m, Pt-109, In-111, Sb-119, Ho-161, Os-189m, Ir-192, Dy-152, At-211, Bi-212, Ra-223, Rn-219, Po-215, Bi-211, Ac-225, Fr-221, At-217, and Fm-255.

24. The antibody or fragment thereof of claim 14, wherein said diagnostic/detection or therapeutic agent is bound to said antibody or fragment thereof by means of a carbohydrate moiety.

25. An antibody fusion protein comprising at least one anti-AFP antibody or fragment thereof according to claim 1.

26. The antibody or fragment thereof of claim 1, wherein said antibody or fragment thereof is murine.

* * * * *

SEQUENCE LISTING

```
<160> NUMBER OF SEQ ID NOS: 48

<210> SEQ ID NO 1
<211> LENGTH: 11
<212> TYPE: PRT
<213> ORGANISM: Mus sp.

<400> SEQUENCE: 1

Lys Ala Ser Gln Asp Ile Asn Lys Tyr Ile Gly
 1               5                   10

<210> SEQ ID NO 2
<211> LENGTH: 7
<212> TYPE: PRT
<213> ORGANISM: Mus sp.

<400> SEQUENCE: 2

Tyr Thr Ser Ala Leu Leu Pro
 1               5
```

```
<210> SEQ ID NO 3
<211> LENGTH: 8
<212> TYPE: PRT
<213> ORGANISM: Mus sp.

<400> SEQUENCE: 3

Leu Gln Tyr Asp Asp Leu Trp Thr
 1               5

<210> SEQ ID NO 4
<211> LENGTH: 5
<212> TYPE: PRT
<213> ORGANISM: Mus sp.

<400> SEQUENCE: 4

Ser Tyr Val Ile His
 1               5

<210> SEQ ID NO 5
<211> LENGTH: 17
<212> TYPE: PRT
<213> ORGANISM: Mus sp.

<400> SEQUENCE: 5

Tyr Ile His Pro Tyr Asn Gly Gly Thr Lys Tyr Asn Glu Lys Phe Lys
 1               5                  10                  15

Gly

<210> SEQ ID NO 6
<211> LENGTH: 9
<212> TYPE: PRT
<213> ORGANISM: Mus sp.

<400> SEQUENCE: 6

Ser Gly Gly Gly Asp Pro Phe Ala Tyr
 1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Lys(HSG)
<220> FEATURE:
<221> NAME/KEY: MOD_RES
<222> LOCATION: (4)
<223> OTHER INFORMATION: Lys(HSG)
<220> FEATURE:
<223> OTHER INFORMATION: c-term amidation

<400> SEQUENCE: 7

Phe Lys Tyr Lys
 1

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Primer

<400> SEQUENCE: 8
```
acagtcactg agctgg                                                  16

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 9
gccggatcct gactggatgg tgggaagatg gataca                            36

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 10
gacattcagc tgacccagtc tcca                                         24

<210> SEQ ID NO 11
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 11
ctcactggat ggtgggaaga tggatacagt tgg                               33

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
aggtsacarc tgcagsagtc wgg                                          23

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 13
agactgcagg agagctggga aggtgtgcac                                   30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Probe

<400> SEQUENCE: 14
gaagcacacg actgaggcac ctccagatgt                                   30

<210> SEQ ID NO 15
<211> LENGTH: 15
<212> TYPE: PRT
<213> ORGANISM: Artificial Sequence

```
<220> FEATURE:
<223> OTHER INFORMATION: Description of Artificial Sequence: Linker
      peptide

<400> SEQUENCE: 15

Gly Gly Gly Gly Ser Gly Gly Gly Gly Ser Gly Gly Gly Gly Ser
 1               5                  10                  15

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Lys(DTPA)
<220> FEATURE:
<221> NAME/KEY: MOD_RES
<222> LOCATION: (3)
<223> OTHER INFORMATION: Lys(DTPA)
<220> FEATURE:
<221> NAME/KEY: MOD_RES
<222> LOCATION: (4)
<223> OTHER INFORMATION: Lys(Tscg-Cys); Cys not part of peptide backbone
<220> FEATURE:
<223> OTHER INFORMATION: c-term amidated

<400> SEQUENCE: 16

Lys Tyr Lys Lys
 1

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 17
agctgggaag gtgtgcac                                                   18

<210> SEQ ID NO 18
<211> LENGTH: 135
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gtaaggatga atatatccaa tccaatacag accctgtcca ggtgcctgcc tgacccagtg     60
tataacatag ctagtaaaag cgtagccaga agccttgcag gagaccttca ctgatgaccc    120
aggtttcttg acttc                                                    135

<210> SEQ ID NO 19
<211> LENGTH: 151
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cttggcccca gtaagcaaaa gggtctcccc ccccagatct tgcacaaaaa taaaatgccg     60
```

```
tgtcctcaga cctcaggctg ctcagctcca tgtaggctgt attggtggat cgtcagctg      120 ttattgtggc cttgcctttg aacttctcat t                                    151
```

<210> SEQ ID NO 20
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 20

```
cagctgcagc aatcaggggc tgaagtcaag aaacctg                              37
```

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 21

```
gtacttggta ccaccattgt aaggatgaat atatcc                               36
```

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 22

```
aatggtggta ccaagtacaa tgagaagttc aaaggc                               36
```

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 23

```
ggagacggtg accagggagc cttggcccca gtaagc                               36
```

<210> SEQ ID NO 24
<211> LENGTH: 113
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24

```
tttaggtgct ttccctggtt tctgctggta ccaacctata tacttgttaa tgtcttggct     60
tgccttacaa gtgatagtga ccctatctcc aacagatgcg ctcagagatg atg            113
```

<210> SEQ ID NO 25
<211> LENGTH: 152
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25

```
cttggtccct ccaccgaacg tccacagatc atcatactgt agacaataat atgttgcaat     60
```

-continued gtcttctggt tgaagagagc tgatggtgaa agtataatct gtcccagatc cgctgccaga    120
gaatcgcgaa gggatacctg gcagtaatgc ag    152

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 26
gacattcagc tgacccagtc tccatcatct ctgagcgc    38

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 27
atgtgtaatg catcagcagt ttaggtgctt tcc    33

<210> SEQ ID NO 28
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 28
ctgctgatgc attacacatc tgcattactg ccagg    35

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 29
gaccggcaga tctgcagctt ggtccctcca c    31

<210> SEQ ID NO 30
<211> LENGTH: 351
<212> TYPE: DNA
<213> ORGANISM: Artificial Sequence
<220> FEATURE:
<221> NAME/KEY: CDS
<222> LOCATION: (1)..(351)
<220> FEATURE:
<223> OTHER INFORMATION: Description of Artificial Sequence: Synthetic
      Immu31Vh nucleotide sequence

<400> SEQUENCE: 30 gtg aag ctg cag gag tca gga cct gaa ctg gta aag cct ggg gct tca    48
Val Lys Leu Gln Glu Ser Gly Pro Glu Leu Val Lys Pro Gly Ala Ser
 1               5                  10                  15 gtg aag atg tcc tgc aag gct tct gga tac gct ttc act agc tat gtt    96
Val Lys Met Ser Cys Lys Ala Ser Gly Tyr Ala Phe Thr Ser Tyr Val
            20                  25                  30 ata cac tgg gtg agg cag aag cct ggg cag ggc ctt tat tgg att gga    144
Ile His Trp Val Arg Gln Lys Pro Gly Gln Gly Leu Tyr Trp Ile Gly
        35                  40                  45

```
tat att cat cct tac aat ggt ggt acc aag tac aat gag aag ttc aaa      192
Tyr Ile His Pro Tyr Asn Gly Gly Thr Lys Tyr Asn Glu Lys Phe Lys
     50                  55                  60 ggc aag gcc aca ctg act tca gac aaa tcg tcc agc aca acc tac atg      240
Gly Lys Ala Thr Leu Thr Ser Asp Lys Ser Ser Ser Thr Thr Tyr Met
 65                  70                  75                  80 gag ctc agc agc ctg acc tct gag gac tct gcg gtc tat tac tgt gca      288
Glu Leu Ser Ser Leu Thr Ser Glu Asp Ser Ala Val Tyr Tyr Cys Ala
                 85                  90                  95 aga tct ggg ggg gga gac cct ttt gct tac tgg ggc caa ggg act ctg      336
Arg Ser Gly Gly Gly Asp Pro Phe Ala Tyr Trp Gly Gln Gly Thr Leu
            100                 105                 110 gtc act gtc tct gca                                                  351
Val Thr Val Ser Ala
        115

<210> SEQ ID NO 31
<211> LENGTH: 117
<212> TYPE: PRT
<213> ORGANISM: Artificial Sequence
<220> FEATURE:
<223> OTHER INFORMATION: Description of Artificial Sequence: Synthetic
      Immu31Vh protein sequence

<400> SEQUENCE: 31

Val Lys Leu Gln Glu Ser Gly Pro Glu Leu Val Lys Pro Gly Ala Ser
 1               5                  10                  15

Val Lys Met Ser Cys Lys Ala Ser Gly Tyr Ala Phe Thr Ser Tyr Val
             20                  25                  30

Ile His Trp Val Arg Gln Lys Pro Gly Gln Gly Leu Tyr Trp Ile Gly
         35                  40                  45

Tyr Ile His Pro Tyr Asn Gly Gly Thr Lys Tyr Asn Glu Lys Phe Lys
     50                  55                  60

Gly Lys Ala Thr Leu Thr Ser Asp Lys Ser Ser Ser Thr Thr Tyr Met
 65                  70                  75                  80

Glu Leu Ser Ser Leu Thr Ser Glu Asp Ser Ala Val Tyr Tyr Cys Ala
                 85                  90                  95

Arg Ser Gly Gly Gly Asp Pro Phe Ala Tyr Trp Gly Gln Gly Thr Leu
            100                 105                 110

Val Thr Val Ser Ala
        115

<210> SEQ ID NO 32
<211> LENGTH: 321
<212> TYPE: DNA
<213> ORGANISM: Artificial Sequence
<220> FEATURE:
<221> NAME/KEY: CDS
<222> LOCATION: (1)..(321)
<220> FEATURE:
<223> OTHER INFORMATION: Description of Artificial Sequence: Synthetic
      Immu31Vk nucleotide sequence

<400> SEQUENCE: 32 gac att cag ctg acc cag tct cca tcc tca ctg tct gca tct ctg gga      48
Asp Ile Gln Leu Thr Gln Ser Pro Ser Ser Leu Ser Ala Ser Leu Gly
 1               5                  10                  15 ggc aaa gtc acc atc act tgc aag gca agc caa gac att aac aag tat      96
Gly Lys Val Thr Ile Thr Cys Lys Ala Ser Gln Asp Ile Asn Lys Tyr
             20                  25                  30 ata ggt tgg tac caa cac aag cct gga aaa ggt cct agg cta ctc atg      144
Ile Gly Trp Tyr Gln His Lys Pro Gly Lys Gly Pro Arg Leu Leu Met
```

```
                    35                  40                  45
cat tac aca tct gca tta ctg cca ggc atc cca tca agg ttc agt gga      192
His Tyr Thr Ser Ala Leu Leu Pro Gly Ile Pro Ser Arg Phe Ser Gly
     50                  55                  60 agt ggg tct ggg aga gat tat tcc ttc agc atc agc aac ctg gag cct      240
Ser Gly Ser Gly Arg Asp Tyr Ser Phe Ser Ile Ser Asn Leu Glu Pro
 65                  70                  75                  80 gaa gat att gca act tat tat tgt cta cag tat gat gat ctg tgg acg      288
Glu Asp Ile Ala Thr Tyr Tyr Cys Leu Gln Tyr Asp Asp Leu Trp Thr
                 85                  90                  95 ttc ggt gga ggc acc aag ctg gaa atg aaa cgg                          321
Phe Gly Gly Gly Thr Lys Leu Glu Met Lys Arg
            100                 105

<210> SEQ ID NO 33
<211> LENGTH: 107
<212> TYPE: PRT
<213> ORGANISM: Artificial Sequence
<220> FEATURE:
<223> OTHER INFORMATION: Description of Artificial Sequence: Synthetic
      Immu31Vk protein sequence

<400> SEQUENCE: 33

Asp Ile Gln Leu Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
             20                  25                  30

Ile Gly Trp Tyr Gln His Lys Pro Gly Lys Pro Arg Leu Leu Met
         35                  40                  45

His Tyr Thr Ser Ala Leu Leu Pro Gly Ile Pro Ser Arg Phe Ser Gly
     50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asp Leu Trp Thr
                 85                  90                  95

Phe Gly Gly Gly Thr Lys Leu Glu Met Lys Arg
            100                 105

<210> SEQ ID NO 34
<211> LENGTH: 354
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic
      cImmu31Vh nucleotide sequence

<400> SEQUENCE: 34 cag gtc cag ctg cag gag tca gga cct gaa ctg gta aag cct ggg gct      48
Gln Val Gln Leu Gln Glu Ser Gly Pro Glu Leu Val Lys Pro Gly Ala
 1               5                  10                  15 tca gtg aag atg tcc tgc aag gct tct gga tac gct ttc act agc tat      96
Ser Val Lys Met Ser Cys Lys Ala Ser Gly Tyr Ala Phe Thr Ser Tyr
             20                  25                  30 gtt ata cac tgg gtg agg cag aag cct ggg cag ggc ctt tat tgg att      144
Val Ile His Trp Val Arg Gln Lys Pro Gly Gln Gly Leu Tyr Trp Ile
         35                  40                  45 gga tat att cat cct tac aat ggt ggt acc aag tac aat gag aag ttc      192
Gly Tyr Ile His Pro Tyr Asn Gly Gly Thr Lys Tyr Asn Glu Lys Phe
     50                  55                  60
```

```
aaa ggc aag gcc aca ctg act tca gac aaa tcg tcc agc aca acc tac      240
Lys Gly Lys Ala Thr Leu Thr Ser Asp Lys Ser Ser Ser Thr Thr Tyr
 65                  70                  75                  80 atg gag ctc agc agc ctg acc tct gag gac tct gcg gtc tat tac tgt      288
Met Glu Leu Ser Ser Leu Thr Ser Glu Asp Ser Ala Val Tyr Tyr Cys
                 85                  90                  95 gca aga tct ggg ggg gga gac cct ttt gct tac tgg ggc caa ggg acc      336
Ala Arg Ser Gly Gly Gly Asp Pro Phe Ala Tyr Trp Gly Gln Gly Thr
            100                 105                 110 acg gtc acc gtc tcc tca                                              354
Thr Val Thr Val Ser Ser
        115
```

<210> SEQ ID NO 35
<211> LENGTH: 118
<212> TYPE: PRT
<213> ORGANISM: Artificial Sequence
<220> FEATURE:
<223> OTHER INFORMATION: Description of Artificial Sequence: Synthetic
      cImmu31Vh protein sequence

<400> SEQUENCE: 35

```
Gln Val Gln Leu Gln Glu Ser Gly Pro Glu Leu Val Lys Pro Gly Ala
 1               5                  10                  15

Ser Val Lys Met Ser Cys Lys Ala Ser Gly Tyr Ala Phe Thr Ser Tyr
            20                  25                  30

Val Ile His Trp Val Arg Gln Lys Pro Gly Gln Gly Leu Tyr Trp Ile
        35                  40                  45

Gly Tyr Ile His Pro Tyr Asn Gly Gly Thr Lys Tyr Asn Glu Lys Phe
    50                  55                  60

Lys Gly Lys Ala Thr Leu Thr Ser Asp Lys Ser Ser Ser Thr Thr Tyr
 65                  70                  75                  80

Met Glu Leu Ser Ser Leu Thr Ser Glu Asp Ser Ala Val Tyr Tyr Cys
                 85                  90                  95

Ala Arg Ser Gly Gly Gly Asp Pro Phe Ala Tyr Trp Gly Gln Gly Thr
            100                 105                 110

Thr Val Thr Val Ser Ser
        115
```

<210> SEQ ID NO 36
<211> LENGTH: 321
<212> TYPE: DNA
<213> ORGANISM: Artificial Sequence
<220> FEATURE:
<221> NAME/KEY: CDS
<222> LOCATION: (1)..(321)
<220> FEATURE:
<223> OTHER INFORMATION: Description of Artificial Sequence: Synthetic
      cImmu31Vk nucleotide sequence

<400> SEQUENCE: 36

```
gac atc cag ctg acc cag tct cca tcc tca ctg tct gca tct ctg gga       48
Asp Ile Gln Leu Thr Gln Ser Pro Ser Ser Leu Ser Ala Ser Leu Gly
 1               5                  10                  15 ggc aaa gtc acc atc act tgc aag gca agc caa gac att aac aag tat       96
Gly Lys Val Thr Ile Thr Cys Lys Ala Ser Gln Asp Ile Asn Lys Tyr
            20                  25                  30 ata ggt tgg tac caa cac aag cct gga aaa ggt cct agg cta ctc atg      144
Ile Gly Trp Tyr Gln His Lys Pro Gly Lys Gly Pro Arg Leu Leu Met
        35                  40                  45 cat tac aca tct gca tta ctg cca ggc atc cca tca agg ttc agt gga      192
His Tyr Thr Ser Ala Leu Leu Pro Gly Ile Pro Ser Arg Phe Ser Gly
```

```
His Tyr Thr Ser Ala Leu Leu Pro Gly Ile Pro Ser Arg Phe Ser Gly
            50                  55                  60 agt ggg tct ggg aga gat tat tcc ttc agc atc agc aac ctg gag cct    240
Ser Gly Ser Gly Arg Asp Tyr Ser Phe Ser Ile Ser Asn Leu Glu Pro
 65                  70                  75                  80 gaa gat att gca act tat tat tgt cta cag tat gat gat ctg tgg acg    288
Glu Asp Ile Ala Thr Tyr Tyr Cys Leu Gln Tyr Asp Asp Leu Trp Thr
                 85                  90                  95 ttc ggt gga ggg acc aag ctg gag atc aaa cga                        321
Phe Gly Gly Gly Thr Lys Leu Glu Ile Lys Arg
                100                 105

<210> SEQ ID NO 37
<211> LENGTH: 107
<212> TYPE: PRT
<213> ORGANISM: Artificial Sequence
<220> FEATURE:
<223> OTHER INFORMATION: Description of Artificial Sequence: Synthetic
      cImmu31Vk protein sequence

<400> SEQUENCE: 37

Asp Ile Gln Leu Thr Gln Ser Pro Ser Ser Leu Ser Ala Ser Leu Gly
 1               5                  10                  15

Gly Lys Val Thr Ile Thr Cys Lys Ala Ser Gln Asp Ile Asn Lys Tyr
                20                  25                  30

Ile Gly Trp Tyr Gln His Lys Pro Gly Lys Gly Pro Arg Leu Leu Met
            35                  40                  45

His Tyr Thr Ser Ala Leu Leu Pro Gly Ile Pro Ser Arg Phe Ser Gly
        50                  55                  60

Ser Gly Ser Gly Arg Asp Tyr Ser Phe Ser Ile Ser Asn Leu Glu Pro
 65                  70                  75                  80

Glu Asp Ile Ala Thr Tyr Tyr Cys Leu Gln Tyr Asp Asp Leu Trp Thr
                 85                  90                  95

Phe Gly Gly Gly Thr Lys Leu Glu Ile Lys Arg
                100                 105

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: EUVH
      protein sequence

<400> SEQUENCE: 38

Pro Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Arg Ser
                20                  25                  30

Ala Ile Ile Trp Val Arg Gln Ala Pro Gly Gln Gly Leu Glu Trp Met
            35                  40                  45

Gly Gly Ile Val Pro Met Phe Gly Pro Pro Asn Tyr Ala Gln Lys Phe
        50                  55                  60

Gln Gly Arg Val Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Gly Gly Tyr Gly Ile Tyr Ser Pro Glu Glu Tyr Asn Gly Gly Leu
                100                 105                 110
```

```
<210> SEQ ID NO 39
<211> LENGTH: 354
<212> TYPE: DNA
<213> ORGANISM: Artificial Sequence
<220> FEATURE:
<221> NAME/KEY: CDS
<222> LOCATION: (1)..(354)
<220> FEATURE:
<223> OTHER INFORMATION: Description of Artificial Sequence: Synthetic
      hImmu31Vh nucleotide sequence

<400> SEQUENCE: 39 cag gtc cag ctg cag caa tca ggg gct gaa gtc aag aaa cct ggg tca        48
Gln Val Gln Leu Gln Gln Ser Gly Ala Glu Val Lys Lys Pro Gly Ser
  1               5                  10                  15 tca gtg aag gtc tcc tgc aag gct tct ggc tac gct ttt act agc tat        96
Ser Val Lys Val Ser Cys Lys Ala Ser Gly Tyr Ala Phe Thr Ser Tyr
             20                  25                  30 gtt ata cac tgg gtc agg cag gca cct gga cag ggt ctg tat tgg att       144
Val Ile His Trp Val Arg Gln Ala Pro Gly Gln Gly Leu Tyr Trp Ile
         35                  40                  45 gga tat att cat cct tac aat ggt ggt acc aag tac aat gag aag ttc       192
Gly Tyr Ile His Pro Tyr Asn Gly Gly Thr Lys Tyr Asn Glu Lys Phe
     50                  55                  60 aaa ggc aag gcc aca ata aca gct gac gaa tcc acc aat aca gcc tac       240
Lys Gly Lys Ala Thr Ile Thr Ala Asp Glu Ser Thr Asn Thr Ala Tyr
 65                  70                  75                  80 atg gag ctg agc agc ctg agg tct gag gac acg gca ttt tat ttt tgt       288
Met Glu Leu Ser Ser Leu Arg Ser Glu Asp Thr Ala Phe Tyr Phe Cys
                 85                  90                  95 gca aga tct ggg ggg gga gac cct ttt gct tac tgg ggc caa ggc tcc       336
Ala Arg Ser Gly Gly Gly Asp Pro Phe Ala Tyr Trp Gly Gln Gly Ser
            100                 105                 110 ctg gtc acc gtc tcc tca                                               354
Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Description of Artificial Sequence: Synthetic
      hImmu31Vh protein sequence

<400> SEQUENCE: 40

Gln Val Gln Leu Gln Gln Ser Gly Ala Glu Val Lys Lys Pro Gly Ser
  1               5                  10                  15

Ser Val Lys Val Ser Cys Lys Ala Ser Gly Tyr Ala Phe Thr Ser Tyr
             20                  25                  30

Val Ile His Trp Val Arg Gln Ala Pro Gly Gln Gly Leu Tyr Trp Ile
         35                  40                  45

Gly Tyr Ile His Pro Tyr Asn Gly Gly Thr Lys Tyr Asn Glu Lys Phe
     50                  55                  60

Lys Gly Lys Ala Thr Ile Thr Ala Asp Glu Ser Thr Asn Thr Ala Tyr
 65                  70                  75                  80

Met Glu Leu Ser Ser Leu Arg Ser Glu Asp Thr Ala Phe Tyr Phe Cys
                 85                  90                  95

Ala Arg Ser Gly Gly Gly Asp Pro Phe Ala Tyr Trp Gly Gln Gly Ser
```

100             105             110
Leu Val Thr Val Ser Ser
        115

<210> SEQ ID NO 41
<211> LENGTH: 321
<212> TYPE: DNA
<213> ORGANISM: Artificial Sequence
<220> FEATURE:
<221> NAME/KEY: CDS
<222> LOCATION: (1)..(321)
<220> FEATURE:
<223> OTHER INFORMATION: Description of Artificial Sequence: Synthetic
      hImmu31Vk nucleotide sequence

<400> SEQUENCE: 41 gac atc cag ctg acc cag tct cca tca tct ctg agc gca tct gtt gga        48
Asp Ile Gln Leu Thr Gln Ser Pro Ser Ser Leu Ser Ala Ser Val Gly
  1               5                  10                  15 gat agg gtc act atc act tgt aag gca agc caa gac att aac aag tat        96
Asp Arg Val Thr Ile Thr Cys Lys Ala Ser Gln Asp Ile Asn Lys Tyr
             20                  25                  30 ata ggt tgg tac cag cag aaa cca ggg aaa gca cct aaa ctg ctg atg       144
Ile Gly Trp Tyr Gln Gln Lys Pro Gly Lys Ala Pro Lys Leu Leu Met
         35                  40                  45 cat tac aca tct gca tta ctg cca ggt atc cct tcg cga ttc tct ggc       192
His Tyr Thr Ser Ala Leu Leu Pro Gly Ile Pro Ser Arg Phe Ser Gly
     50                  55                  60 agc gga tct ggg aca gat tat act ttc acc atc agc tct ctt caa cca       240
Ser Gly Ser Gly Thr Asp Tyr Thr Phe Thr Ile Ser Ser Leu Gln Pro
 65                  70                  75                  80 gaa gac att gca aca tat tat tgt cta cag tat gat gat ctg tgg acg       288
Glu Asp Ile Ala Thr Tyr Tyr Cys Leu Gln Tyr Asp Asp Leu Trp Thr
                 85                  90                  95 ttc ggt gga ggg acc aag ctg cag atc aaa cga                           321
Phe Gly Gly Gly Thr Lys Leu Gln Ile Lys Arg
            100                 105

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Synthetic
      hImmu31Vk protein sequence

<400> SEQUENCE: 42

Asp Ile Gln Leu Thr Gln Ser Pro Ser Ser Leu Ser Ala Ser Val Gly
  1               5                  10                  15

Asp Arg Val Thr Ile Thr Cys Lys Ala Ser Gln Asp Ile Asn Lys Tyr
             20                  25                  30

Ile Gly Trp Tyr Gln Gln Lys Pro Gly Lys Ala Pro Lys Leu Leu Met
         35                  40                  45

His Tyr Thr Ser Ala Leu Leu Pro Gly Ile Pro Ser Arg Phe Ser Gly
     50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Leu Gln Tyr Asp Asp Leu Trp Thr
                 85                  90                  95

Phe Gly Gly Gly Thr Lys Leu Gln Ile Lys Arg
            100                 105

```
<210> SEQ ID NO 43
<211> LENGTH: 108
<212> TYPE: PRT
<213> ORGANISM: Artificial Sequence
<220> FEATURE:
<223> OTHER INFORMATION: Description of Artificial Sequence: REI protein
      sequence

<400> SEQUENCE: 43

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
        35                  40                  45

Tyr Glu Ala Ser Asn Leu Gln Ala Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr Arg
            100                 105

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide NEWMVH

<400> SEQUENCE: 44

Trp Gly Gln Gly Ser Leu Val Thr Val Ser Ser
 1               5                  10

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence:
      hImmu31VkT69 protein sequence

<400> SEQUENCE: 45

Asp Ile Gln Leu Thr Gln Ser Pro Ser Ser Leu Ser Ala Ser Val Gly
 1               5                  10                  15

Asp Arg Val Thr Ile Thr Cys Lys Ala Ser Gln Asp Ile Asn Lys Tyr
            20                  25                  30

Ile Gly Trp Tyr Gln Gln Lys Pro Gly Lys Ala Pro Lys Leu Leu Met
        35                  40                  45

His Tyr Thr Ser Ala Leu Leu Pro Gly Ile Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Leu Gln Tyr Asp Asp Leu Trp Thr
                85                  90                  95

Phe Gly Gly Gly Thr Lys Leu Gln Ile Lys Arg
            100                 105
```

```
<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence:
      hImmu31VkT39 protein sequence

<400> SEQUENCE: 46

Asp Ile Gln Leu Thr Gln Ser Pro Ser Ser Leu Ser Ala Ser Val Gly
  1               5                  10                  15

Asp Arg Val Thr Ile Thr Cys Lys Ala Ser Gln Asp Ile Asn Lys Tyr
             20                  25                  30

Ile Gly Trp Tyr Gln Gln Thr Pro Gly Lys Ala Pro Lys Leu Leu Met
         35                  40                  45

His Tyr Thr Ser Ala Leu Leu Pro Gly Ile Pro Ser Arg Phe Ser Gly
     50                  55                  60

Ser Gly Ser Gly Arg Asp Tyr Thr Phe Thr Ile Ser Ser Leu Gln Pro
 65                  70                  75                  80

Glu Asp Ile Ala Thr Tyr Tyr Cys Leu Gln Tyr Asp Asp Leu Trp Thr
                 85                  90                  95

Phe Gly Gly Gly Thr Lys Leu Gln Ile Lys Arg
                100                 105

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      linker peptide

<400> SEQUENCE: 47

Gly Gly Gly Ser
  1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Phe Lys Tyr Lys
  1
```